United States Patent
He et al.

(10) Patent No.: US 11,731,965 B2
(45) Date of Patent: Aug. 22, 2023

(54) TETRAHYDROPROTOBERBERINE COMPOUND, PREPARATION METHOD THEREFOR AND USES THEREOF, AND PHARMACEUTICAL COMPOSITION

(71) Applicants: SHANGHAI INSTITUTE OF MATERIA MEDICA, CHINESE ACADEMY OF SCIENCES, Shanghai (CN); TOPHARMAN SHANGHAI CO., LTD., Shanghai (CN)

(72) Inventors: Yang He, Shanghai (CN); Xiangrui Jiang, Shanghai (CN); Jianfeng Li, Shanghai (CN); Yu Wang, Shanghai (CN); Zhen Wang, Shanghai (CN); Weiming Chen, Shanghai (CN); Fuqiang Zhu, Shanghai (CN); Chunhui Wu, Shanghai (CN); Rongxia Zhang, Shanghai (CN); Jingshan Shen, Shanghai (CN); Hualiang Jiang, Shanghai (CN)

(73) Assignees: SHANGHAI INSTITUTE OF MATERIA MEDICA, CHINESE ACADEMY OF SCIENCES, Shanghai (CN); TOPHARMAN SHANGHAI CO., LTD., Shanghai (CN)

( * ) Notice: Subject to any disclaimer, the term of this patent is extended or adjusted under 35 U.S.C. 154(b) by 0 days.

(21) Appl. No.: 16/639,394

(22) PCT Filed: Aug. 14, 2018

(86) PCT No.: PCT/CN2018/100340
§ 371 (c)(1),
(2) Date: Feb. 14, 2020

(87) PCT Pub. No.: WO2019/034031
PCT Pub. Date: Feb. 21, 2019

(65) Prior Publication Data
US 2020/0255421 A1 Aug. 13, 2020

(30) Foreign Application Priority Data

Aug. 14, 2017 (CN) .......................... 201710693250.1

(51) Int. Cl.
*C07D 455/03* (2006.01)
*C07D 498/14* (2006.01)
*A61P 25/20* (2006.01)

(52) U.S. Cl.
CPC ............ *C07D 455/03* (2013.01); *A61P 25/20* (2018.01); *C07D 498/14* (2013.01)

(58) Field of Classification Search
CPC ........................... C07D 455/03; C07D 498/14
See application file for complete search history.

(56) References Cited

U.S. PATENT DOCUMENTS 3,426,027 A  2/1969 Muller et al.
2009/0149488 A1  6/2009 Li et al.

FOREIGN PATENT DOCUMENTS

| CN | 1900075 A | 1/2007 |
|---|---|---|
| CN | 1900076 A | 1/2007 |
| CN | 101037436 A | 9/2007 |
| CN | 102796096 A | 11/2012 |
| CN | 103387583 A | 11/2013 |
| CN | 105418601 A | 3/2016 |
| JP | S5295655 A | 8/1976 |
| JP | 2012513413 A | 6/2012 |
| JP | 2014515379 A | 6/2014 |
| NL | 06501747 | 8/1965 |
| WO | 2009002873 A1 | 12/2008 |
| WO | 2010075469 A1 | 7/2010 |
| WO | 2011006000 A1 | 1/2011 |

OTHER PUBLICATIONS

STN Registry Entry for CAS RN 2086-96-6, Entered STN Nov. 16, 1984, Accessed Jun. 5, 2021.*
STN Registry database entry for CAS RN 2086-96-6, Entry Date Nov. 16, 1984; Accessed via STNext Aug. 14, 2021.*
CAS RN 19845-29-5, STN Registry Database, entered STN Nov. 16, 1984, Accessed Dec. 16, 2021 . . . .*
International Search Report dated Nov. 15, 2018 for International Application No. PCT/CN2018/100340.

(Continued)

*Primary Examiner* — Alicia L Otton
(74) *Attorney, Agent, or Firm* — Meunier Carlin & Curfman LLC

(57) ABSTRACT

The present invention provides a tetrahydroprotoberberine compound represented by the formula (I), enantiomers, diastereomers, racemates and mixtures thereof, and pharmaceutically acceptable salts, crystalline hydrates and solvates thereof. The invention also provides a method for preparing the compound and the use thereof in the preparation of a medicament for preventing and/or treating central nervous system diseases.

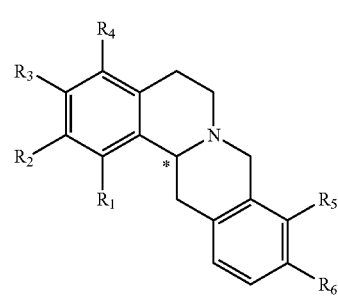

4 Claims, 1 Drawing Sheet

(56) References Cited

OTHER PUBLICATIONS

Written Opinion dated Nov. 15, 2018 for International Application No. PCT/CN2018/100340.
Yamahara et al.; "Central Depressant Action of Tetrahydroberberine and Its Derivatives"; Chem. Pharm. Bull. 24(8); dated 1976; 4 pages.
Suau et al.; "The Polonovski-Potier Reaction of Berbine N-Oxides. Synthesis of 8-Hydroxymthyl and 8-Methylberbines"; Tetrahedron 56 (2000); dated Oct. 6, 2000; 11 pages.
Barkovic et al.; "Semisynthetic berberine homologs. I. Ethers of berberrubine Farmaceutski Glasnik"; dated 1966; 8 pages.
Chen et. al.; Design synthesis and biological evaluation of novel nitric oxide donating protoberberine derivatives as antitumor agents; European Journal of Medicinal Chemistry; Dated Mar. 18, 2017; 12 pages.
Tomioka et al.; "Strategies for Organic Synthesis Based on Name Reactions"; Japan, Kagakudojin, 1 Edition, 2nd impression; dated Mar. 30, 2007; 9 pages.
Tsuji et al.; "Organic Synthesis Pioneered by Transition Metals Its Various Reaction Formats and Latest Results"; Japan, Kagakudojin, 1st addition; dated 1997; 7 pages.
Supplementary European Search Report issued in EP application No. 18846464.8; dated Jul. 31, 2020; 67 pages.
Office Action issued in JP Application No. 2020-509452; dated Apr. 13, 2021; 6 pages.

\* cited by examiner

TETRAHYDROPROTOBERBERINE COMPOUND, PREPARATION METHOD THEREFOR AND USES THEREOF, AND PHARMACEUTICAL COMPOSITION

TECHNICAL FIELD

The invention relates to the fields of medical chemistry and chemical synthesis. In particular, the present invention relates to a class of a tetrahydroprotoberberine compound with novel structures, the preparation thereof, a pharmaceutical compositions and the use thereof in the preparation of a medicament for the treatment of dopamine and 5-HT receptor-related central nervous system diseases, in particular central nervous system diseases such as Parkinson's disease, schizophrenia, drug addiction, ADHD, migraine.

BACKGROUND ART

Tetrahydroprotoberberine compounds (THPBs) are a class of an isoquinoline alkaloid having a structure of four condensed ring. This class of natural alkaloids has a wide range of pharmacological activities, such as antagonistic effect on DA receptors, antitumor, antibacterial, anti-arrhythmia, hypolipidemic, antidepressant and analgesic effect. For example, tetrahydropalmatine can he used in analgesia, hypnosis; xylopinine can he used in relieving cough and asthma; corydaline has an activity of inhibiting acetylcholinesterase. The structures of some of the tetrahydroprotoberberine compounds are as follows:

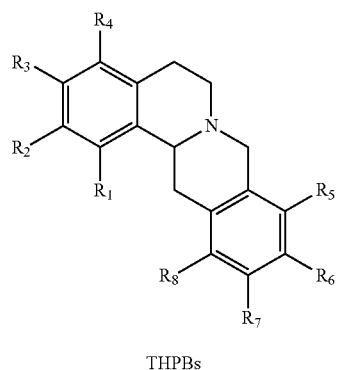

THPBs

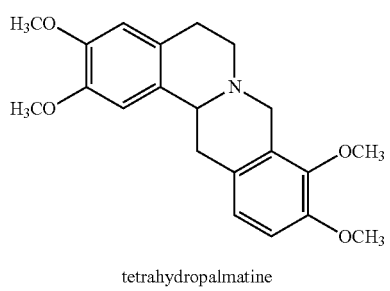

tetrahydropalmatine

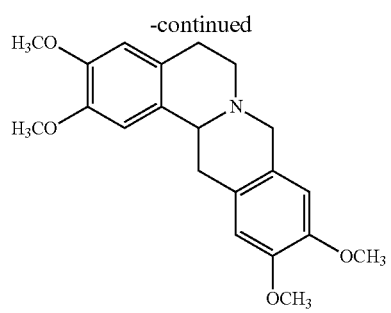

xylopinine

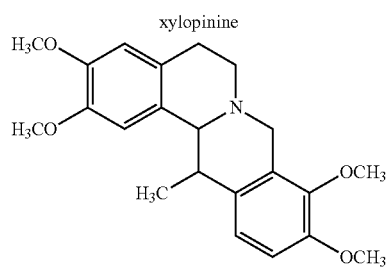

Corydaline

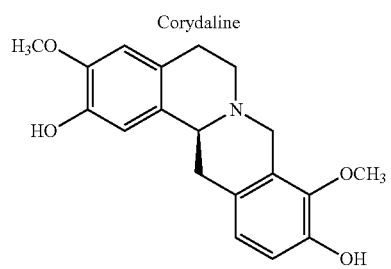

L-Stepholidine

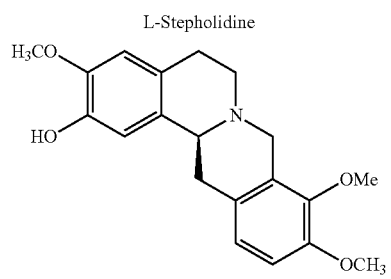

L-Closculline

The etiological argument of DA imbalance in schizophrenia indicates that the target areas of positive symptoms in patients are subcortical structures, and $D_2$ receptors in these areas are hyperactive, producing positive symptoms. The patient's negative symptoms are caused by hypofunction of the $D_1$ receptor in the prefrontal cortex (mPFC) of the cerebral cortex. $D_1$ receptor agonists can improve teaming and memory disorders. Therefore, non-classical anti-schizophrenic drugs having both $D_1$ receptor agonism and $D_2$ receptor antagonism function could match both improving the $D_1$ receptor dysfunction of mPFC, and inhibiting $D_2$ receptor hyperfunction of subcortical regions, and is one of the research directions of new anti-schizophrenics. L-Stepholidine (l-SPD) researched by the academician JIN Guozhang is the first anti-schizophrenia drug lead compound in the world with both $D_1$ agonistic-$D_2$ antagonistic function. Preliminary clinical trials have confirmed that l-SPD has the characteristics of non-classical anti-schizophrenic drugs, and it can quickly improve the negative symptoms of schizophrenia without obvious EPS and sedation effects. l-SPD also has anti-Parkinson's disease effect. Unilateral 6-OHDA.-lesioned rats is a common animal model of Parkinson's disease. In the dose range of 0.5-8 mg/kg, l-SPD was able to induce the intact side rotation behavior in a dose-dependent manner, although its maximum rotation response was significantly lower than that of the $D_1$ agonist apomorphine (APO). Early clinical trials showed that l-SPD used in combination with anti-Parkinson's disease drugs can significantly reduce movement disorder side effects occurred in PD patients. In addition, studies have shown that l-SPD can inhibit the establishment, maintenance, and reconstruction of conditioned place preference (CPP) induced by morphine, and has the potential to treat opioid addiction.

s, L-12-chloroscoulerine (l-CSL) as a derivative of l-SPD also has both $D_1$ agonistic-$D_2$ antagonistic function, and has a stronger dopamine receptor activity. However, both have the problems of low oral bioavailability, poor physical and chemical properties etc., which limit its clinical application. Therefore, their derivatives are worthy of further study.

TECHNICAL SOLUTION

It is one object of the present invention to provide a tetrahydroprotoberberine compound represented by the formula (I), enantiomers, diastereomers, racemates and mixtures thereof, and pharmaceutically acceptable salts, crystalline hydrates and solvates thereof.

It is another object of the present invention is to provide a preparation method of the compound of the above formula (I).

It is another object of the present invention is to provide a pharmaceutical composition, comprising a therapeutically effective amount of the compound of the above formula (I), enantiomers, diastereomers, racemates and mixtures thereof, and pharmaceutically acceptable salts, crystalline hydrates and solvates thereof, or the mixtures thereof.

It is still another object of the present invention is to provide use of the compound of the above formula (I), enantiomers, diastereomers, racemates and mixtures thereof, and pharmaceutically acceptable salts, crystalline hydrates and solvates thereof in the preparation of a medicament for the treatment of dopamine and 5-HT receptor-related central nervous system diseases.

Based on the above object, the present invention relates to a tetrahydroprotoberberine compound represented by the formula (I), enantiomers, diastereomers, racemates and mixtures thereof, and pharmaceutically acceptable salts, crystalline hydrates and solvates thereof,

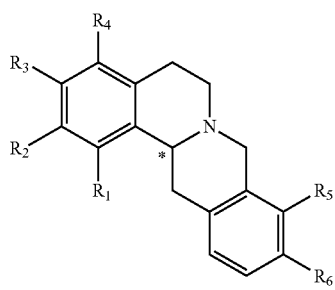

I wherein,
R1 to R4 are each independently selected from hydrogen, halogen, mercapto, C1-C6 alkoxy, halo-C1-C6 alkoxy, hydroxy-C1-C6 alkoxy, C1-C6 alkylthio, C1-C6 alkyl, C3-C6 cycloalkyl, C3-C6 cycloalkoxy, C2-C6 alkenyl, C2-C6 alkenyloxy, C2-C6 alkynyl, C2-C6 alkynyloxy, halo-C1-C6 alkyl, amino, C1-C6 alkyl substituted amino, C1-C6 alkanoyl substituted amino, C1-C6 alkyl sulfonyl substituted amino, cyano, carboxy, aldehyde group, amino-C1-C6 alkyl, hydroxy-C1-C6 alkyl, cyano-C1-C6 alkyl, C1-C6 alkanoyl, halo-C1-C6 alkanoyl, sulfoamido (—SO$_2$NH$_2$), C1-C6 alkyl substituted sulfoamido, carbamoyl (—CONH$_2$), C1-C6 alkyl substituted carbamoyl, carboxy-C1-C6 alkyl, C1-C6 alkyl sulfonyl, halo-C1-C6 alkansulfonyl, C1-C6 alkyl substituted amino-C1-C6 alkyl, C1-C6 alkanoyl substituted amino-C1-C6 alkyl, C1-C6 alkoxycarbonyl, carbamoyl-C1-C6 alkyl, or C1-C6 alkyl substituted carbamoyl-C1-C6 alkyl;

Or any two adjacent substituents of R1, R2, R3, and R4, as well as the adjacent benzene ring together may form an unsubstituted or 1-4 substituents substituted benzo[5-6 membered monocyclic heterocyclic ring], the substituent is selected from halogen, hydroxy, mercapto, oxo, thio, C1-C6 alkyl; the heterocyclic ring contains 1 to 3 heteroatoms selected from N, O and S; specifically, the benzo[5-6 membered monocyclic heterocyclic ring] is selected from:

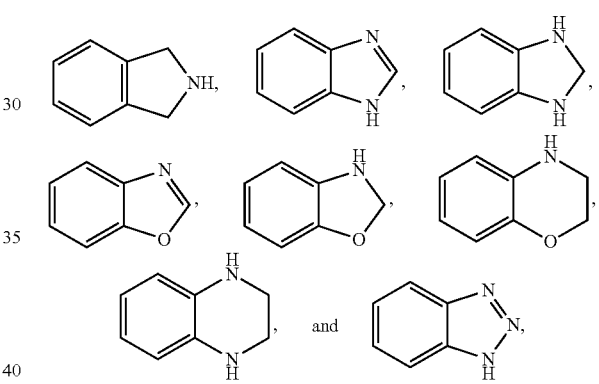

R5 to R6 are each independently selected from halogen, mercapto, C1-C6 alkoxy, halo-C1-C6 alkoxy, hydroxy-C1-C6 alkoxy, C1-C6 alkylthio, C1-C6 alkyl, C3-C6 cycloalkyl, C3-C6 cycloalkoxy, C2-C6 alkenyl, C2-C6 alkenyloxy, C2-C6 alkynyl, C2-C6 alkynyloxy, halo-C1-C6 alkyl, amino, C1-C6 alkyl substituted amino, C1-C6 alkanoyl substituted amino, C1-C6 alkyl sulfonyl substituted amino, cyano, carboxy, aldehyde group, amino-C1-C6 alkyl, hydroxy-C1-C6 alkyl, cyano-C1-C6 C1-C6 alkanoyl, halo-C1-C6 alkanoyl, sulfoamido (—SO$_2$NH$_2$), C1-C6 alkyl substituted sulfoamido, carbamoyl (—CONH$_2$), C1-C6 alkyl substituted carbamoyl, carboxy-C1-C6 alkyl, C1-C6 alkyl sulfonyl, halo-C1-C6 alkansulfonyl, C1-C6 alkyl substituted amino-C1-C6 alkyl, C1-C6 alkanoyl substituted amino-C1-C6 alkyl, C1-C6 alkoxycarbonyl, carbamoyl-C1-C6 alkyl, or C1-C6 alkyl substituted carbamoyl-C1-C6 alkyl;

And R1-R6 cannot simultaneously have 4 or more of C1-C6 alkoxy;

The configuration of the chiral carbon atom (*) at the C14 position in the compound of formula (I) is R or S; and the formula (I) does not include the following compounds:
1) 2,3,9,10-tetramethyl-6,8,13,13a-tetrahydro-5H-dibenzo[a,g] quinolizine;
2) 9,10-dimethoxy-6,8,13,13a-tetrahydro-5H-dibenzo[a, g] quinolizine;

3) 2,3,10-trimethoxy-9-amino-6,8,13,13a-tetrahydro-5H-dibenzo[a,g] quinolizine;

4) 3-methoxymethoxy-9,10-dimethoxy-6,8,13,13a-tetrahydro-5H-dibenzo[a,g] quinolizine;

5) 2,9,10-trimethoxy-3-allyloxy-6,8,13,13a-tetrahydro-5H-dibenzo[a,g] quinolizine;

6) 2,3,9-trimethoxy-10-nitro-6,8,13,13a-tetrahydro-5H-dibenzo[a,g]quinolizine;

7) 2,3,10-trimethoxy-9-methoxycarbonyl-6,8,13,13a-tetrahydro-5H-dibenzo [a,g] quinolizine.

Preferably, R1 to R4 are each independently selected from hydrogen, fluorine, chlorine, bromine, mercapto, methoxy, ethoxy, trifluoromethoxy, —SCH$_3$, —SCH$_2$CH$_3$, propyl, cyclopropyl, isopropyl, t-butyl, trifluoromethyl, difluoromethoxy, bromomethyl, chloromethyl, vinyl, vinylmethyl, amino, N-methylamino, N-ethylamino, N,N-dimethylamino, N,N-diethylamino, cyano, carboxyl, aldehyde group, —CH$_2$NH$_2$, —CH$_2$CH$_2$NH$_2$, —CH$_2$OH, —CH$_2$CH$_2$OH, —CH$_2$CN, —CH$_2$CH$_2$CN, formyl, acetyl, propionyl, trifluoroacetyl, sulfo amido (—SO$_2$NH$_2$), carbamoyl, N-methylcarbamoyl, N,N-dimethylcarbamoyl, N-ethylcarbamoyl, N,N-diethylcarbamoyl, —CH$_2$CO$_2$H, —CH$_2$CH$_2$CO$_2$H, —SO$_2$CH$_3$, —SO$_2$CF$_3$, —CH$_2$NHMe, —CH$_2$NMe$_2$, —CH$_2$CONH$_2$, —NHCOCH$_3$, —CH$_2$NHCOCH$_3$, —CH$_2$CONHMe or —CH$_2$CONMe$_2$;

Or R1 and R2, as well as the adjacent benzene ring together may form an unsubstituted or 1-2 substituents substituted benzo[5-6 membered monocyclic heterocyclic ring], the substituent is selected from halogen, hydroxy, mercapto, oxo (=O), thio (=S), C1-C6 alkyl; the heterocyclic ring contains 1 to 3 heteroatoms selected from N, O and S;

Or R2 and R3, as well as the adjacent benzene ring together may form an unsubstituted or 1-2 substituents substituted benzo[5-6 membered monocyclic heterocyclic ring], the substituent is selected from halogen, hydroxy, mercapto, oxo (=O), thio (=S), C1-C6 alkyl; the heterocyclic ring contains 1 to 3 heteroatoms selected from N, O and S;

Or R3 and R4, as well as the adjacent benzene ring together may form an unsubstituted or 1-2 substituents substituted benzo[5-6 membered monocyclic heterocyclic ring], the substituent is selected from halogen, hydroxy, mercapto, oxo(=O), thio(=S), C1-C6 alkyl; the heterocyclic ring contains 1 to 3 heteroatoms selected from N, O and S;

R5 to R6 are each independently selected from fluorine, chlorine, bromine, mercapto, methoxy, ethoxy, trifluoromethoxy, —SCH$_3$, —SCH$_2$CH$_3$, propyl, cyclopropyl, isopropyl, t-butyl, trifluoromethyl, difluoromethoxy, bromomethyl, chloromethyl, vinyl, vinylmethyl, amino, N-methylamino, N-ethylamino, N,N-dimethylamino, N,N-diethylamino, cyano, carboxyl, aldehyde group, —CH$_2$NH$_2$, —CH$_2$CH$_2$NH$_2$, —CH$_2$OH, —CH$_2$CH$_2$OH, —CH$_2$CN, —CH$_2$CH$_2$CN, formyl, acetyl, propionyl, trifluoroacetyl, sulfo amido (—SO$_2$NH$_2$), carbamoyl, N-methylcarbamoyl, N,N-dimethylcarbamoyl, N-ethylcarbamoyl, N,N-diethylcarbamoyl, —CH$_2$CO$_2$H, —CH$_2$CH$_2$CO$_2$H, —SO$_2$CH$_3$, —SO$_2$CF$_3$, —CH$_2$NHMe, —CH$_2$NMe$_2$, —CH$_2$CONH$_2$, —NHCOCH$_3$, —CH$_2$NHCOCH$_3$, —CH$_2$CONHMe or —CH$_2$CONMe$_2$.

Preferably, 2 or 3 of R1-R6 are C1-C6 alkoxy; more preferably, 2 or 3 of R1-R6 are methoxy.

Preferably, the compound of the formula (I) is a compound represented by the following formulae (I-A) to (I-G),

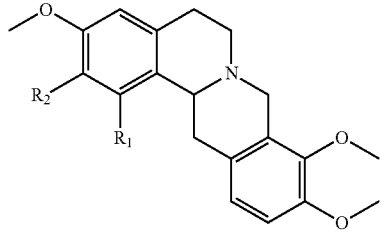

I-A

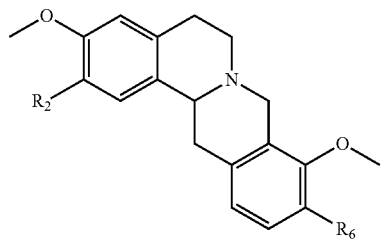

I-B

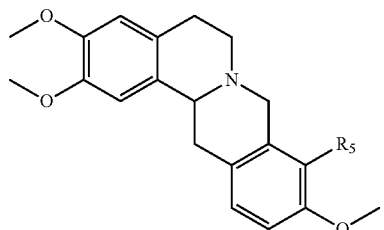

I-C

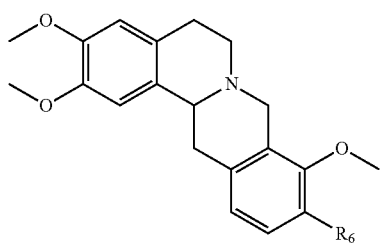

I-D

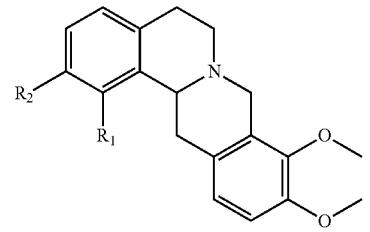

I-E

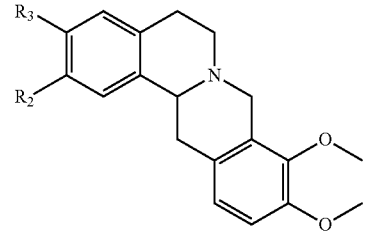

I-F

-continued

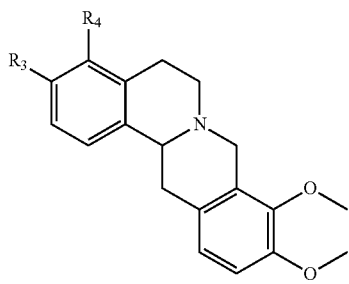

I-G wherein,

R1 to R4 are each independently selected from hydrogen, halogen, mercapto, C1-C6 alkoxy, halo-C1-C6 alkoxy, hydroxy-C1-C6 alkoxy, C1-C6 alkylthio, C1-C6 alkyl, C3-C6 cycloalkyl, C3-C6 cycloalkoxy, C2-C6 alkenyl, C2-C6 alkenyloxy, C2-C6 alkynyl, C2-C6 alkynyloxy, halo-C1-C6 alkyl, amino, C1-C6 alkyl substituted amino, C1-C6 alkanoyl substituted amino, C1-C6 alkyl sulfonyl substituted amino, cyano, carboxy, aldehyde group, amino-C1-C6 alkyl, hydroxy-C1-C6 alkyl, cyano-C1-C6 alkyl, C1-C6 alkanoyl, halo-C1-C6 alkanoyl, sulfoamido (—SO$_2$NH$_2$), C1-C6 alkyl substituted sulfoamido, carbamoyl (—CONH$_2$), C1-C6 alkyl substituted carbamoyl, carboxy-C1-C6 alkyl, C1-C6 alkyl sulfonyl, halo-C1-C6 alkyl sulfonyl, C1-C6 alkyl substituted amino-C1-C6 alkyl, C1-C6 alkanoyl substituted amino-C1-C6 alkyl, C1-C6 alkoxycarbonyl, C1-C6 alkoxycarbonyl-C1-C6 alkoxy, carbamoyl-C1-C6 alkyl, or C1-C6 alkyl substituted carbamoyl-C1-C6 alkyl;

Or R1 and R2, as well as the adjacent benzene ring together may form an unsubstituted or 1-4 substituents substituted benzo[5-6 membered monocyclic heterocyclic ring], the substituent is selected from halogen, hydroxy, mercapto, oxo (═O), thio (═S), C1-C6 alkyl; the heterocyclic ring contains 1 to 3 heteroatoms selected from N, O and S;

Or R2 and R3, as well as the adjacent benzene ring together may form an unsubstituted or 1-4 substituents substituted benzo[5-6 membered monocyclic heterocyclic ring], the substituent is selected from halogen, hydroxy, mercapto, oxo (═O), thio (═S), C1-C6 alkyl; the heterocyclic ring contains 1 to 3 heteroatoms selected from N, O and S;

Or R3 and R4, as well as the adjacent benzene ring together may form an unsubstituted or 1-4 substituents substituted benzo[5-6 membered monocyclic heterocyclic ring], the substituent is selected from halogen, hydroxy, mercapto, oxo (═O), thio (═S), C1-C6 alkyl; the heterocyclic ring contains 1 to 3 heteroatoms selected from N, O and S;

R5 to R6 is selected from cyano, carbamoyl, C1-C6 alkanoyl, C1-C6 alkanoyl substituted amino, C1-C6 alkyl sulfonyl substituted amino, C1-C6 alkanoyl substituted amino-C1-C6 alkyl, aldehyde, hydroxy-C1-C6 alkyl, amino-C1-C6 alkyl, C1-C6 alkyl, amino, hydroxy-C1-C6 alkoxy, C3-C6 cycloalkoxy, C3-C5 cycloalkyl.

Preferably, the compound of the formula (I) is selected from a compound represented by formulae (I-A-1),

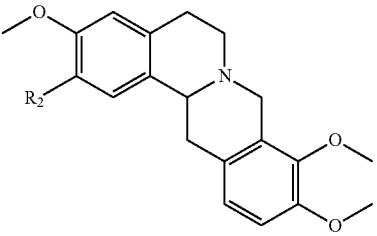

I-A-1

Wherein, R2 is selected from halogen, mercapto, halo-C1-C6 alkoxy, hydroxy-C1-C6 alkoxy, C1-C6 alkylthio, C1-C6 alkyl, C3-C6 cycloalkyl, C3-C6 cycloalkoxy, C2-C6 alkenyl, C2-C6 alkenyloxy, C2-C6 alkynyl, C2-C6 alkynyloxy, halo-C1-C6 alkyl, amino, C1-C6 alkyl substituted amino, C1-C6 alkanoyl substituted amino, C1-C6 alkyl sulfonyl substituted amino, cyano, carboxy, aldehyde group, amino-C1-C6 alkyl, hydroxy-C1-C6 alkyl, cyano-C1-C6 alkyl, C1-C6 alkanoyl, halo-C1-C6 alkanoyl, sulfoamido (—SO$_2$NH$_2$), C1-C6 alkyl substituted sulfoamido, carbamoyl (—CONH$_2$), C1-C6 alkyl substituted carbamoyl, carboxy-C1-C6 alkyl, C1-C6 alkyl sulfonyl, halo-C1-C6 alkyl sulfonyl, C1-C6 alkyl substituted amino-C1-C6 alkyl, C1-C6 alkanoyl substituted amino-C1-C6 alkyl. C1-C6 alkoxycarbonyl, carbamoyl-C1-C6 alkyl, or C1-C6 alkyl substituted carbamoyl-C1-C6 alkyl;

Preferably, R2 is selected from halogen, mercapto, halo-C1-C4 alkoxy, hydroxy-C1-C4 alkoxy, C1-C4 alkylthio, C1-C4 alkyl, C3-C5 cycloalkyl, C3-C5 cycloalkoxy, C2-C4 alkenyl, C2-C4 alkenyloxy, C2-C4 alkynyl, C2-C4 alkynyloxy, halo-C1-C4 alkyl, amino, C1-C4 alkyl substituted amino, C1-C4 alkanoyl substituted amino, C1-C4 alkyl sulfonyl substituted amino, cyano, carboxy, aldehyde group, amino-C1-C4 alkyl group, hydroxy-C1-C4 alkyl, cyano-C1-C4 alkyl group, C1-C4 alkanoyl, halo-C1-C4 alkanoyl, sulfoamido (—SO$_2$NH$_2$), C1-C4 alkyl substituted sulfoamido, carbamoyl (—CONH$_2$), C1-C4 alkyl substituted carbamoyl, carboxy-C1-C4 alkyl, C1-C4 alkansulfonyl, halo-C1-C4 alkansulfonyl, C1-C4 alkyl substituted amino-C1-C4 alkyl, C1-C4 alkanoyl substituted amino-C1-C4 alkyl, C1-C4 alkoxycarbonyl, carbamoyl-C1-C4 alkyl, or C1-C4 alkyl substituted carbamoyl-C1-C4 alkyl;

More preferably, R2 is selected from fluorine, chlorine, bromine, mercapto, trifluoromethoxy, —SCH$_3$, —SCH$_2$CH$_3$, methyl, ethyl, propyl, isopropyl, t-butyl, trifluoromethyl, bromomethyl, chloromethyl, vinyl, amino, N-methylamino, N-ethylamino, N,N-dimethylamino, N,N-diethylamino, cyano, carboxyl, aldehyde group, —CH$_2$NH$_2$, —CH$_2$CH$_2$NH$_2$, —CH$_2$OH, —CH$_2$CH$_2$OH, —CH$_2$CN, —CH$_2$CH$_2$CN, formyl, acetyl, propionyl, trifluoroacetyl, sulfo amido (—SO$_2$NH$_2$), carbamoyl, N-methylcarbamoyl, N,N-dimethylcarbamoyl, N-ethylcarbamoyl, N,N-diethylcarbamoyl, —CH$_2$CO$_2$H, —CH$_2$CH$_2$CO$_2$H, —SO$_2$CH$_3$, —SO$_2$CF$_3$, —CH$_2$NHMe, —CH$_2$NMe$_2$, —CH$_2$CONH$_2$, —CH$_2$CONHMe or —CH$_2$CONMe$_2$.

Preferably, the compound of the formula (1) of the present invention is selected from the following compounds, (1) (S)-2-methyl-3,9,10-trimethoxy-6,8,13,13a-tetrahydro-5H-dibenzo[a,g] quinolizine;

(2) (S)-2-n-propyl-3,9,10-trimethoxy-6,8,13,13a-tetrahydro-5H-dibenzo[a,g] quinolizine;

(3) (S)-2-isobutyl-3,9,10-trimethoxy-6,8,13,13a-tetrahydro-5H-dibenzo[a,g] quinolizine;
(4) (S)-2-cyano-3,9,10-trimethoxy-6,8,13,13a-tetrahydro-5H-dibenzo[a,g] quinolizine;
(5) (S)-2-carbamoyl-3,9,10-trimethoxy-6,8,13,13a-tetrahydro-5H-dibenzo[a,g] quinolizine;
(6) (S)-2-formyl-3,9,10-trimethoxy-6,8,13,13a-tetrahydro-5H-dibenzo[a,g] quinolizine;
(7) (S)-2-hydroxymethy-3,9,10-trimethoxy-6,8,13,13a-tetrahydro-5H-dibenzo [a,g] quinolizine;
(8) (S)-2-carboxy-3,9,10-trimethoxy-6,8,13,13a-tetrahydro-5H-dibenzo[a,g] quinolizine;
(9) (S)-2-ethoxycarbonyl-3,9,10-trimethoxy-6,8,13,13a-tetrahydro-5H-dibenzo [a,g] quinolizine;
(10) (S)-2-aminomethyl-3,9,10-trimethoxy-6,8,13,13a-tetrahydro-5H-dibenzo [a,g] quinolizine;
(11) (S)-2-acetaminomethyl-3,9,10-trimethoxy-6,8,13,13a-tetrahydro-5H-dibenzo[a,g] quinolizine;
(12) (S)-2-acetyl-3,9,10-trimethoxy-6,8,13,13a-tetrahydro-5H-dibenzo[a,g] quinolizine;
(13) (S)-2-amino-3,9,10-trimethoxy-6,8,13,13a-tetrahydro-5H-dibenzo[a,g] quinolizine;
(14) (S)-2-acetylamino-3,9,10-trimethoxy-6,8,13,13a-tetrahydro-5H-dibenzo[a,g] quinolizine;
(15) (S)-2-bromo-3,9,10-trimethoxy-6,8,13,13a-tetrahydro-5H-dibenzo[a,g] quinolizine;
(16) (S)-2-chloro-3,9,10-trimethoxy-6,8,13,13a-tetrahydro-5H-dibenzo[a,g] quinolizine;
(17) (S)-2-vinyl-3,9,10-trimethoxy-6,8,13,13a-tetrahydro-5H-dibenzo[a,g] quinolizine;
(18) (S)-2-hydroxyethyl-3,9,10-trimethoxy-6,8,13,13a-tetrahydro-5H-dibenzo [a,g] quinolizine;
(19) (S)-2,3,10-trimethoxy-9-cyano-6,8,13,13a-tetrahydro-5H-dibenzo[a,g] quinolizine;
(20) (S)-2,3,10-trimethoxy-9-carbamoyl-6,8,13,13a-tetrahydro-5H-dibenzo[a,g] quinolizine;
(21) (S)-2,3,10-trimethoxy-9-acetyl-6,8,13,13a-tetrahydro-5H-dibenzo[a,g] quinolizine;
(22) (S)-2,3,10-trimeloxy-9-aminomethyl-6,8,13,13a-tetrahydro-5H-dibenzo [a,g] quinolizine;
(23) (S)-2,3,10-trimethoxy-9-acetytaminomethyl-6,8,13,13a-tetrahydro-5H-dibenzo[a,g] quinolizine;
(24) (S)-2,3,10-trimethoxy-9-formyl-6,8,13,13a-tetrahydro-5H-dibenzo[a,g] quinolizine;
(25) (S)-2,3,10-trimethoxy-9-hydroxymethyl-6,8,13,13a-tetrahydro-5H-dibenzo [a,g] quinolizine;
(26) (S)-2,3,9-trimethoxy-10-methyl-6,8,13,13a-tetrahydro-5H-dibenzo[a,g] quinolizine;
(27) (S)-2,3,9-trimethoxy-10-cyano-6,8,13,13a-tetrahydro-5H-dibenzo[a,g] quinolizine;
(28) (S)-2,3,9-trimethoxy-10-carbamoyl-6,8,13,13a-tetrahydro-5H-dibenzo[a,g] quinolizine;
(29) (S)-2,3,9-trimethoxy-10-formyl-6,8,13,13a-tetrahydro-5H-dibenzo[a,g] quinolizine;
(30) (S)-2,3,9-trimethoxy-10-hydroxy methyl-6,8,13,13a-tetrahydro-5H-dibenzo [a,g] quinolizine;
(31) (S)-2,3,9-trimethoxy-10-aminomethyl-6,8,13,13a-tetrahydro-5H-dibenzo [a,g] quinolizine;
(32) (S)-2,3,9-trimethoxy-10-acetaminomethyl-6,8,13,13a-tetrahydro-5H-dibenzo[a,g] quinolizine;
(33) (S)-2,10-diamino-3,9-dimethoxy-6,8,13,13a-tetrahydro-5H-dibenzo[a,g] quinolizine;
(34) (S)-2,10-diacetylamido-3,9-dimethoxy-6,8,13,13a-tetrahydro-5H-dibenzo [a,g] quinolizine;
(35) 2,3-dicyano-9,10-dimethoxy-6,8,13,13a-tetrahydro-5H-dibenzo[a,g] quinolizine;
(36) 9,10-dimethoxy-5,6,13,13a-tetrahydroisoquinolino [3,2-a]pyrrolo[3,4-g]isoquinoline-1,3(2H,8H)-dione;
(37) (S)-2,10-dicyano-3,9-dimethoxy-6,8,13,13a-tetrahydro-5H-dibenzo[a,g] quinolizine;
(38) (S)-2,10-dicarbamoyl-3,9-dimethoxy-6,8,13,13a-tetrahydro-5H-dibenzo[a,g] quinolizine;
(39) 2,3-dicarbamoyl-9,10-dimethoxy-6,8,13,13a-tetrahydro-5H-dibenzo[a,g] quinolizine;
(40) (S)-4,10,11-trimethoxy-3,6,7,9,14,14a-hexahydroimidazo[4,5-h] isoquinolino [3,2-a]isoquinolin-2(1H)-one;
(41) (S)-4,10,11-trimethoxy-3,6,7,9,14,14a-Hexahydroimidazo[4,5-h] isoquinolino [3,2-a]isoquinoline-2(1H)-thione;
(42) (S)-4,10,11-trimethoxy-1,6,7,9,14,14a-hexahydroimidazo[4,5-h] isoquinolino [3,2 a]isoquinoline;
(43) (S)-4,10,11-trimethoxy-1,6,7,9,14,14a-hexahydroisoquinolino[3,2-a][1,2,3] triazolo [4,5-h]isoquinoline;
(44) 9,10-dimethoxy-1,5,6,8,13,13a-hexahydroimidazo [4,5-g]isoquinolino[3,2-a] isoquinoline;
(45) 9,10-dimethoxy-6,8,13,13a-tetrahydro-5H-isoquino [3,2-a]oxazolo[4,5-g] isoquinolin;
(46) 9,10-dimethoxy-3,5,6,8,13,13a-hexahydro-2H-isoquino[3,2-a]oxazolo[4,5-g] isoquinolin-2-one;
(47) 10,11-dimethoxy-4,6,7,9,14,14a-hexahydroisoquinolino[3,2-a][1,4]oxazino [3,2-g] isoquinolin-3(2H)-one;
(48) 10,11-dimethoxy-7,9,14,14a-tetrahydro-6H-isoquino [3,2-a]oxazolo[5,4-h] isoquinoline;
(49) 10,11-dimethoxy-6,7,14,14a-tetrahydro-1H-isoquino [3,2-a]oxazolo[5,4-h] isoquinolin-2(9H)-one;
(50) 11,12-dimethoxy-3,7,8,10,15,15a-hexahydroisoquinolino[3,2-a][1,4] oxazino [2,3-h] isoquinolin-2(1H)-one;
(51) (S)-2-(difluoromethoxy)-3,9,10-trimethoxy-6,8,13,13a-tetrahydro-5H-dibenzo[a,g] quinolizine;
(52) (S)-2-allyloxy-3,9,10-trimethoxy-6,8,13,13a-tetrahydro-5H-dibenzo[a,g] quinolizine;
(53) (S)-2-cyclopropoxy-3,9,10-trimethoxy-6,8,13,13a-tetrahydro-5H-dibenzo [a,g] quinolizine;
(54) (S),-cyclopentyloxy-3,9,10-trimethoxy-6,8,13,13a-tetrahydro-5H-dibenzo [a,g] quinolizine;
(55) (S)-2,10-di(hydroxyethoxy)-3,9-dimethoxy-6,8,13,13a-tetrahydro-5H-dibenzo[a,g] quinolizine;
(56) (S)-2,3,10-trimethoxy-9-hydroxyethoxy-6,8,13,13a-tetrahydro-5H-dibenzo [a,g] quinolizine;
(57) (S)-2,3,10-trimethoxy-9-cyclopropyloxy-6,8,13,13a-tetrahydro-5H-dibenzo [a,g] quinolizine;
(58) (S)-2,3,10-trimethoxy-9-cyclopentyloxy-6,8,13,13a-tetrahydro-5H-dibenzo [a,g] quinolizine;
(59) (S)-2,3,9-trimethoxy-10-cyclopropyloxy-6,8,13,13a-tetrahydro-5H-dibenzo [a,g] quinolizine;
(60) (S)-2-methanesulphonylamino-3,9,10-trimethoxy-6,8,13,13a-tetrahydro-5H-dibenzo [a,g] quinolizine.

The present invention also provides a preparation method of the compound of formula (I) and the intermediate thereof. The preparation method can be conducted through one of the following method I to method VI, and the starting materials used in the present invention are commercially purchased or prepared according to known synthesis method of similar compounds:

Method I: using a tetrahydroprotoberberine substituted with a phenol hydroxy as a raw material, alkylating with an alkylating agent to obtain the title compound; the specific reaction conditions can be referred to the patent application CN1900076A. The alkylating agent includes, but is not limited to, bromocyclopropane, bromocyclopentane, bromoethanol, chloroethanol, 3-bromopropene, and monochloradifluoromethane.

Method II: using a tetrahydroprotoberberine substituted with a phenol hydroxy (I-1a) to (I-4a) as a raw material, reacting with a sulfonylating agent in the presence of a base to obtain compounds (I-1b) to (I-4b); the (I-1b) to (I-4b) compounds and coupling reagent conducting a coupling reaction to obtain compounds of formula (I-1) to (I-4), as shown in reaction schemes 1-4:

Reaction scheme 1

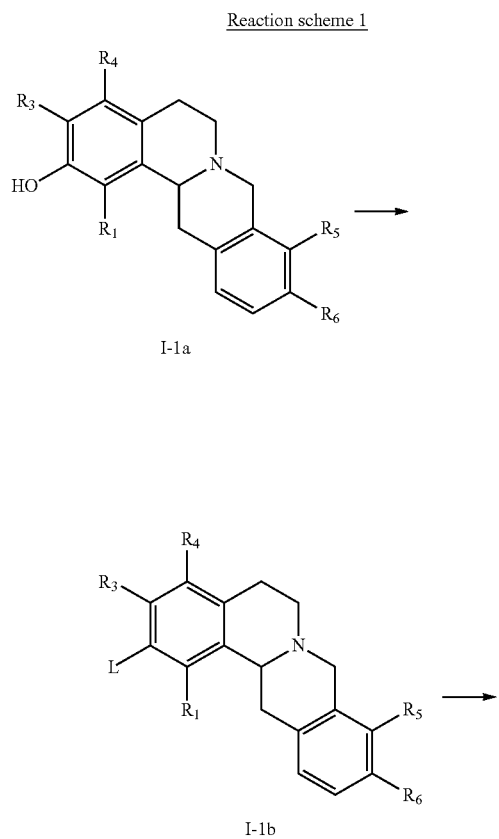

or:

Reaction scheme 2

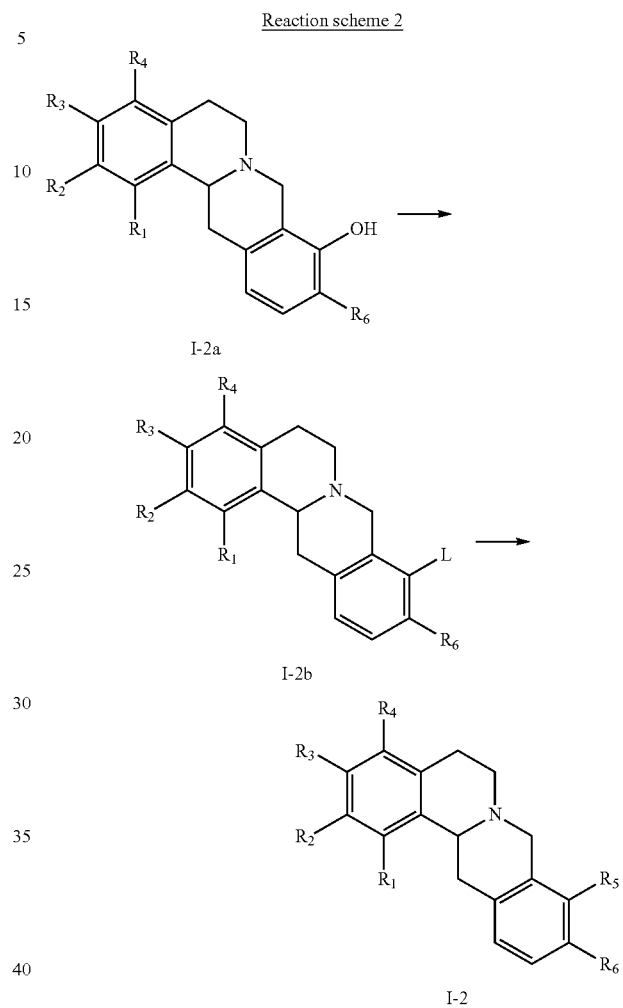

wherein R5 is selected from halogen, C1-C6 alkylthio, C1-C6 alkyl, C3-C6 cycloakyl, C2-C6 alkenyl, C2-C6 alkynyl, amino, C1-C6 alkyl substituted amino, benzylamino, cyano, carboxyl, aldehyde group, C1-C6 alkanoyl; R1-R4 are selected from hydrogen or C1-C6 alkoxy; R6 is C1-C6 alkoxy;

or:

Reaction scheme 3

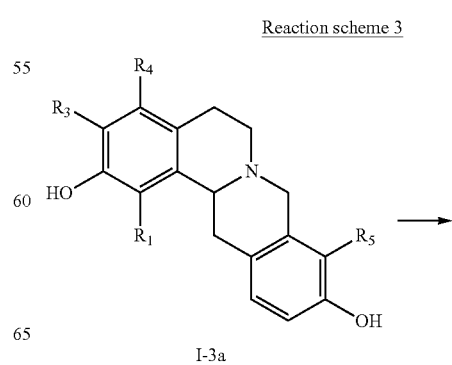

wherein R2 is selected from hydrogen, halogen, C1-C6 alkylthio, C1-C6 alkyl, C3-C6 cycloakyl, C2-C6 alkenyl, C2-C6 alkynyl, amino, C1-C6 alkyl substituted amino, benzylamino, cyano, carboxyl, aldehyde group, C1-C6 alkanoyl; R1, R3, R4 are selected from hydrogen or C1-C6 alkoxy; R5 and R6 are C1-C6 alkoxy;

13

-continued

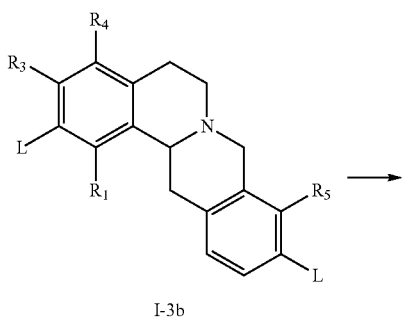

I-3b

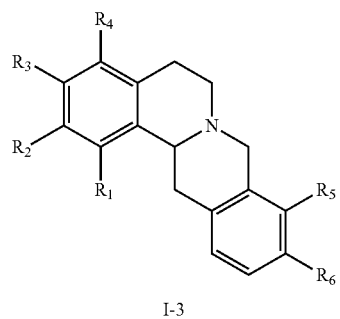

I-3 wherein R2 and R6 are simultaneously selected from hydrogen, halogen, C1-C6 alkylthio, C1-C6 alkyl, C3-C6 cycloalkyl, C2-C6 alkenyl, C2-C6 alkynyl, amino, C1-C6 alkyl substituted amino, benzylamino, cyano, carboxyl, aldehyde group, C1-C6 alkanoyl; R1, R3, and R4 are selected from hydrogen or C1-C6 alkoxy; R5 is C1-C6 alkoxy;

or:

Reaction scheme 4

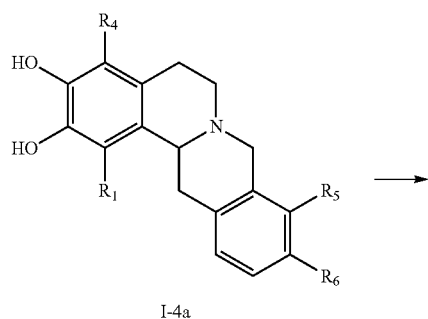

I-4a

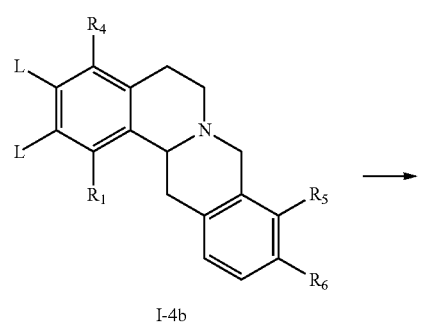

I-4b

14

-continued

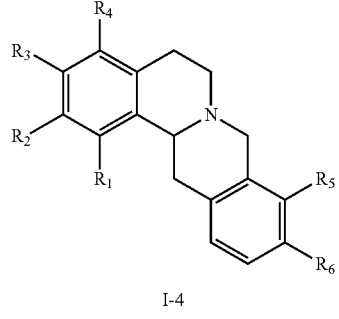

I-4 wherein R2 and R3 are simultaneously selected from hydrogen, halogen, C1-C6 alkylthio, C1-C6 alkyl, C3-C6 cycloalkyl, C2-C6 alkenyl, C2-C6 alkynyl, amino, C1-C6 alkyl substituted amino, benzylamino, cyano, carboxyl, aldehyde group, C1-C6 alkanoyl; R1 and R4 are selected from hydrogen or C1-C6 alkoxy; R5 and R6 are C1-C6 alkoxy;

L in the reaction schemes 1 to 4 represents a leaving group which is selected from C1-C6 alkyl sulfonyloxy, halo-C1-C6 alkyl sulfonyloxy, phenylsulfonyloxy, naphthyl sulfonyloxy; preferably methylsulfonyloxy and trifluoromethyl sulfonyloxy.

The sulfonylating agent is selected from C1-C6 alkyl sulfonyl chloride, C1-C6 alkyl sulfonic anhydride, benzene sulfonyl chloride, benzene sulfonic anhydride, naphthalene sulfonyl chloride, naphthalene sulfonic anhydride, preferably methyl sulfonyl chloride, methanesulfonyl acid anhydride, trifluoromethyl sulfonyl chloride and trifluoromethyl sulfonic anhydride. The solvent is selected from the group consisting of dichloromethane, tetrahydrofuran, N,N-dimethylformamide, methanol, ethanol, acetonitrile, toluene, acetone, dioxane, and chloroform.

The base is selected from inorganic or organic base, the inorganic base is selected from sodium hydroxide, potassium hydroxide, cesium hydroxide, barium hydroxide, potassium hydride, sodium hydride, sodium tert-butoxide, potassium tert-butoxide, potassium carbonate, sodium carbonate, and calcium carbonate, the organic base is selected from the group consisting of pyridine, triethylamine, diisopropylethylamine, N,N-dimethylaniline, and N,N-dimethylpyridine.

The coupling reaction is performed in the presence of a palladium catalyst and a base. The palladium catalyst is selected from palladium acetate (Pd(OAc)$_2$), di(triphenyl phosphine) palladium dichloride ((Ph$_3$P)$_2$PdCl$_2$), bis(phenylcarbonitrile) palladium chloride ((PhCN)$_2$PdCl$_2$), tetra(triphenylphosphine) palladium (Pd(PPh$_3$)$_4$), bis(triphenylphosphine) palladium acetate ((Ph$_3$P)$_2$Pd(OAc)$_2$), 1,2-di(diphenylphosphinyl) ethane palladium dichloride ((PdCl$_2$ (DPPE)$_2$)), bis(1,2-bis(diphenylphosphino)ethane) palladium(Pd(Dppe)$_2$), bis(dibenzylideneacetone) palladium(Pd(dba)$_2$), tris(dibenzylideneacetone) dipalladium (Pd$_2$(dba)$_3$), [1,3-bis(diphenyl-phosphinyl)propane] palladium dichloride (PdCl$_2$(dippp)) and [1,1'-bis(diphenylphosphino)ferrocene] palladium dichloride (Pd(dppf)Cl$_2$); the base is one or more of sodium bis(trimethylsilyl)amine, potassium tert-butoxide, sodium tert-butoxide, cesium carbonate, potassium phosphate, sodium phosphate, sodium methoxide, sodium ethoxide, potassium hydroxide, sodium hydroxide, potassium fluoride, sodium fluoride, tetrabutylammonium fluoride (TBAF), sodium acetate, potassium acetate, cesium carbonate, potassium carbonate, and sodium carbonate. The reaction solvent is not particularly limited as long as it does not interfere with the reaction. If necessary, a suitable ligand may be added as a reaction accelerator to perform the above-mentioned reaction. Suitable ligands are selected from 2,2'-diphenyl phosphinyl-1,1'-binaphthyl (BINAP), tri-tert-butylphosphine (P(t-Bu)$_3$), 1,1'-di-(diphenyl phosphinyl) ferrocene (dppf), 2-dicyclohexyl phosphate-2,4,6-triisopropylbiphenyl (x-phos), 4,5-bis-diphenyl phosphine-9,9-dimethyl-oxa anthracene (Xantphos), tri-tert-butyl phosphine tetrafluoroborate and tris(2-methylphenyl) phosphine (P(o-tolyl)$_3$). The coupling reagent includes, but is not limited to, C1-C6 alkylboronic acid, cyclopropylboronic acid, benzyl amine, potassium cyanide, zinc cyanide, tributyl vinyl tin, CO, $CO_2$, formic acid, sodium formate, lithium formate, C1-C6 alkyl sodium thiomethoxide, sodium methylsulfonate.

Method III: using a tetrahydroprotoberberine I-5a as a raw material, conducting a multi-step reaction to obtain the compound of formula (I-5), as shown in reaction scheme 5, Reaction scheme 5

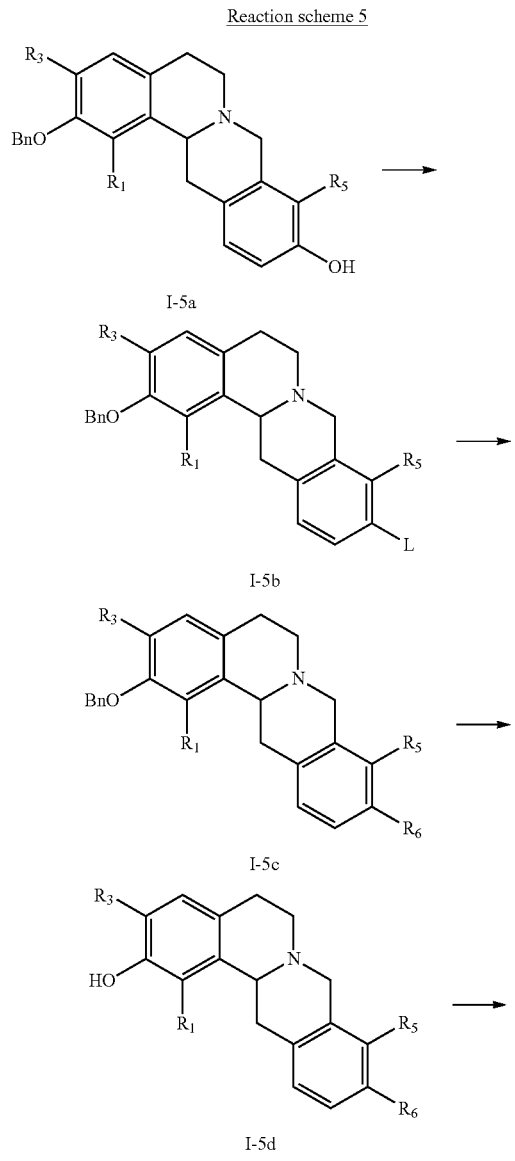

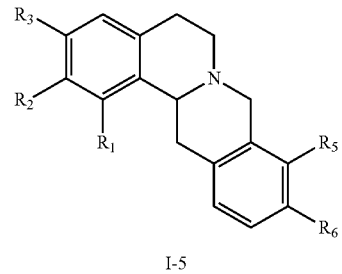

The method III comprises the following steps:
1) reacting compound of formula (I-5a) in the presence of a base with a sulfonylating agent to obtain the compound of formula (1-5b);
2) reacting compound of formula (I-5b) with a coupling agent to obtain a compound of formula (I-5c);
3) conducting a debenzylating reaction of formula (I-5c) to obtain a compound of formula (I-5d);
4) conducting a alkylating reaction of formula (I-5d) in a solvent in the presence of a base to obtain a compound of formula (I-5);
wherein R6 is selected from halogen, C1-C6 alkylthio, C1-C6 alkyl, C3-C6 cycloalkyl, C2-C6 alkenyl, C2-C6 alkynyl, C1-C6 alkyl substituted amino, cyan( ) carboxyl, aldehyde group, C1-C6 alkanoyl; R1, R3 and R5 are selected from hydrogen or C1-C6 alkoxy; R2 is C1-C6 alkoxy; L represents a leaving group and is selected from C1-C6 alkyl sulfonyloxy, halo-C1-C6 alkyl sulfonyloxy, phenyl sulfonyloxy, naphthyl sulfonyloxy; preferably methylsulfonyloxy and trifluoromethylsulfonyloxy.

The sulfonylating agent in the step 1) is selected from C1-C6 alkyl sulfonyl chloride, C1-C6 alkyl sulfonic anhydride, benzene sulfonyl chloride, benzene sulfonic anhydride, naphthalene sulfonyl chloride, naphthalene sulfonic anhydride, preferably methyl sulfonyl chloride, methanesulfonyl acid anhydride, trifluoromethyl sulfonyl chloride and trifluoromethyl sulfonic anhydride. The solvent is selected from the group consisting of dichloromethane, tetrahydrofuran, N,N-dimethylformamide, methanol, ethanol, acetonitrile, toluene, acetone, dioxane, and chloroform. The base is selected from inorganic or organic base, the inorganic base is selected from sodium hydroxide, potassium hydroxide, cesium hydroxide, barium hydroxide, potassium hydride, sodium hydride, sodium tert-butoxide, potassium tert-butoxide, potassium carbonate, sodium carbonate, and calcium carbonate, the organic base is selected from the group consisting of pyridine, triethylamine, diisopropylethylamine, N,N-dimethylaniline, and N,N-dimethylpyridine.

The coupling reaction of step 2) is performed in the presence of a palladium catalyst and a base. The palladium catalyst is selected from palladium acetate (Pd(OAc)$_2$), di(triphenyl phosphine) palladium dichloride ((Ph$_3$P)$_2$PdCl$_2$), bis(phenylcarbonitrile)palladium chloride ((PhCN)$_2$PdCl$_2$), tetra(triphenylphosphine)palladium (Pd(PPh$_3$)$_4$), bis(triphenylphosphine) palladium acetate((Ph$_3$P)$_2$Pd(OAc)$_2$), 1,2-di(diphenylphosphinyl) ethane palladium dichloride ((PdCl$_2$(dppe)$_2$)), bis(1,2-bis(diphenylphosphino)ethane)palladium(Pd(dppe)$_2$), bis(dibenzylideneacetone)palladium(Pd(dba)$_2$), tris(dibenzylideneacetone)dipalladium(Pd$_2$(dba)$_3$), [1,3-bis(diphenyl-phosphinyl)propane]palladium dichloride(PdCl$_2$(dippp)) and [1,1'-bis(diphenylphosphino)ferrocene] palladium dichloride (Pd(dppf)(Cl$_2$); the base is one or more of sodium bis (trimethylsilyl) amine, potassium tert-butoxide, sodium tert-butoxide, cesium carbonate, potassium phosphate, sodium phosphate, sodium methoxide, sodium ethoxide, potassium hydroxide, sodium hydroxide, potassium fluoride, sodium fluoride, tetrabutylammonium fluoride (TBAF), sodium acetate, potassium acetate, cesium carbonate, potassium carbonate, and sodium carbonate. The reaction solvent is not particularly limited as long as it does not interfere with the reaction. If necessary, a suitable ligand may be added as a reaction accelerator to perform the above-mentioned reaction. Suitable ligands are selected from 2,2'-diphenyl phosphinyl-1,1'-binaphthyl (BINAP) tri-tert-butylphosphine (P(t-Bu)$_3$), 1,1'-di-(diphenyl phosphinyl) ferrocene (dppf), 2-dicyclohexyl phosphate-2,4,6-triisopropylbiphenyl (x-phos), 4,5-bis-diphenyl phosphine-9, 9-dimethyl-oxa anthracene (Xantphos), tri-tert-butyl phosphine tetrafluoroborate and tris(2-methylphenyl) phosphine (P(o-tolyl)$_3$).

The debenzylation reaction of Step 3) can be conducted by catalytic hydrogenation or acid hydrolysis. The catalytic hydrogenation applies Pd/C, palladium hydroxide or palladium hydroxide/carbon as the catalyst, and hydrogen is the reducing agent. The acid hydrolysis can be conducted in hydrochloride, hydrobromide or acetic acid. The debenzylation reaction is conducted by catalytic hydrogenation or acid hydrolysis in a lower alcohol such as methanol, ethanol, isopropanol or a mixed solvent of lower alcohol-water or ethyl acetate, and the reaction is carried out at a normal pressure in the range of 20 to 100° C.;

Step 4) The solvent of alkylation reaction is selected from the group consisting of dichloromethane, tetrahydrofuran, N,N-dimethylformamide, methanol, ethanol, acetonitrile, toluene, acetone, dioxane, and chloroform. The base is selected from inorganic or organic base, the inorganic base is selected from sodium hydroxide, potassium hydroxide, cesium hydroxide, barium hydroxide, potassium hydride, sodium hydride, sodium tert-butoxide, potassium tert-butoxide, potassium carbonate, sodium carbonate, and calcium carbonate, the organic base is selected from the group consisting of pyridine, triethylamine, diisopropylethylamine, N,N-dimethylaniline, and N,N-dimethylpyridine. The alkylating agents include, but are not limited to methyl iodide, ethyl bromide, 2-bromopropane, 2-chloropropane, bromo-n-butane, bromo-n-pentane, promo-n-hexane.

Method IV: using a tetrahydroprotoberberine substituted with a phenol hydroxy (I-6a) to (I-9a) as a raw material, conducting a nitration, reduction, ring closure reaction to obtain the compound of formula (I-6) to (I-9), as shown in reaction schemes 6-9:

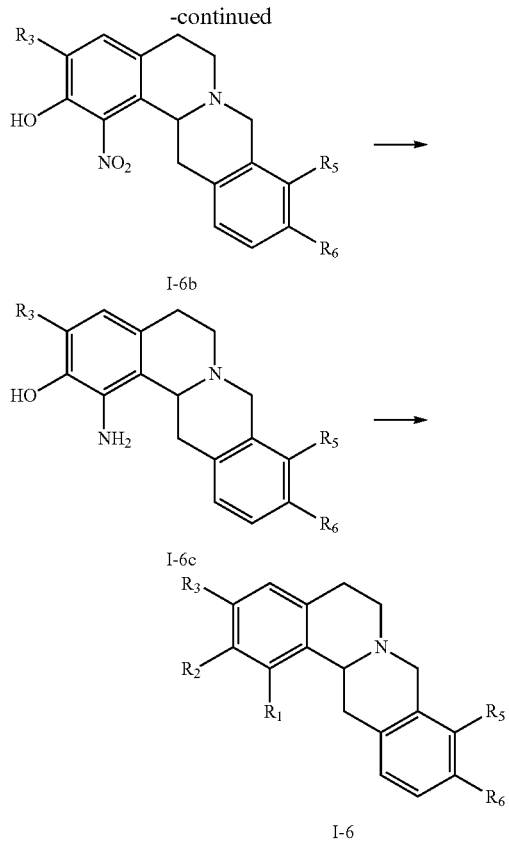

wherein, R1 and R2, as well as the adjacent benzene ring together form an unsubstituted or 1-4 substituents substituted benzo[5-6 membered monocyclic heterocyclic ring], the benzo[5-6 membered monocyclic heterocyclic ring] is selected from:

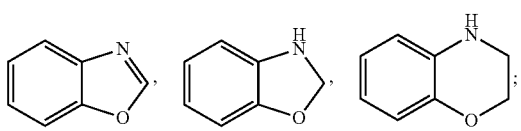

the substituted substituents are selected from halogen, hydroxy, mercapto, amino, oxo (=O), thio (=S), C1-C6 alkyl; the heterocyclic ring comprises 1 to 3 heteroatoms selected from N, O and S; R3 is selected from hydrogen or C1-C6 alkoxy; R5 and R6 are C1-C6 alkoxy;

or:

Reaction scheme 6

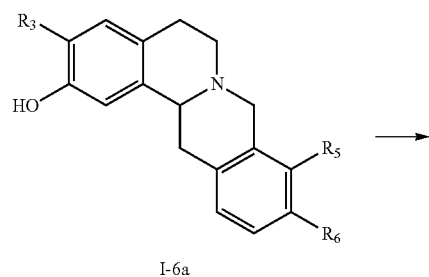

I-6a

Reaction scheme 7

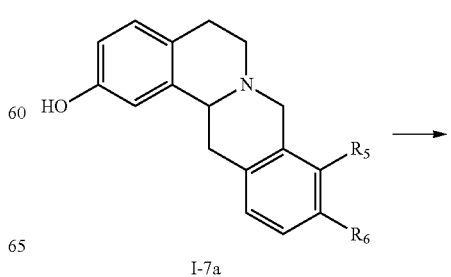

I-7a

19

-continued

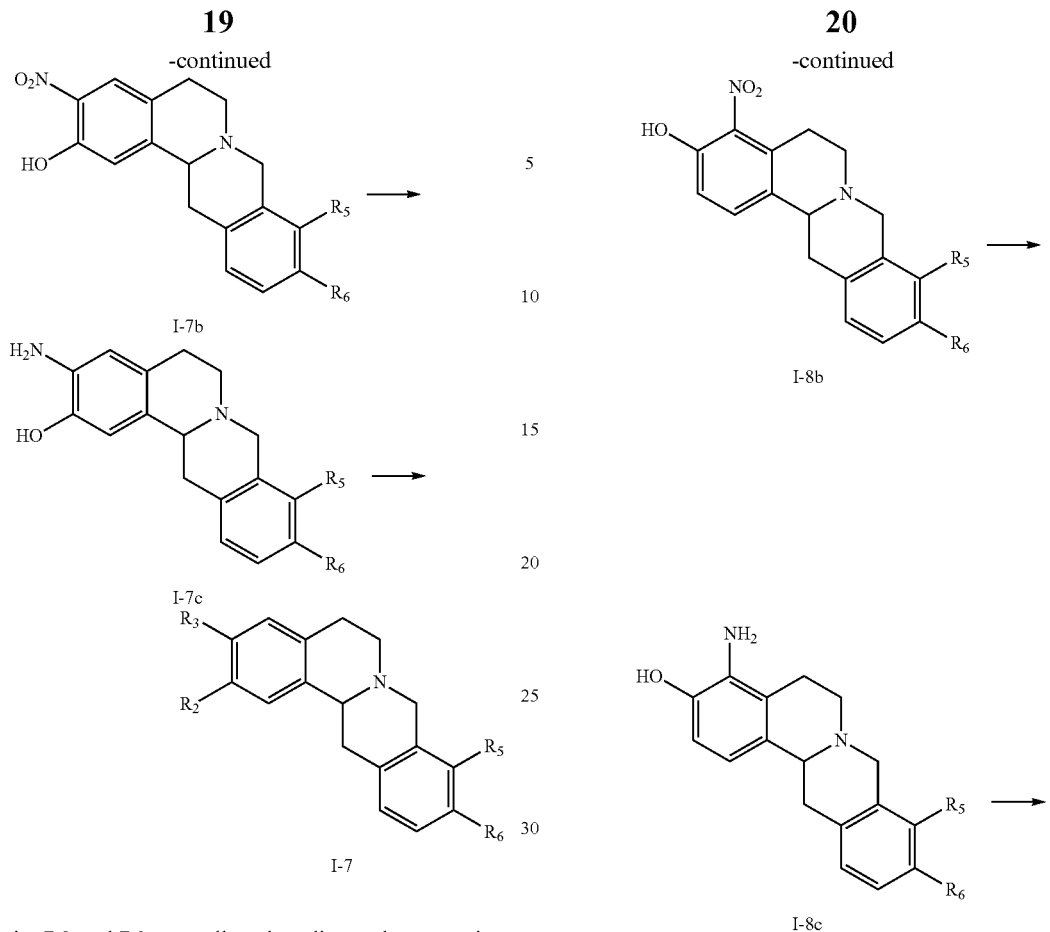

wherein, R2 and R3, as well as the adjacent benzene ring together form an unsubstituted or 1-4 substituents substituted benzo[5-6 membered monocyclic heterocyclic ring], specifically, the benzo[5-6 membered monocyclic heterocyclic ring] is selected from:

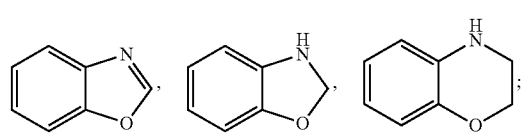

the substituted substituents are selected from halogen, hydroxy, mercapto, amino, oxo (=O), thio (=S), C1-C6 alkyl; the heterocyclic ring comprises 1 to 3 heteroatoms selected from N, O and S; R5 and R6 are C1-C6 alkoxy;

or,

Reaction scheme 8

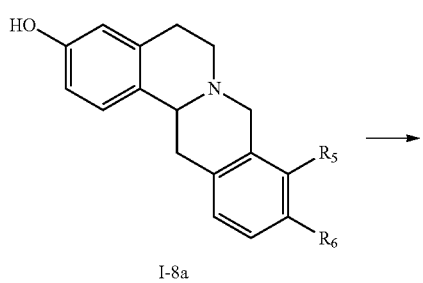

20

-continued

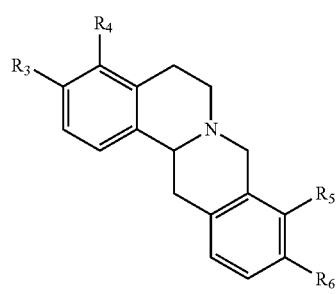

wherein, R3 and R4, as well as the adjacent benzene ring together form an unsubstituted or 1-4 substituents substituted benzo[5-6 membered monocyclic heterocyclic ring], the substituted substituents are selected from halogen, hydroxy, mercapto, amino, oxo (=O), thio (=S), C1-C6 alkyl; the heterocyclic ring comprises 1 to 3 heteroatoms selected from N, O and S; specifically, the benzo[5-6 membered monocyclic heterocyclic ring] is selected from:

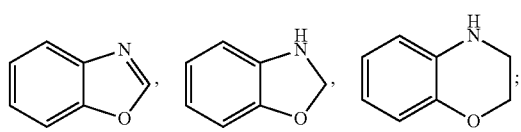

R5 and R6 are C1-C6 alkoxy;
or,

Reaction scheme 9

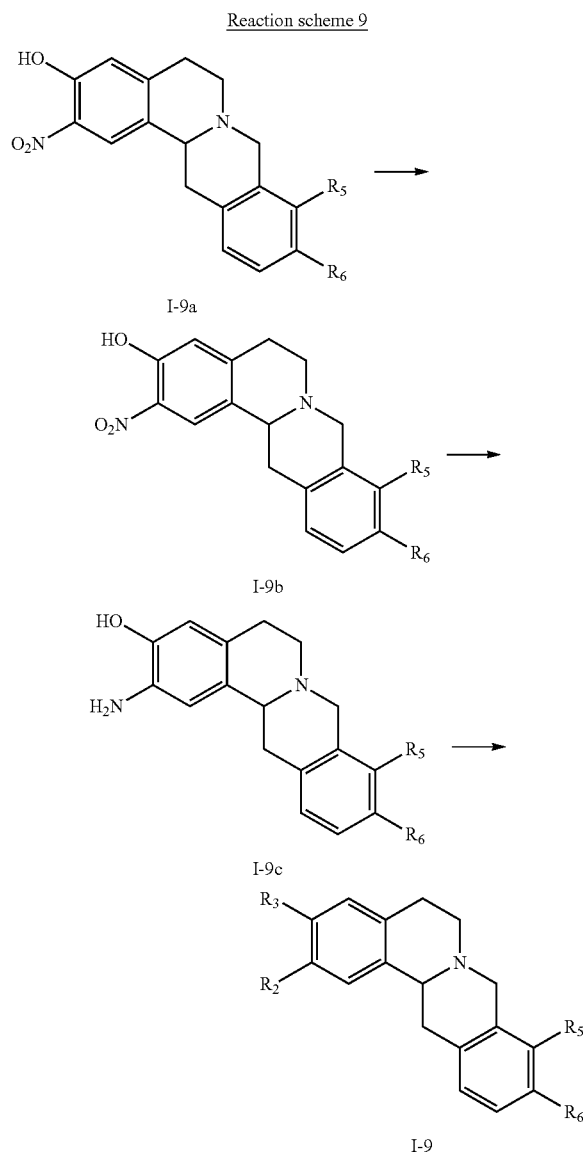

wherein, R2 and R3, as well as the adjacent benzene ring together form an unsubstituted or 1-4 substituents substituted benzo[5-6 membered monocyclic heterocyclic ring], the substituted substituents are selected from halogen, hydroxy, mercapto, amino, oxo (=O), thio (=S), C1-C6 alkyl; the heterocyclic ring comprises 1 to 3 heteroatoms selected from N, O and S; specifically, the benzo[5-6 membered monocyclic heterocyclic ring] is selected from:

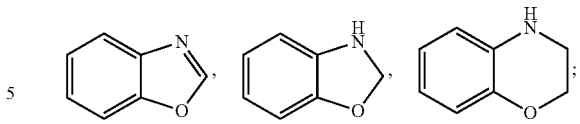

R5 and R6 are C1-C6 alkoxy;

The nitrating agent in the nitration reaction may be selected from nitric acid with various concentrations, a mixture of concentrated sulfuric acid and nitric acid, a mixture of nitric acid, sodium nitrate and concentrated sulfuric acid, a Mixture of potassium nitrate and concentrated sulfuric acid, a mixture of sodium nitrite and concentrated sulfuric acid, a mixture of acetic acid and nitric acid, preferably a mixture of acetic acid and nitric acid. When the nitrating agent is a mixture, the mixing ratio is not limited, and the reaction temperature is between −20° C. and room temperature.

The reduction reaction is conducted by using Pd/C as catalyst, and is conducted in a lower-alcohol such as methanol, ethanol, isopropyl alcohol or a mixed solvent of a lower-alcohol-water. The hydrogenation is conducted in a range of 0 to 40° C. and a normal pressure.

The ring-closure reaction is performed in the presence of a ring-closure agent in the presence or absence of a base. The ring-closure agent includes, but is not limited to, phosgene, triphosgene, 1,1'-carbonyldiimidazole (CDI), urea, carbon tetrabromide, formic acid, trimethyl orthoformate, trimethyl orthoacetate, triethyl orthoacetate, acetyl chloride, chloroacetyl chloride, bromoacetyl bromide, bromoacetyl chloride, and the like. The base is selected from inorganic or organic base, the inorganic base is selected from sodium hydroxide, potassium hydroxide, potassium hydride, sodium hydride, sodium tert-butoxide, potassium tert-butoxide, potassium carbonate, sodium carbonate, cesium carbonate, and sodium bicarbonate, the organic base is selected from the group consisting of pyridine, triethylamine, diisopropylethylamine, N,N-dimethylaniline and N,N-dimethylpyridine; the reaction solvent is not particularly limited as long as it does not affect the reaction.

Method V: using a compound of formula (I-10a) or (I-7a) as a raw material, conducting a multi-step reaction to obtain the compound of formula (I-10) or (I-11), as shown in reaction scheme 10 and 11, Reaction scheme 10

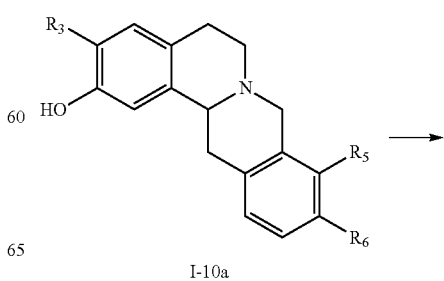

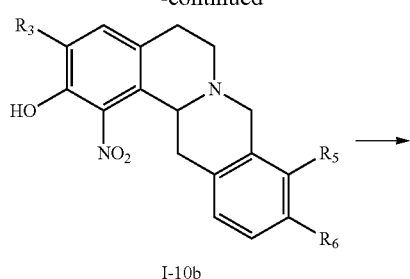

I-10b

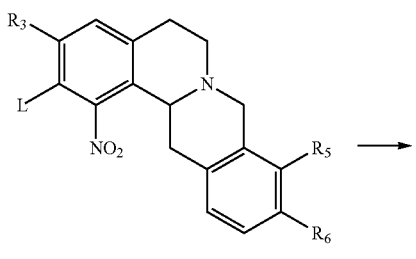

I-10c

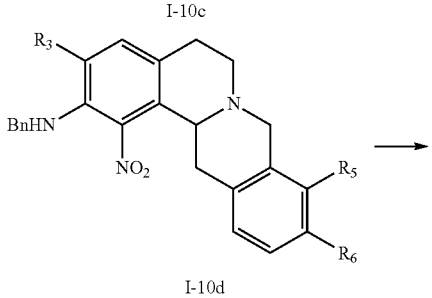

I-10d

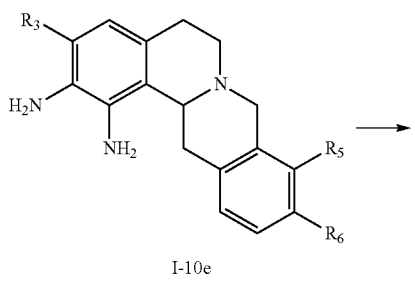

I-10e

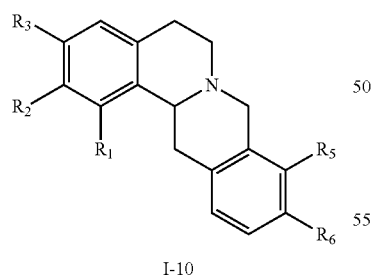

I-10 wherein, R1 and R2, as well as the adjacent benzene ring together form an unsubstituted or 1-4 substituents substituted benzo[5-6 membered monocyclic heterocyclic ring], the substituted substituents are selected from halogen, hydroxy, mercapto, amino, oxo (=O), thio (=S), C1-C6 alkyl; the heterocyclic ring comprises 1 to 3 heteroatoms selected from N, O and S; specifically the benzo[5-6 membered monocyclic heterocyclic ring] is selected from:

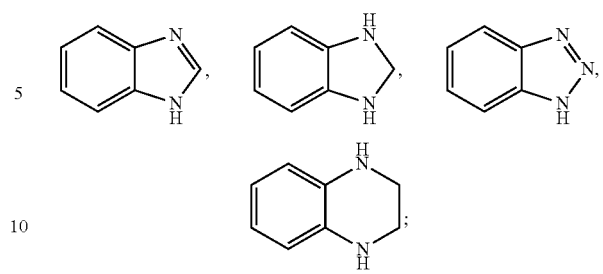

L represents a leaving group and is selected from C1-C6 alkyl sulfonyloxy, halo-C1-C6 alkyl sulfonyloxy, phenyl sulfonyloxy, naphthyl sulfonyloxy; preferably methylsulfonyloxy and trifluoromethylsulfonyloxy, R3 is selected from hydrogen or C1-C6 alkoxy; R5 and R6 are C1-C6 alkoxy; or:

Reaction scheme 11

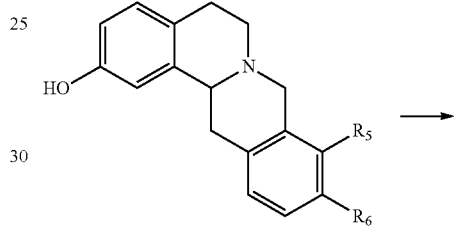

I-7a

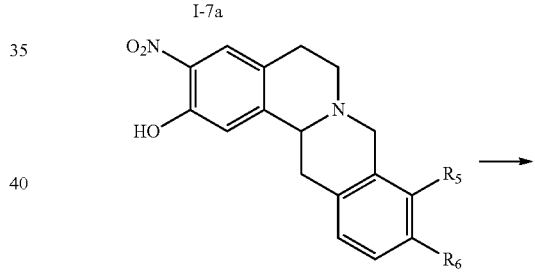

I-7b

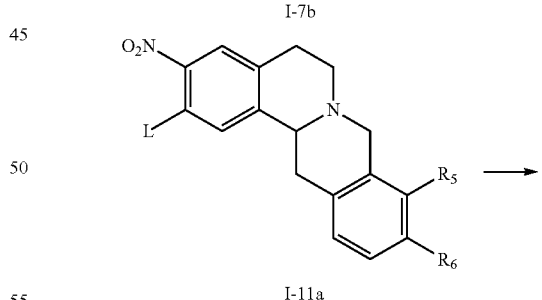

I-11a

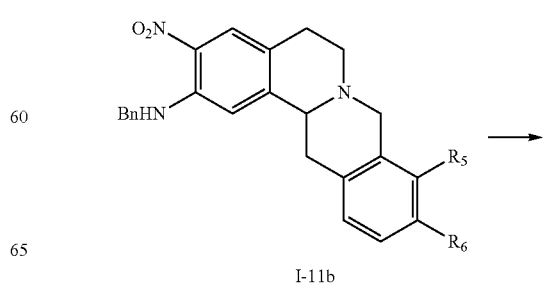

I-11b

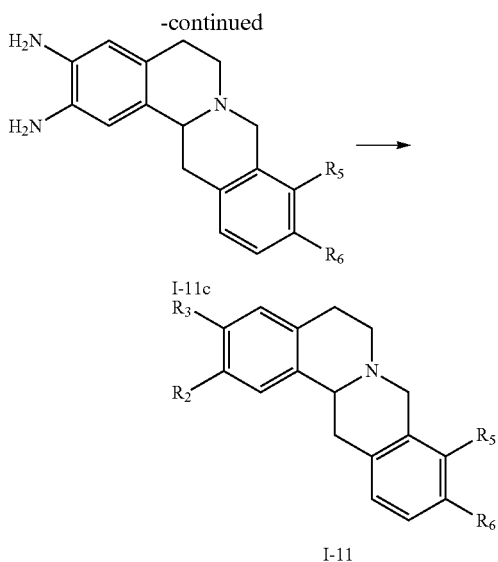

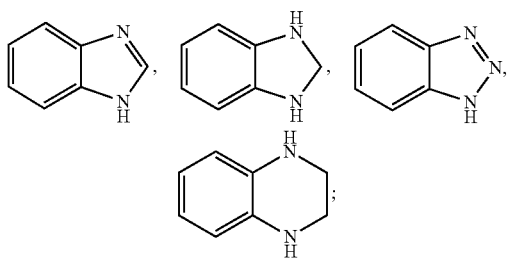

L represents a leaving group and is selected from C1-C6 alkyl sulfonyloxy, halo-C1-C6 alkyl sulfonyloxy, phenyl sulfonyloxy, naphthyl sulfonyloxy; preferably methylsulfonyloxy and trifluoromethylsulfonyloxy, R5 and R6 are C1-C6 alkoxy;

the method V comprises the following steps:

1) the compound of formula (I-10a) or (I-7a) and a nitrating agent conducting an ortho nitrating reaction to obtain a compound of formula (I-10b) or (I-7b);

2) reacting the compound of formula (I-10b) or (I-7b) and a sulfonylating agent in the presence of a base in a suitable solvent to obtain the compound of formula (I-10c) or (I-11a);

3) the compound of formula (I-10c) or (I-11a) and benzylamine conducting a Buchwald-Hartig reaction to obtain a compound of formula (I-10d) or (I-11b);

4) conducting a reduction reaction of the compound of formula (I-10d) or (I-11b) to obtain a compound of formula (I-10e) or (I-11c);

5) conducting a ring-closure reaction of the compound of formula. (I-10e) or (I-11c) to obtain a compound of formula (1-10) or (I-11);

In the above method,

The nitrating agent in the step 1) may be a mixture of concentrated sulfuric acid and nitric acid, a mixture of nitric acid, sodium nitrate and concentrated sulfuric acid, a mixture of potassium nitrate and concentrated sulfuric acid, a mixture of sodium nitrite and concentrated sulfuric acid, a mixture of acetic acid and nitric acid, preferably a mixture of acetic acid and nitric acid. The mixing ratio is not limited, and the reaction temperature is between −20° C. and room temperature, the reaction time is 10 minutes to 12 hours.

The sulfonylating agent in the step 2) is selected from C1-C6 alkyl sulfonyl chloride, C1-C6 alkyl sulfonic anhydride, benzene sulfonyl chloride, benzene sulfonic anhydride, naphthalene sulfonyl chloride, naphthalene sulfonic anhydride, preferably methyl sulfonyl chloride, methanesulfonyl acid anhydride, trifluoromethyl sulfonyl chloride and trifluoromethyl sulfonic anhydride. The solvent is selected from the group consisting of dichloromethane, tetrahydrofuran, N,N-dimethylformamide, methanol, ethanol, acetonitrile, toluene, acetone, dioxane, and chloroform. The base is selected from inorganic or organic base, the inorganic base is selected from sodium hydroxide, potassium hydroxide, cesium hydroxide, barium hydroxide, potassium hydride, sodium hydride, sodium tert-butoxide, potassium tert-butoxide, potassium carbonate, sodium carbonate, and calcium carbonate, the organic base is selected from the group consisting of pyridine, triethylamine, diisopropylethylamine, N,N-dimethylaniline, and N,N-dimethylpyridine.

The coupling reaction of step 3) is performed in the presence of a palladium catalyst and a base. The palladium catalyst is selected from palladium acetate (Pd(OAc)$_2$), di(triphenyl phosphine) palladium dichloride ((Ph$_3$P)$_2$PdCl$_2$), bis(phenylcarbonitrile)palladium chloride ((PhCN)$_2$PdCl$_2$), tetra(triphenylphosphine)palladium (Pd(PPh$_3$)$_4$), bis(triphenylphosphine) palladium acetate((Ph$_3$P)$_2$Pd(OAc)$_2$), 1,2-di(diphenylphosphinyl) ethane palladium dichloride (PdCl$_2$(dppe)$_2$), bis(1,2-bis(diphenylphosphino)ethane)palladium(Pd(dppe)$_2$), bis(dibenzylideneacetone)palladium(Pd(dba)$_2$), tris(dibenzylideneacetone)dipalladium(Pd$_2$(dba)$_3$), [1,3-bis(diphenyl-phosphinyl)propane]palladium dichloride(PdCl$_2$(dippp)) and [1,1'-bis(diphenylphosphino)ferrocene] palladium dichloride (Pd(dppf)Cl$_2$); the base is one or more of sodium bis (trimethylsilyl) amine, potassium tert-butoxide, sodium tert-butoxide, cesium carbonate, potassium phosphate, sodium phosphate, sodium methoxide, sodium ethoxide, potassium hydroxide, sodium hydroxide, potassium fluoride, sodium fluoride, tetrabutylammonium fluoride (TBAF), sodium acetate, potassium acetate, cesium carbonate, potassium carbonate, and sodium carbonate. The reaction solvent is not particularly limited as long as it does not interfere with the reaction. If necessary, a suitable ligand may be added as a reaction accelerator to perform the above-mentioned reaction. Suitable ligands are selected from 2,2'-diphenyl phosphinyl-1,1'-binaphthyl (BINAP) tri-tert-butylphosphine (P(t-Bu)$_3$), 1,1'-di-(diphenyl phosphinyl) ferrocene (dppf), 2-dicyclohexyl phosphate-2,4,6-triisopropylbiphenyl (x-phos), 4,5-bis-diphenyl phosphine-9, 9-dimethyl-oxa anthracene (Xantphos), tri-tert-butyl phosphine tetrafluoroborate and tris(2-methylphenyl) phosphine (P(o-tolyl)$_3$).

The reduction reaction of step 4) is conducted by using Pd/C, palladium hydroxide or palladium hydroxide/carbon as catalyst, using ammonium formate or hydrogen as reducing agent, and is conducted in a lower-alcohols such as methanol, ethanol, isopropyl alcohol or a mixed solvent of a lower-alcohol-water, and is conducted in a range of 20 to 100° C. and a normal pressure.

The ring-closure reaction of step 5) is performed in the presence of a ring-closure agent in the presence or absence of a base. The ring-closure agent includes, but is not limited to, phosgene, triphosgene. 1,1'-carbonyldiimidazole (CDI), urea, formic acid, sodium nitrite, carbon disulfide, thiophosgene, triethyl orthoacetate, chloroacetic acid, bromoacetic acid, ethyl bromoacetate, methyl bromoacetate, chloroacetamide, and the like. The base is selected from inorganic or organic base, the inorganic base is selected from sodium hydroxide, potassium hydroxide, potassium hydride, sodium hydride, sodium tert-butoxide, potassium tert-butoxide, potassium carbonate, sodium carbonate, cesium carbonate, and sodium bicarbonate, the organic base is selected from the group consisting of pyridine, triethylamine, diisopropylethylamine, N,N-dimethylaniline and N,N-dimethylpyridine; the reaction solvent is not particularly limited as long as it does not affect the reaction.

Method VI:

Conducting a functional group conversing of the compounds of the formulae (I-1) to (I-11) obtained by the methods I to V to obtain the title compound.

The functional group conversing reaction is, for example, an oxidative hydrolysis reaction, borohydride-oxidation reaction, condensation acylation reaction, reduction reaction, acylation reaction, esterification reaction, Grignard reaction, chlorination reaction or bromination reaction, and the like.

The oxidative hydrolysis reaction is performed in the presence of an oxidant and a base. The oxidative hydrolysis system includes, but is not limited to, hydrogen peroxide/sodium hydroxide, hydrogen peroxide/potassium hydroxide, hydrogen peroxide/potassium carbonate, and hydrogen peroxide/sodium carbonate and so on.

The borohydride-oxidation reaction is that an olefin group is first added with a boron reagent, and then is oxidized and hydrolyzed to an alcohol; the boron reagent includes, but is not limited to, borane, 9-BBN, etc.; the oxidative hydrolysis system includes but not limited to: hydrogen peroxide/sodium hydroxide, hydrogen peroxide/potassium hydroxide, hydrogen peroxide/potassium carbonate, and hydrogen peroxide/sodium carbonate and so on.

The condensation acylation reaction is conducted in presence of a condensing agent which includes, but not limited to: N,N'-dicyclohexyl carbodiimide (DCC), 1-ethyl-3-(3-dimethyl aminopropyl) carbodiimide (EDCI), O-benzotriazolyl-N,N,N',N'-tetramethyl urea tetrafluoroborate (TBTU) and the like.

The reduction reaction is performed in the presence of a reducing agent. The reducing agent includes, but is not limited to, hydrogen, ammonium formate, sodium borohydride, potassium borohydride, diisobutylaluminum hydride (DIBAL), borane, and the like.

The acylating reaction is carried out in the presence of an acylating agent, the acylating agents include, but are not limited to: acetyl chloride, acetic anhydride, propionyl chloride, propionic anhydride, methylsulfonyl chloride and the like.

The esterification reaction system includes, but is not limited to, thionyl chloride/methanol, thionyl chloride/ethanol, and the like.

The chlorination reaction is performed in the presence of a chlorinating reagent, which includes but is not limited to: thionyl chloride, phosphorus pentachloride, N-chlorosuccinimide (NCS), and the like.

The Grignard reaction is performed in the presence of a Grignard reagent, which includes but is not limited to: methyl magnesium bromide, methyl magnesium chloride, methyl magnesium iodide, and the like.

The bromination reaction is performed in the presence of a brominating reagent, and the brominating reagent includes, but is not limited to, elemental bromine, N-bromosuccinimide (NBS), and the like.

The "pharmaceutically acceptable inorganic or organic salt" in the present invention is a salt formed by reacting the compound represented by the formula (I) with an inorganic acid such as hydrochloric acid, hydrobromic acid, hydroiodic acid, hydrofluoric acid, sulfuric acid, nitric acid, or phosphoric acid, with organic acids such as formic acid, acetic acid, propionic acid, oxalic acid, malonic acid, maleic acid, tartaric acid, malic acid, fumaric acid, methanesulfonic acid or citric acid, or sodium, potassium, calcium or ammonium salts formed by reacting the compound represented by the formula (I) with base such as sodium hydroxide, of potassium hydroxide, calcium hydroxide or ammonia, "Pharmaceutically acceptable salts" also include their solvates. Examples of the solvates include hydrates and alcoholates.

The present invention also provides use of the tetrahydroprotoberberine compound of formula (I) of the present invention, enantiomers, diastereomers, racemates and mixtures thereof, and pharmaceutically acceptable salts, crystalline hydrates and solvates thereof in the preparation of a medicament for the prevention and/or treatment of diseases of the central nervous system.

The present invention further provides a method for the prevention and/or treatment of diseases of the central nervous system, comprising: administrating one of the tetrahydroprotoberberine compound of formula (I) of the present invention, enantiomers, diastereomers, racemates and mixtures thereof, and pharmaceutically acceptable salts, crystalline hydrates, solvates thereof, or the mixture of the above, to a person or an animal.

The present invention further provides a pharmaceutical composition, comprising a therapeutically effective amount of the tetrahydroprotoberberine compound of the formula (I). enantiomers, diastereomers, racemates and mixtures thereof, and pharmaceutically acceptable salts, crystalline hydrates and solvates thereof, and optionally a pharmaceutically acceptable carrier. The pharmaceutical composition can be used to prevent and/or treat of diseases of the central nervous system The present invention further provides a preparation method of the pharmaceutical composition, comprising the step of mixing the one or more of a) tetrahydroprotoberberine compound of the formula (I), enantiomers, diastereomers, racemates and mixtures thereof, and pharmaceutically acceptable salts, crystalline hydrates and solvates thereof, with b) a pharmaceutically acceptable carrier.

In the pharmaceutical composition of the present invention, a variety of pharmaceutical preparation dosage forms can be selected according to the purpose of treatment, generally including: tablets, pills, capsules, granules, suspensions, solutions, creams, ointments, powders, suppositories, gas aerosols and injections.

The aforementioned central nervous system disease is selected from schizophrenia; rebellious, unmanageable or chronic schizophrenia; affective disorder; mental disorder; emotional disorder; Type I bipolar affective disorder; type II bipolar affective disorder; depression; endogenous depression; major depression; rebellious depression; severe emotional disorder; circulatory affective disorder; panic attack;

panic disorder; social phobia; obsessive-compulsive attitudes and behavioral disorders; impulsive disorders; post-traumatic stress disorder; anxiety disorder; acute stress disorder; hysteria; anorexia nervosa; adaptive disorder; cognitive impairment; autism; neurological headache; mania; Parkinson's disease; Huntington's disease; Alzheimer's disease; dementia; memory disorders; attention deficit hyperactivity disorder; drug addiction; sleep disorders; attention deficit/hyperactivity diseases and tic.

The definition of each group in the formula (1) is as follows:

The term halogen generally refers to fluorine, chlorine, bromine and iodine; preferably fluorine, chlorine or bromine; more preferably fluorine or chlorine;

C1-C6 alkyl means a linear or branched saturated hydrocarbon group containing 1-6 carbon atoms, for example, methyl, ethyl, n-propyl, isopropyl, n-butyl, isobutyl, tert-butyl, sec-butyl, n-pentyl, 1-ethylpropyl, isopentyl, neopentyl, isohexyl, 3-methylpentyl or n-hexyl, etc., preferably methyl, ethyl, n-propyl, isopropyl, butyl, isobutyl or tert-butyl;

Halo-C1-C6 alkyl means the hydrogen atom of a linear or brandied saturated hydrocarbon group containing 1-6 carbon atoms is substituted with one or more identical or different halogen atoms, such as trifluoromethyl, fluoromethyl, difluoromethyl, chloromethyl, bromomethyl, dichlorofluoromethyl, chloroethyl, bromopropyl, 2-chloro-butyl or pentafluoroethyl group and the like;

C1-C6 alkoxy means a linear or branched alkoxy group containing 1-6 carbon atoms, for example, methoxy, ethoxy, n-propoxy, isopropoxy, n-butoxy, iso-butoxy, tert-butoxy, sec-butoxy, n-pentyloxy, isopentyloxy neopentyloxy, isohexyloxy, 3-methylpentyloxy or n-hexyloxy, etc., preferably methoxy group, ethoxy, n-propoxy, isopropoxy, n-butoxy, iso-butoxy or tert-butoxy group;

Halo-C1-C6 alkoxy means the hydrogen atom of a linear or branched alkoxy containing 1-6 carbon atoms is substituted with one or more identical or different halogen atoms, such as $-OCF_3$, $-OCH_2CH_2Cl$, $-OCHBrCH_2Cl$ or $-OCF_2CF_3$, etc.;

C1-C6 alkylthio means a linear or branched alkylthio containing 1-6 carbon atoms, such as methylthio, ethylthio, n-propylthio, isopropylthio, n-butylthio, iso butylthio, tert-butylthio, sec-butylthio, n-pentylthio, isopentylthio, neopentylthio or n-hexylthio, etc., preferably methylthio, ethylthio, n-propylthio, isopropylthio, n-butylthio, isobutylthio or tert-butylthio;

C2-C6 alkenyl refers to a linear or branched unsaturated hydrocarbon group containing 1 to 3 double bonds and 2 to 6 carbon atoms, including both cis configuration and trans configuration. For example, vinyl, 1-propenyl, 2-propenyl, 1-methyl-1-propenyl, 2-methyl-1-propenyl, 2-methyl-2-propenyl, 1-butenyl, 2-butenyl, 3-butenyl, 1-pentenyl, 2-pentenyl, 3-pentenyl, 4-pentenyl, 1,3-butadienyl, 1,3-pentadienyl, 1-hexenyl, 2-hexenyl, 3-hexenyl, 4-hexenyl, 5-hexenyl, 3,3-dimethyl-1-propenyl or 2-ethyl-1-propenyl, etc.;

C2-C6 alkynyl means a linear or branched alkynyl containing 2-6 carbon atoms, e.g., ethynyl, 2-propynyl group, 2-butynyl group, 3-butynyl group, 1-methyl-2-propynyl, 2-pentynyl, 2-pentynyl or 2-hexynyl, etc.;

C2-C6 alkenyloxy means a linear or branched alkenyloxy containing 1 to 3 double bonds and 2-6 carbon atoms, such as vinyloxy, 1-propenyloxy, 1-methyl-1-propenyloxy, 2-methyl-1-propenyloxy, 1-pentenyloxy, 1,3-pentadienyloxy or 2-pentenyloxy, etc.;

C2-C6 alkynyloxy means a linear or branched alkynyloxy containing 2-6 carbon atoms, e.g., ethynyloxy, 2-propynyloxy, 2-butynyloxy, 3-butynyloxy, 1-methyl-2-propynyloxy, 2-pentynyloxy or 2-hexynyloxy, etc.;

C1-C6 alkanoyl means a linear or branched alkanoyl containing 1-6 carbon atoms, such as formyl, acetyl, propanoyl, butanoyl, isobutanoyl, pentanoyl, tert-butanoyl of hexanoyl etc.;

Halo-C1-C6 alkanoyl means the hydrogen of a linear or branched alkanoyl containing 1-6 is substitueted by one or more identical or different halogen atoms, such as trifluoroacetyl group and the like;

C1-C6 alkyl-substituted carbamoyl means the hydrogen of the carbamoyl is substitueted by one or two same or different C1-C6 alkyl, e.g. $-CONHMe$, $-CONHEt$, $-CON(Me)Et$, $-CONEt_2$ or $-CONMe_2$ etc.;

C1-C6 alkyl-substituted sulfoamido means the hydrogen of the sulfoamido is substitueted by one or two same or different C1-C6 alkyl, e.g. $-SO_2NHMe$, or $-SO_2NHEt$ etc.;

Hydroxy-C1-C6 alkyl means a carbon atom of a linear or branched alkyl containing 1-6 carbon atoms is connected with a hydroxy, such as $-CH_2OH$, $-CH_2CH_2OH$, $-CH(OH)CH_3$, $-CH_2CH_2CH_2OH$, $-CH_2CH_2CH_2CH_2OH$ or $-CH_2CH(CH_3)CH_2OH$ and the like;

Amino-C1-C6 alkyl means a carbon atom of a linear or branched alkyl containing 1-6 carbon atoms is connected with an amino group, such as $-CH_2NH_2$, $-CH_2CH_2NH_2$, $-CH(NH_2)CH_3$, $-CH_2CH_2CH_2NH_2$ or $-CH_2CH_2CH_2CH_2NH_2$ and the like;

C1-C6 alkyl-substituted amino-C1-C6 alkyl means the hydrogen atom of the amino group is substituted by 1 or 2 same or different C1-C6 alkyl group, e.g. $-CH_2NHMe$ or $-CH_2CH_2NEt_2$ etc.

Carbamoyl-C1-C6 alkyl means the carbon atom of a linear or branched alkyl containing 1-6 carbon atoms is connected with a carbonyl carbon of carbamoyl group, e.g. $-CH_2CONH_2$, $-CH_2CH_2CONH_2$, $-CH(CONH_2)CH_3$ or $-CH_2CH_2CH_2CONH_2$ etc.;

C1-C6 alkyl-substituted carbamoyl-C1-C6 alkyl means the hydrogen atom of the amino of the carbamoyl-C1-C6 alkyl is substituted with 1 or 2 same or different C1-C6 alkyl, for example $-CH_2CONHMe$, $-CH_2CH_2CONHEt$, $-CH_2CH_2CONMe2$ or $-CH_2CONEt_2$ and the like;

Cyano-C1-C6 alkyl means that a carbon atom of a linear or branched alkyl containing 1-6 carbon atom is connected to cyano, such as cyanomethyl ($-CH_2CN$), 2-cyanoethyl, 1-cyanoethyl, 3-cyanopropyl, 4-cyanobutyl or 5-cyanopentyl, etc.;

Carboxyl-C1-C6 alkyl means a carbon atom of a linear or branched alkyl containing 1-6 carbon atom is connected to a carboxyl, such as carboxymethyl ($-CH_2COOH$), 2-carboxyethyl, 1-carboxyethyl, 3-carboxypropyl, 4-carboxybutyl or 5-carboxypentyl, etc.;

C1-C6 alkyl sulfonyl means a linear or branched alkyl sulfonyl containing 1-6 carbon atoms, such as methyl sulfonyl, ethyl sunny' or propyl sulfonyl and the like;

Halo-C1-C6 alkyl sulfonyl means the hydrogen atom of a linear or branched alkyl sulfonyl containing 1-6 carbon atoms is substituted with one or more identical or different halogen atoms, such as trifluoromethyl sulfonyl;

C1-C6 alkyl substituted amino means the hydrogen atom of the amino is substituted by 1 or 2 same or different C1-C6 alkyl, such as $-NHMe$ or $-NEt_2$ and the like;

C1-C6 alkanoyl substituted amino means the hydrogen atom of the amino is substituted by 1 or 2 same or different C1-C6 alkanoyl, such as $-NHCOMe$, or $-NHCOEt$ and the like;

C1-C6 alkylsulfonyl substituted amino means the hydrogen atom of the amino is substituted by 1 or 2 same or different C1-C6 alkylsulfonyl, such as —NHSO$_2$Me, or —NHSO$_2$Et and the like;

C3-C6 cycloalkyl means a saturated cyclic hydrocarbon group containing 3-6 carbon atoms, such as cyclopropyl, cyclobutyl, cyclopentyl, cyclohexyl, etc.;

C3-C6 cycloalkoxy means a saturated cyclic hydrocarbonyloxy containing 3-6 carbon atoms, such as cyclopropoxy, cyclobutoxy, cyclopentoxy, cyclohexoxy and the like.

The compound of the present invention has the following beneficial effects:

1) The compounds of the present invention have good activity on dopamine D$_1$ receptor and/or dopamine D$_2$ receptor; antagonism IC$_{50}$ of some compounds against dopamine D$_1$ receptor or dopamine D$_2$ receptor even reach a level of 1-10 nM. The compounds of the invention also have a certain activity on the 5-HT receptor.

2) Some compounds of the present invention have both effects of dopamine D$_2$ receptor agonism and antagonism, which is D$_2$ receptor modulators, and can be better used for treating central nervous system diseases related to dopamine D$_2$ receptor.

3) The compound of the present invention does not contain a phenolic hydroxyl, has good solubility, good physical and chemical properties, good metabolic properties, high oral bioavailability, and long-lasting efficacy.

4) The compounds of the present invention are not only highly active, but also orally effective, with low pharmacological dosage and low toxic and side effects. They can be used to treat central nervous system diseases related to dopamine receptors, such as Parkinson's disease, schizophrenia, bipolar disorder, depression, anxiety, mania, ADHD, drug addiction or migraine and have good clinical application prospects.

DETAILED DESCRIPTION OF EXEMPLARY EMBODIMENTS

EXAMPLE 1

Figure 1:
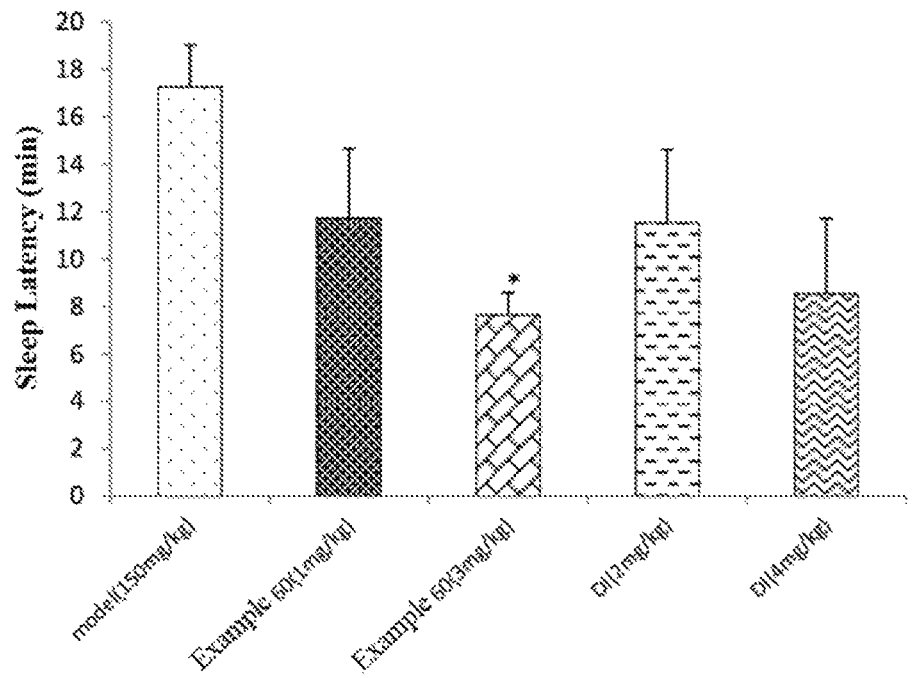
FIG. 1 is a bar graph of the effect of a single-dose administration of Example 60 on the sleep latency of PCPA-induced insomnia model in rats treated with sodium pentobarbital (*P<0.05 vs model group)

(S)-2-methyl-3,9,10-trimethoxy-6,8,13,13a-tetrahydro-5H-dibenzo[a,g] quinolizine (Class I-A)

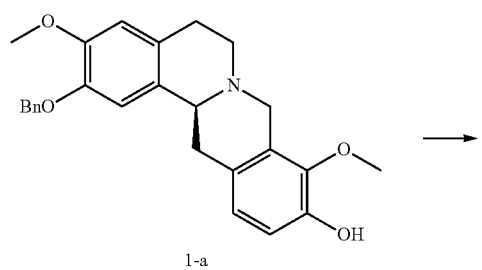

1-a

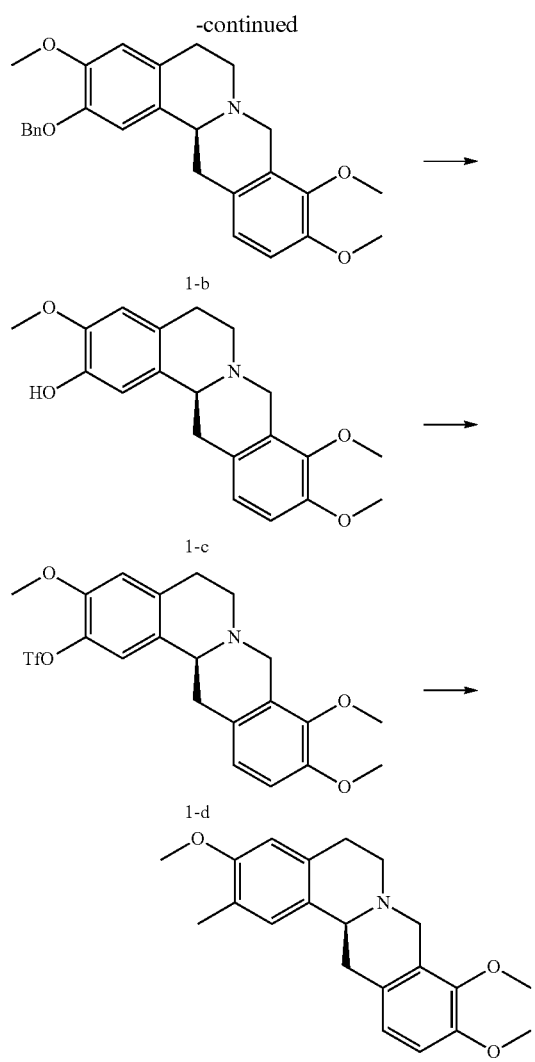

The preparation of compound 1-a can be referred to the previous patent CN102399166B of the same applicant.

Step 1:

The 1-a (300 mg, 0.72 mmol) was dissolved in DMF (4 mL). Thereto, dimethyl sulfate (0.07 mL, 0.72 mmol), sodium hydride (69 mg, 2.88 mmol) were added. The reaction was performed for 6 h while stirring. The resultant was extracted with dichloromethane, and washed with a saturated ammonium chloride solution. The organic phase was combined, washed with saturated brine, dried over anhydrous sodium sulfate, concentrated, and subjected to silica gel column chromatography to obtain 1-b (60 mg, yield: 19%), $^1$H-NMR (300 Hz, CDCl$_3$) δ 2.53-2.79 (m, 3H), 3.03-3.23 (m, 3H), 3.42-3.56 (m, 2H), 3.84 (s, 6H), 3.87 (s, 3H), 4.22 (d, 1H), 5.14 (s, 2H), 6.64 (s, 1H), 6.74 (s, 1H), 6.81 (m, 2H), 7.29-7.49 (m, 5H). ESI-MS m/z 432.3 (M+H)$^+$.

Step 2:

The 1-b (60 mg, 0.14 mmol) was dissolved in ethyl acetate (2 mL). Thereto, the palladium on carbon (10 mg) was added. The hydrogenation reaction was carried out for 10 h. The mixture was filtered, and the mother liquor was concentrated. The resultant was slurried in petroleum ether, filtered to obtain 1-c (12 mg, yield: 25%). $^1$H-NMR (300 Hz, CDCl$_3$) δ 2.57-2.71 (m, 2H), 2.80 (dd, 1H), 3.07-3.29 (m, 3H), 3.47-3.57 (d, 2H), 3.84 (s, 6H), 3.87 (s, 3H), 4.24 (d, 1H), 6.59 (s, 1H), 6.78 (d, 1H), 6.81 (s, 1H), 6.87 (d, 1H). ESI-MS m/z 342.33 (M+H)+.

Step 3:

Dichloromethane (5 ml) and triethylamine (0.82 ml, 5.8 mmol) were added into 1-c (1 g, 2.9 mmol) and then Tf$_2$O (0.58 ml, 3.48 mmol) was slowly added dropwise under an ice bath. After completion of addition, the mixture was stirred for 3 h at room temperature. The resultant was extracted with dichloromethane-water, washed with saturated brine, dried over anhydrous sodium sulfate, concentrated, and subjected to column chromatography to obtain 1-d (0.8 g, yield: 57%).

Step 4:

1-d (150 mg, 0.317 mmol) was placed in a three-necked flask, and methylboronic acid (76 mg, 1.27 mmol), potassium carbonate (175 mg, 1.27 mmol), and tetrakis (triphenylphosphonium) palladium (79 mg, 0.063 mmol) and 1,4-dioxane (3 mL) were added thereto. The mixture was refluxed at 100° C. overnight under a nitrogen atmosphere. The resulting reaction solution was filtered, and the filtrate was concentrated and subjected to column chromatography to obtain the title compound (10 mg, yield: 9%). $^1$H NMR (300 MHz, CDCl$_3$) δ 2.20 (s, 3H), 2.57-2.86 (m, 3H), 3.11-3.34 (n, 3H), 3.48-3.58 (m, 2H), 3.81 (s, 3H), 3.84 (s, 6H), 4.24 (d, 1H), 6.56 (s, 1H), 6.78 (d, 1H), 6.87 (d, 1H), 7.01 (s, 1H). ESI-MS m/z 340.1 (M+H)+.

EXAMPLE 2

(S)-2-n-propyl-3,9,10-trimethoxy-6,8,13,13a-tetra-hydro-5H-dibenzo [a,g] quinolizine (Class I-A)

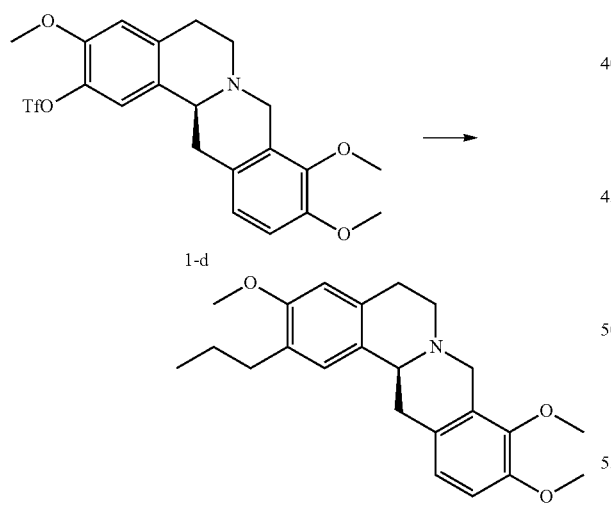

The title compound was prepared from 1-d and propylboronic acid, with reference to the method for synthesizing the product of Example 1. That is, methylboronic acid (76 mg, 1.27 mmol) was replaced with propylboronic acid (111.6 mg, 1.27 mmol). The yield was 25%. $^1$ H NMR (300 MHz, CDCl$_3$) δ 0.96 (t, 3H), 1.54-1.65 (m, 2H), 2.52-2.90 (m, 5H), 3.11-3.35 (m, 3H), 3.49-3.63 (m, 2H), 3.80 (s, 3H), 3.85 (s, 6H), 4.27 (d, 1H), 6.58 (s, 1H), 6.79 (d, 1H), 6.88 (d, 1H), 7.00 (s, 1H). ESI-MS m/z 368.2 (M+H)+.

EXAMPLE 3

(S)-2-isobutyl-3,9,10-trimethoxy-6,8,13,13a-tetra-hydro-5H-dibenzo [a,g] quinolizine (Class I-A)

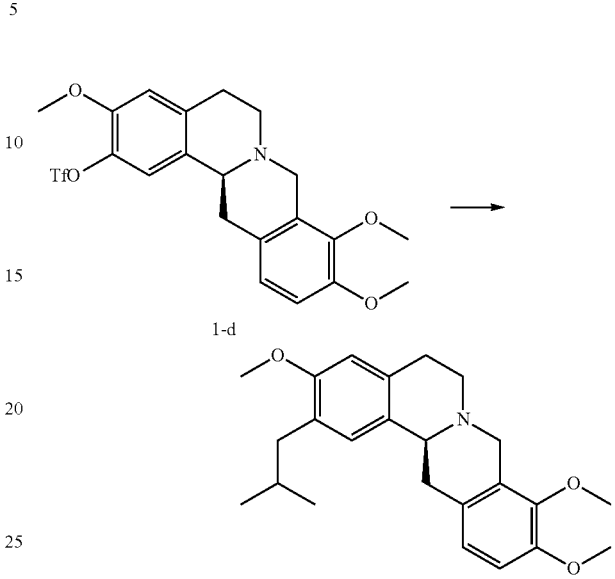

The title compound was prepared from 1-d and isobutyl-boronic acid, with reference to the method for synthesizing the product of Example 1. That is, methylboronic acid (76 mg, 1.27 mmol) was replaced with isobutylboronic acid (129.5 mg, 1.27 mmol). The yield was 28%. ESI-MS m/z 382.29 (M+H)+.

EXAMPLE 4

(S)-2-cyano-3,9,10-trimethoxy-6,8,13,13a-tetra-hydro-5H-dibenzo [a,g] quinolizine (Class I-A)

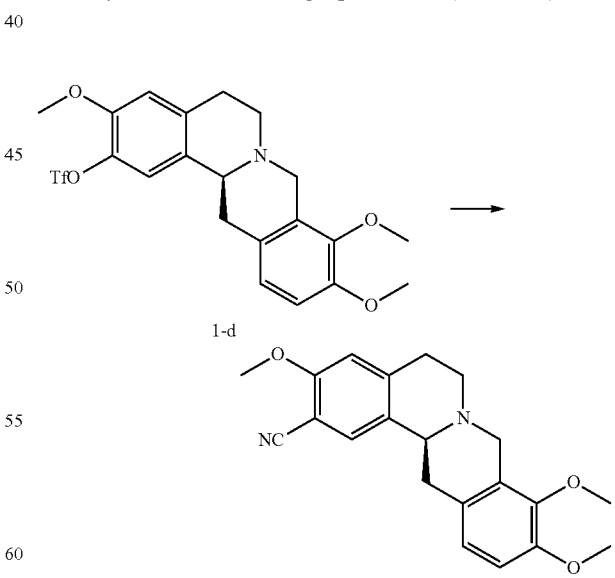

DMAc (15 ml), zinc cyanide (328 mg, 2.78 mmol), zinc powder (28 mg, 0.41 mmol), DPPF (155 mg, 0.27 mmol) and Pd$_2$(dba)$_3$ (80 mg, 0.13 mmol) were added into 1-d (660 mg, 1.39 mmol). The mixture was heated at 160° C. overnight. DMAc was concentrated, and the resultant was extracted with dichloromethane-water, washed with saturated brine, dried, concentrated, and subjected to column chromatography to obtain the title compound. (450 mg. yield: 92%). ¹H NMR (300 MHz, DMSO-d₆) δ 2.42-2.62(m, 2H), 2.81(d, 1H), 2.97-3.20(m, 2H), 3.35-3.50(m, 3H), 3.72(s, 3H), 3.77(s, 3H), 3.88(s, 3H), 4.07(d, 1.H), 6.87(two d peaks), 7.01 (s, 1H) , 7.74(s, 1H). ESI-MS m/z 350.7 (M+H)⁺.

EXAMPLE 5

(S)-2-carbamoyl-3,9,10-trimethoxy-6,8,13,13a-tetrahydro-5H-dibenzo [a,g] quinolizine (Class I-A)

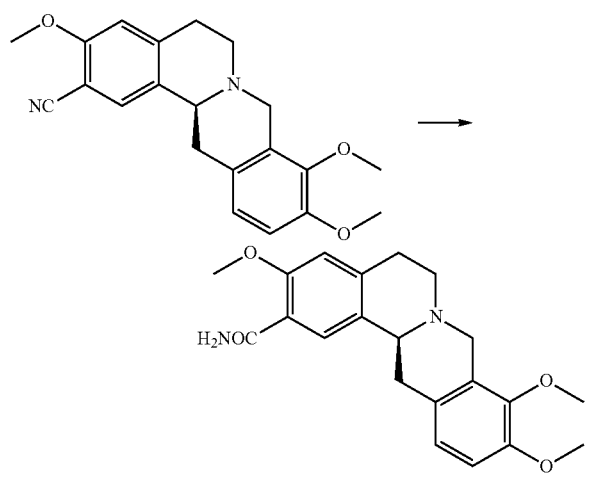

DMSO (3 ml), hydrogen peroxide (3 ml) and sodium hydroxide (75 mg, 1.82 mmol) were added into the product of Example 4 (320 mg, 0.91 mmol). The mixture was heated at 70° C. for 2 h. The saturated ammonium chloride solution was used to adjust the pH of the mixture to alkalescency. The resulting mixture was extracted with dichloromethane-water, washed with saturated brine, dried, concentrated, and subjected to column chromatography to obtain the title compound (130 mg, yield: 38%). ¹H NMR (300 MHz, CD₃OD) δ 2.59-2.95(m, 3H), 3.11-3.29(m, 2H), 3.40-3.61 (m, 3H), 3.81(s, 3H), 3.82(s, 3H), 3.95(s, 3H), 4.21(d, 1H), 6.91(m, 3H), 7.97(s, 1H). ESI-MS m/z 369.1 (M+H)⁺.

EXAMPLE 6

(S)-2-formyl-3,9,10-trimethoxy-6,8,13,13a-tetrahydro-5H-dibenzo[a,g] quinolizine (Class I-A)

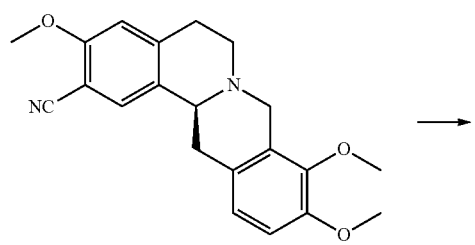

-continued

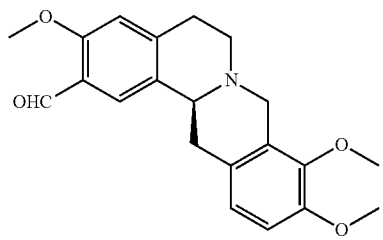

Dichloromethane (2 ml) was added into the product of Example 4 (500 mg, 1.42 mmol), and then DIBAL (2.8 ml) was added under an ice bath. The reaction was kept under an ice bath for 3 h. 1M hydrochloric acid was used to adjust the pH of the mixture to around 5. The resulting mixture was extracted with dichloromethane-water, washed with saturated brine, dried, concentrated, and subjected to column chromatography to obtain the title compound (390 mg, yield: 77%). ¹H NMR (300 MHz, DMSO-d₆) δ 2.59-2.87 (m, 3H), 3.17-3.28 (m, 2H), 3.39 (dd, 1H), 3.48-3.61 (m, 2H), 3.85 (s, 6H), 3.92 (s, 3H), 6.73 (s, 1H), 6.79 (d, 1H), 6.88 (d, 1H), 7.75 (s, 1H), 10.42 (s, 1H).

EXAMPLE 7

(S)-2-hydroxymethyl-3,9,10-trimethoxy-6,8,13,13a-tetrahydro-5H-dibenzo[a,g] quinolizine (Class I-A)

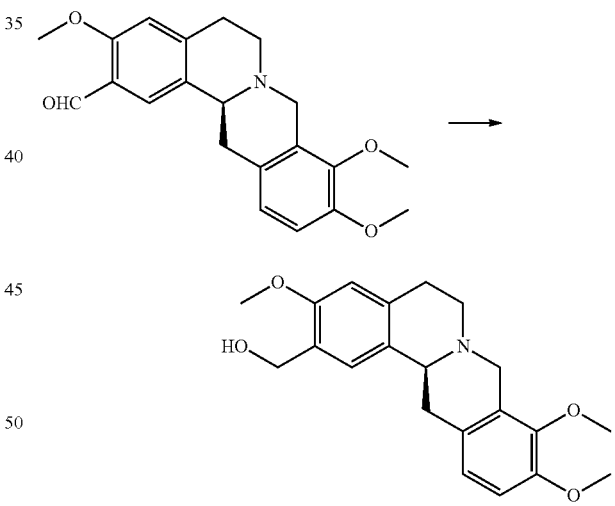

Methanol (3 ml) and sodium borohydride (84 mg) were added into the product of Example 6 (390 mg, 1.10 mmol). The mixture was stirred at room temperature for 30 min. Methanol was concentrated, and the resulting mixture was extracted with dichloromethane-water, washed with saturated brine, dried, concentrated, and subjected to column chromatography to obtain the title compound (210 mg, yield: 53%). ¹H NMR (300 MHz, DMSO-d₆) δ 2.41-2.75 (m, 3H), 2.91-3.17 (m, 2H), 3.24-3.47 (m, 3H), 3.72 (s, 3H), 3.74 (s, 3H), 3.77 (s, 3H), 4.07 (d, 1H), 4.45 (d, 1H), 4.94 (t, 1H), 6.67 (s, 1H), 6.88 (s, 2H), 7.28 (s,1H), ESI-MS m/z 355.6 (M+H)⁺.

EXAMPLE 8

(S)-2-carboxy-3,9,10-trimethoxy-6,8,13,13a-tetrahydro-5H-dibenzo [a,g] quinolizine (class I-A)

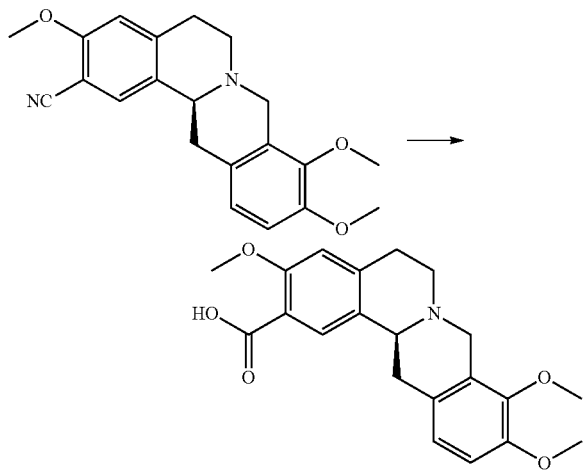

30% hydrogen peroxide solution (10 ml), 10M sodium hydroxide solution (5 ml) and ethanol (5 ml) were added into the product of Example 4 (400 mg, 1.14 mmol). The mixture was heated to reflux for 72 h. Most parts of the solvent were distilled off, and the concentrated hydrochloric acid was used to adjust the pH of the mixture to subacidity. The resulting mixture was extracted with dichloromethane-water, washed with saturated brine, dried, concentrated, and subjected to column chromatography to obtain the title compound (150 mg, yield: 35%). $^1$H NMR (300 MHz, CDCl$_3$) δ 2.59-2.89 (m, 3H), 3.17-3.32 (m, 2H), 3.42 (dd, 1H), 3.50-3.63 (m, 2H), 3.85 (s, 6H), 4.07 (s, 3H), 4.26 (d, 1H), 6.77-6.83 (m, 2H), 6.88 (d, 1H), 8.10 (s, 1H). ESI-MS m/z 369.5 (M+H)$^+$, 367.8 (M−H)$^−$.

EXAMPLE 9

(S)-2-ethoxycarbonyl-3,9,10-trimethoxy-6,8,13,13a-tetrahydro-5H-dibenzo[a,g] quinolizine (Class I-A)

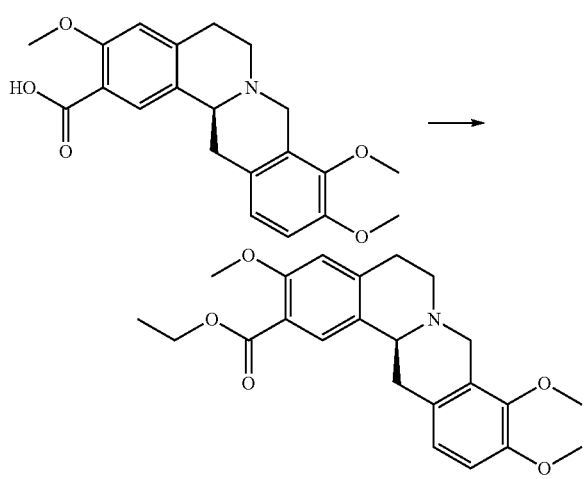

Ethanol (3 ml) was added into the product of Example 8 (137 mg, 0.37 mmol), and sulfoxide chloride (0.08 ml, 1.11 mmol) was added at room temperature. The mixture was heated to reflux for 2 h. The solvents were distilled off. The resulting mixture was extracted with dichloromethane-saturated sodium bicarbonate solution, washed with saturated brine, dried, concentrated, and subjected to column chromatography to obtain the title compound (50 mg, yield: 34%). $^1$H NMR (300 MHz, CDCl$_3$) δ 1.39 (t, 3H), 2.57-2.87 (m, 3H), 3.14-3.27 (m, 2H), 3.33 (dd, 1H), 3.48-3.60 (m, 2H), 3.85 (s, 6H), 3.88 (s, 3H), 4.24 (d, 1H), 4.36 (q, 2H), 6.71 (s, 1H), 6.78 (d, 1H), 6.89 (d, 1H), 7.71 (s, 1H). ESI-MS m/z 398.1 (M+H)$^+$.

EXAMPLE 10

(S)-2-aminomethyl-3,9,10-trimethoxy-6,8,13,13a-tetrahydro-5H-dibenzo[a,g] quinolizine (Class I-A)

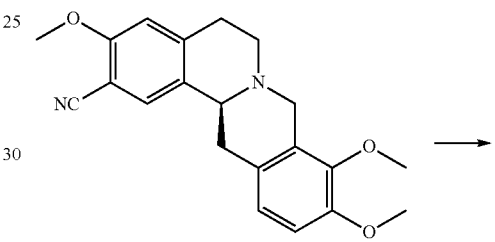

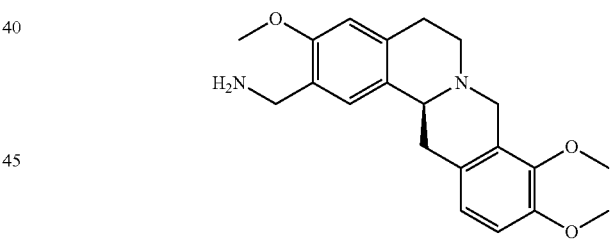

THF (2 ml) and borane-tetrahydrofuran solution (1.2 ml) were added into the product of Example 4 (150 mg, 0.42 mmol). The mixture was heated to reflux overnight, 1M hydrochloric acid was added thereto to adjust pH to around 2. The mixture was heated at 100° C. for 1 h. The sodium bicarbonate solution was used to adjust the pH of the mixture to alkalescency. The resulting mixture was extracted with dichloromethane-water, dried, concentrated, and subjected to column chromatography to obtain the title compound (50 mg, yield: 33%). $^1$H NMR (300 MHz, DMSO-d$_6$) δ 2.98 (d, 1H), 3.26 (t, 1H), 3.69-4.04 (m, 13H), 4.24-4.79 (m, 3H), 6.96 (s, 1H), 6.97 (d, 1H), 7.08 (d, 1H), 7.63 (s, 1H), 8.42 (brs, 2H), 12.08 (s, 1H). ESI-MS m/z 355.0 (M+H)$^+$.

EXAMPLE 11

(S)-2-acetaminomethyl-3,9,10-trimethoxy-6,8,13,13a-tetrahydro-5H-dibenzo[a,g] quinolizine (type IA)

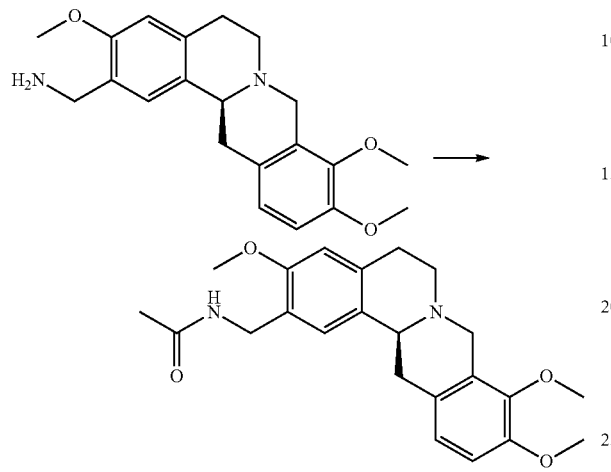

Dichloromethane (1.5 ml), triethylamine (0.09 ml, 0.63 mmol) and acetic anhydride (0.04 ml, 0.42 mmol) were added into the product of Example 10 (75 mg, 0.21 mmol). The mixture was stirred at room temperature for 1 h. The resulting mixture was extracted with dichloromethane-water, dried, concentrated, and subjected to column chromatography to obtain the title compound (20 mg, yield: 24%). $^1$H NMR (300 MHz, CDCl$_3$) δ 1.97 (s, 3H), 2.56-2.85 (m, 3H), 3.12-3.37 (m, 3H), 3.47-3.59 (m, 2H), 3.85 (s, 9H), 4.24 (d, 1H), 4.41 (d, 2H), 6.01 (brs, 1H), 6.62. (s, 1H), 6.79 (d, 1H), 6.88 (d, 1H), 7.17 (s, 1H), ESI-MS m/z 397.0 (M+H)$^+$.

EXAMPLE 12

(S)-2-acetyl-3,9,10-trimethoxy-6,8,13,13a-tetrahydro-5H-dibenzo [a,g] quinolizine (Class I-A)

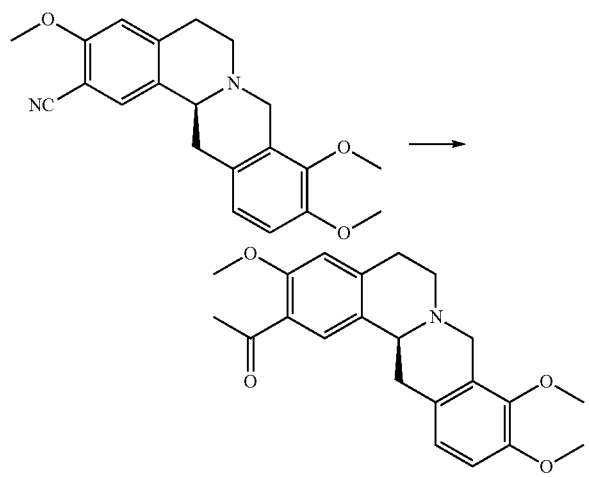

1M methyl magnesium bromide (5 ml) was added into the product of Example 4 (250 mg, 0.71 mmol). The mixture was heated to reflux overnight. The resulting mixture was extracted with dichloromethane-water, washed with saturated brine, dried, concentrated, and subjected to column chromatography to obtain the title compound (20 mg, yield: 7%). $^1$H NMR (300 MHz, CDCl$_3$) δ 2.57-2.86 (m, 3H), 2.62 (s, 3H), 3.15-3.31 (m, 3H), 3.39 (dd, 1H), 3.48-3.62 (m, 2H), 3.85 (s, 6H), 3.90 (s, 3H), 4.26 (d, 1H), 6.71 (s, 1H), 6.79 (d, 1H), 6.88 (d, 1H), 7.70 (s, 1H). ESI-MS m/z 368.2 (M+H)$^+$.

EXAMPLE 13

(S)-2-amino-3,9,10-trimethoxy-6,8,13,13a-tetrahydro-5H-dibenzo [a,g] quinolizine hydrochloride (Class I-A)

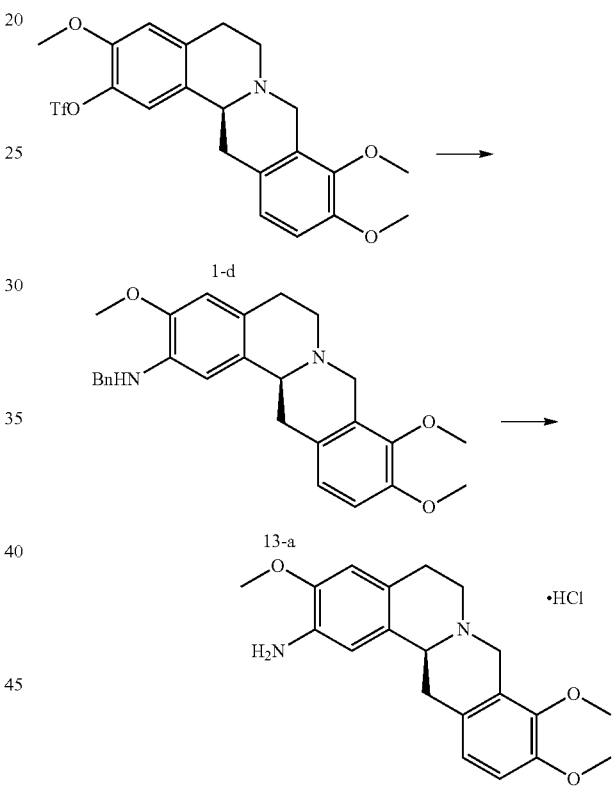

Step 1:

1-d (2 g, 4.22 mmol) was place in a double-necked flask. Thereto, cesium carbonate (3.4 g. 10.5 mmol), palladium acetate (189 mg, 0.84 mmol), BINAP (789 mg, 1.26 mmol), and toluene (15 ml) were added. After completion of nitrogen replacement for 15 min, benzylamine (0.92 ml, 8.44 mmol) was added thereto. The reaction was performed at 110° C. overnight. Toluene was concentrated. Dichloromethane was added to dissolve the product. The insoluble matter was removed by filtration. The filtrate was extracted with dichloromethane-water, washed with saturated brine, dried, concentrated, and subjected to column chromatography to obtain 13-a (400 mg, yield: 22%). ESI-MS m/z 430.8 (M+H)$^+$.

Step 2:

Methanol (5 ml), palladium on carbon (40 mg) and ammonium formate (293 mg, 4.65 mmol) were added into 13-a (400 mg, 0.93 mmol). The mixture was heated to reflux for 2 h. The palladium on carbon was filtered off, and the methanol was distilled off. The resulting mixture was extracted with dichloromethane-water, washed. with saturated brine, dried, concentrated, and subjected to column chromatography to obtain oily product. HCl-EtOH was added thereto to form a salt so as to obtain the title compound as a yellow solid (225 mg, yield: 64%). $^1$H NMR (300 MHz, DMSO-$d_6$) δ 2.98 (d, 1H), 3.17 (t, 1H), 3.48 (m, 2H), 3.69-3.96 (m, 11H), 4.38 (d, 1H), 4.62 (d, 1H), 4.75 (d, 1H), 6.94-7.15 (m, 3H), 7.45 (s, 1H), 9.75 (brs, 2H), 11.99 (s, 1H). ESI-MS m/z 341.3 (M+H)$^+$.

EXAMPLE 14

(S)-2-acetamido-3,9,10-trimethoxy-6,8,13, 13a4tetrahydro-5H-dibenzo[a,g] quinolizine hydrochloride (Class I-A)

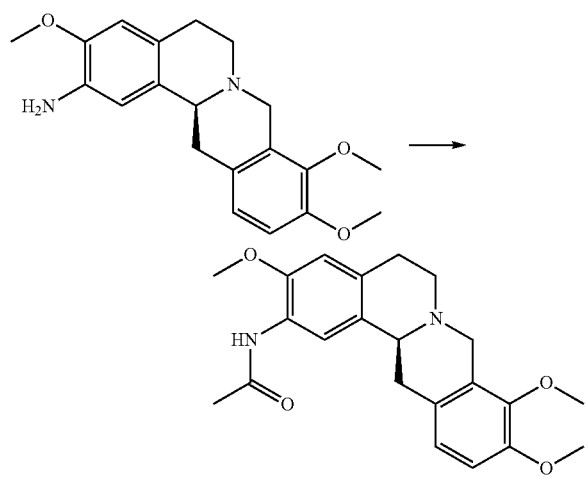

The title compound was prepared from the product of Example 13 and acetic anhydride, with reference to the method for synthesizing the product of Example 11. That is, the product of Example 10 (75 mg, 0.21 mmol) was replaced with the product of Example 13 (72 mg, 0.21 mmol). The yield was 38%. $^1$H NMR (300 MHz, CDCl$_3$) δ 2.19 (s, 3H), 2.61-2.93 (m, 3H), 3.15-3.31 (m, 2H), 3.39 (dd, 1H), 3.51-3.69 (m, 2H), 3.83 (s, 6H), 3.86 (s, 3H), 6.60 (s, 1H), 6.78 (d, 1H), 6.87 (d, 1H), 7.72 (brs, 1H), 8.32 (s, ESI-MS m/z 383.1 (M+H)$^+$.

EXAMPLE 15

(S)-2-bromo-3,9,10-tritmethoxy-6,8,13,13a-tetrahydro-5H-dibenzo [a,g] quinolizine (Class I-A)

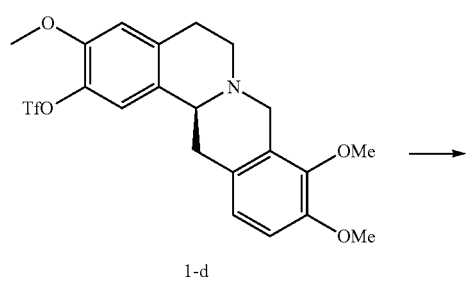

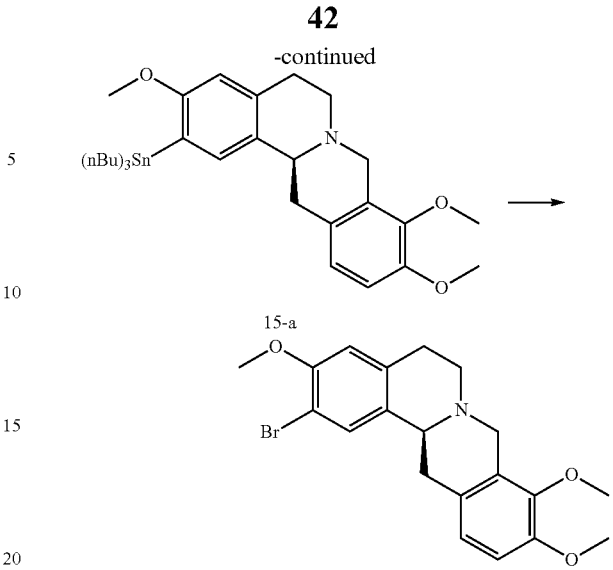

Step 1:
Lithium chloride (135 mg, 3.15 mmol), tetrakis(triphenylphosphine)palladium (80 mg, 0.063 mmol), hexabutylditin (0.65 ml, 1.26 mmol) and 1,4-dioxane (2 ml) were added into 1-d (300 mg, 0.63 mmol). The mixture was heated to reflux overnight after nitrogen replacement. The solvent was distilled off. The resulting mixture was extracted with dichloromethane-water, dried, concentrated, and subjected to column chromatography to obtain 15-a (132 mg, yield: 33%). ESI-MS m/z 615.4. (M+H)$^+$.

Step 2:
Dichloromethane (3 ml) was added into 15-a (110 mg, 0.17 mmol), and then NBS (40 mg, 0.22 mmol) was added under an ice bath. The mixture was stirred for 5 min. Dichloromethane and water were added for extraction, and the mixture was washed with saturated brine, dried, and concentrated and subjected to column chromatography to obtain the title compound (56 mg, yield: 77%). $^1$H NMR (300 MHz, CDCl$_3$) δ 2.56-2.87 (m, 3H), 3.09-3.31 (m, 3H), 3.48-3.58 (m, 2H), 3.85 (s, 6H), 3.88 (s, 3H), 4.24 (d, 1H), 6.65 (s, 1H) (d, 1H), 6.88 (d, 1H), 7.42 (s, 1H). ESI-MS m/z 403.6 (M+H)$^+$.

EXAMPLE 16

(S)-2-chloro-3,9,10-trimethoxy-6,8,13,13a-tetrahydro-5H-dibenzo [a,g] quinolizine (Class I-A)

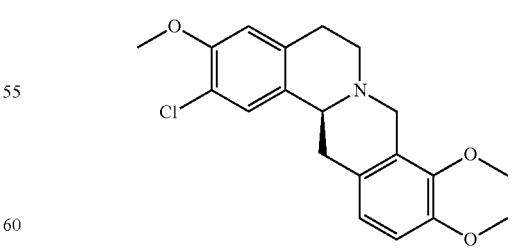

The title compound was prepared by reacting 15-a with NCS, with reference to the method for synthesizing the product of Example 15. That is, NBS (40 mg, 0.22 mmol) was replaced with NCS (29 mg, 0.22 mmol). The yield was 35%. ESI-MS m/z 360.7 (M+H)$^+$.

EXAMPLE 17

(S)-2-vinyl-3,9,10-trimethoxy-6,8,13,13a-tetrahydro-5H-dibenzo [a,g] quinolizine (class I-A)

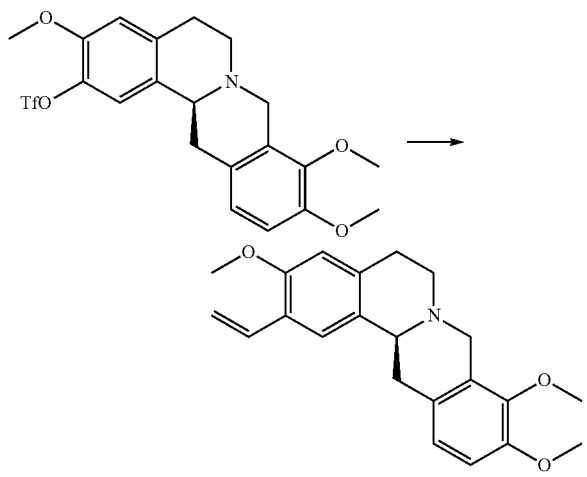

Dry DMF (15 ml), lithium chloride (270 mg, 5.07 mmol), bis(triphenylphosphine)palladium dichloride (25 mg, 0.03 mmol) and tributylvinyltin (0.6 ml, 2.02 mmol) were added into 1-d (800 mg, 1.69 mmol). The mixture was heated to reflux overnight after nitrogen replacement. DMF was distilled off. The resultant was extracted with dichloromethane-water, dried, concentrated, and subjected to column chromatography to obtain the title compound (275 mg, yield: 46%). $^1$H NMR (300 MHz, CDCl$_3$) δ 2.62-2.92 (m, 3H), 3.15-3.29 (m, 2H), 3.35 (dd, 1H), 3.51-3.65 (m, 2H), 3.84 (s, 3H), 3.86 (s, 6H). 4.27 (d, 1H), 5.25 (d, 1H), 5.73 (d, 1H), 6.62 (s, 1H), 6.80 (d, 1H), 6.90 (d, 1H), 7.02 (dd, 1H), 7.34 (s,1H). ESI-MS m/z 352.0 (M+H)$^+$.

EXAMPLE 18

(S)-2-hydroxyethyl-3,9,10-trimethoxy-6,8,13,13a-tetrahydro-5H-dibenzo[a,g] quinolizine (Class I-A)

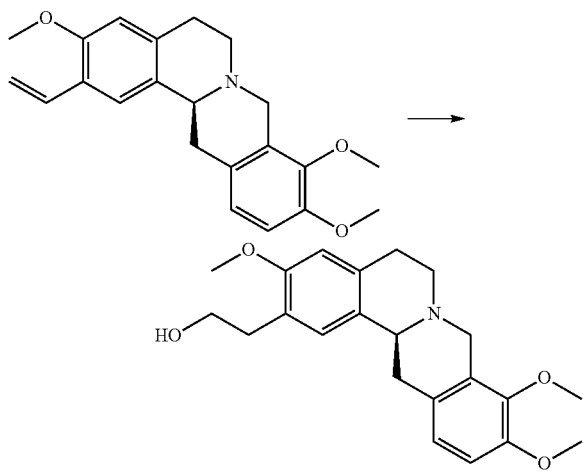

THF (1 ml) and a 1M borane-tetrahydrofuran solution (1.7 ml, 1.68 mmol) were added into the product of Example 17 (200 mg, 0.56 mmol). The mixture was stirred at room temperature overnight Water (2 ml), 1M sodium hydroxide solution (6 ml) and 30% hydrogen peroxide (1.2 ml) were added thereto. The mixture was heated at 65° C. for 2 h. The saturated ammonium chloride solution was used to adjust the pH of the mixture to alkalescency. The resulting mixture was extracted with dichloromethane-water, dried over anhydrous sodium sulfate, concentrated, and subjected to column chromatography to obtain the title compound (60 mg, yield: 28%). $^1$H NMR (300 MHz, CDCl$_3$) δ 2.58-2.93 (m, 5H), 3.12-3.36 (m, 3H), 3.49-3.60 (m, 2H), 3.83 (s, 3H), 3.86 (s, 6H), 3.80-3.88 (m, 2H), 4.25 (d, 1H), 6.62 (s, 1H), 6.80 (d, 1H), 6.89 (d, 1H), 7.05 (s, 1H). ESI-MS m/z 370.1 (M+H)$^+$.

EXAMPLE 19

(S)-2,3,10-trimethoxy-9-cyano-6,8,13,13a-tetrahydro-5H-dibenzo [a,g] quinolizine (Class I-C)

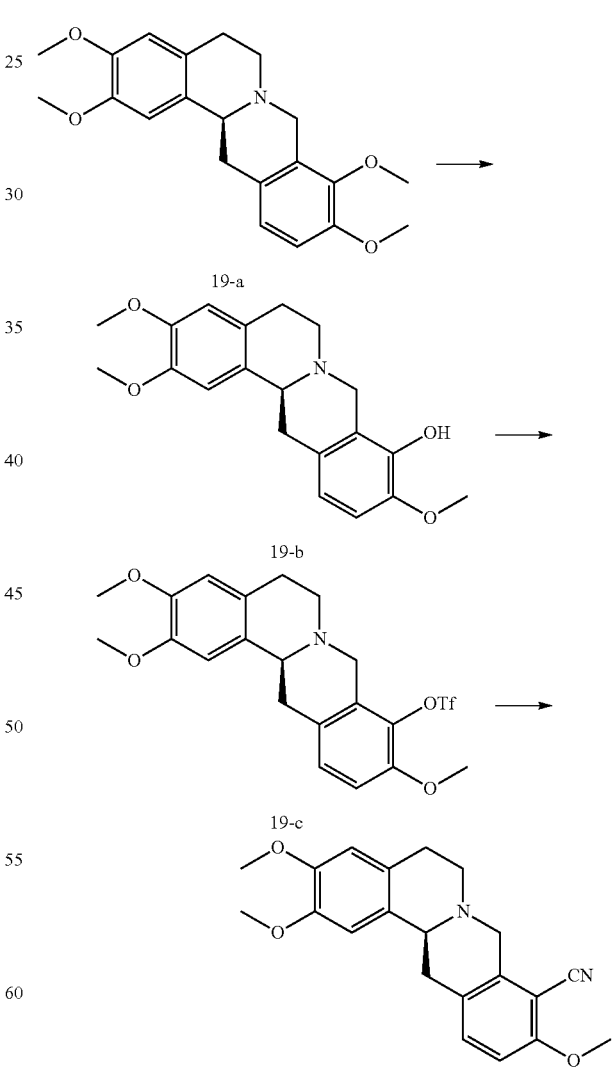

Step 1:
D-Tetrahydropalmatine 19-a (10 g, 28.1 mol) was dissolved in methanesulfonic acid (12 mL). Thereto, methionine (5 g, 30.9 mmol) was added. The reaction was performed at 30° C. for 3 h. The reaction solution was slowly added to the NaOH solution under an ice bath, and the pH of the mixture was adjusted to 13. The raw materials were filtered off with suction. The filtrate was extracted with dichloromethane several times. The organic phase was combined, and washed with water, brine, dried over anhydrous sodium sulfate, and concentrated. The crude product was subjected to recrystallization in methanol to give 19-b as a white solid (1.59 g, 16% yield). $^1$H NMR (300 MHz, CDCl$_3$) δ 2.58-2.72 (m, 2H), 2.83 (dd, 1H), 3.07-3.30 (m, 3H), 3.47-3.62 (m, 2H), 3.87 (s, 6H), 3.89 (s, 3H), 4.24 (d, 1H), 5.68 (s, 1H), 6.62 (s, 1H), 6.68 (d, 1H), 6.74 (m, 2H). ESI-MS m/z 342.3 (M+H)$^+$.

Step 2:

Dichloromethane (5 ml) and triethylamine (0.82 ml, 5.8 mmol) were added into 19-b (1 g, 2.9 mmol), and then Tf$_2$O (0.58 ml, 3.48 mmol) was slowly added dropwise under an ice bath. After completion of addition, the mixture was stirred for 3 h at room temperature. The resultant was extracted with dichloromethane-water, washed with saturated brine, dried over anhydrous sodium sulfate, concentrated, and subjected to column chromatography to obtain 19-c (0.8 g, yield: 57%).

Step 3:

The title compound was prepared from the 19-c via cyanation reaction, with reference to the method for synthesizing the product of Example 4. That is, 1-d (660 mg, 1.39 mmol) was replaced with 19-c (660 mg, 1.39 mmol). The yield was 50%, $^1$H NMR (300 MHz, CDCl$_3$) δ 2.60-2.73 (m, 2H), 2.82 (dd, 1H), 3.05-3.32 (m, 3H), 3.60 (dd, 1H), 3.73 (d, 1H), 3.87 (s, 3H), 3.88 (s, 3H), 3.92 (s, 3H), 6.63 (s, 1H), 6.70 (s, 1H), 6.81 (d, 1H), 7.33 (d, 1H). ESI-MS m/z 351.0 (M+H)$^+$.

EXAMPLE 20

(S)-2,3,10-trimethoxy-9-carbamoyl-6,8,13,13a-tetrahydro-5H-dibenzo[a,g] quinolizine (Class I-C)

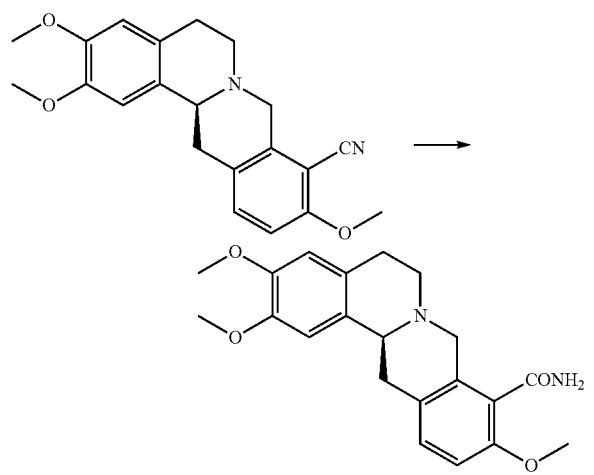

The title compound was prepared from the product of Example 19, with reference to the method for synthesizing the product of Example 5. That is, the product of Example 4 (320 mg, 0.91 mmol) was replaced with the product of Example 19 (320 mg, 0.91 mmol). The yield was 40%. $^1$H NMR (300 MHz, CDCl$_3$) δ 2.63 (m, 2H), 2.83 (dd, 1H), 3.10 (m, 2H), 3.30 (dd, 1H), 3.58 (dd, 1H), 3.85 (m, 10H), 4.13 (d, 1H), 5.86 (s, 1H), 6.08 (s, 1H), 6.60 (s, 1H), 6.72 (s, 1H), 6.80 (d, 1H), 7.17 (d, 1H). ESI-MS m/z 369.2 (M+H)$^+$.

EXAMPLE 21

(S)-2,3,10-trimethoxy-9-acetyl-6,8,13,13a-tetrahydro-5H-dibenzo [a,g] quinolizine (class I-C)

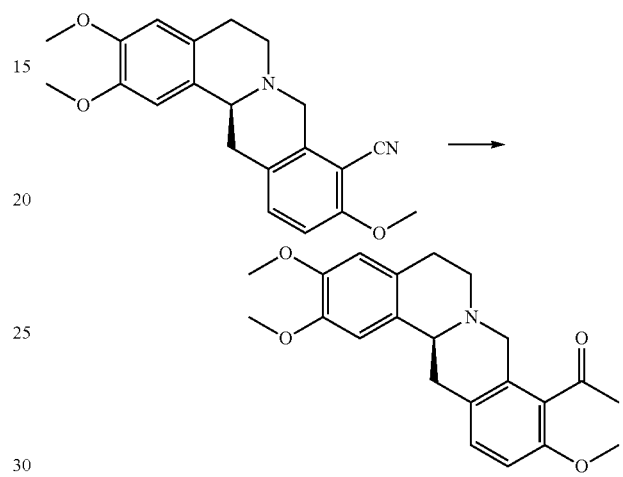

The title compound was prepared from the product of Example 19, with reference to the method for synthesizing the product of Example 12. That is, the product of Example 4 (250 mg, 0.71 mmol) was replaced with the product of Example 19 (250 mg, 0.71 mmol). The yield was 33%. $^1$H NMR (300 MHz, CDCl$_3$) δ 2.51 (s, 3H), 2.63 (m, 2H), 2.84 (dd, 1H), 3.11 (m, 2H), 3.30 (dd, 1H), 3.57 (dd, 1H), 3.68 (d, 1H), 3.85 (m, 10H), 6.60 (s, 1H), 6.72 (s, 1H), 6.80 (d, 1H), 7.16 (d, 1H). ESI-MS m/z 368.1 (M+H)$^+$.

EXAMPLE 22

(S)-2,3,10-trimethoxy-9-aminomethyl-6,8,13,13a-tetrahydro-5H-dibenzo[a,g] quinolizine (Class I-C)

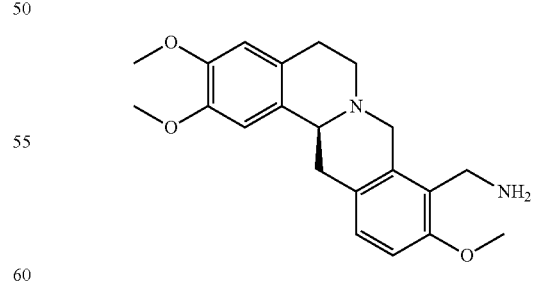

The title compound was prepared from the product of Example 19 via cyanation reduction, with reference to the method for synthesizing the product of Example 10. That is, the product of Example 4 (150 mg, 0.42 mmol) was replaced with the product of Example 19 (150 mg, 0.42 mmol). The yield was 50%

EXAMPLE 23

(S)-2,3,10-trimethoxy-9-acetylaminomethyl-6,8,13,13a-tetrahydro-5H-dibenzo[a,g] quinolizine (Class I-C)

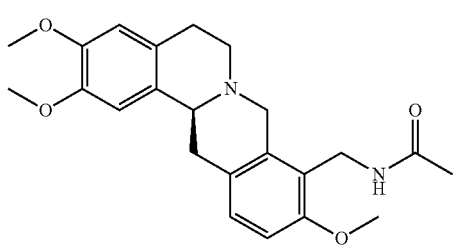 [SMILES: COc1cc2c(cc1OC)[C@@H]1Cc3ccc(OC)c(CNC(C)=O)c3CN1CC2]

The title compound was prepared from the product of Example 22 via acetylation, with reference to the method for synthesizing the product of Example 11. That is, the product of Example 10 (75 mg, 0.21 mmol) was replaced with the product of Example 22 (75 mg, 0.21) mmol). The yield was 80%. $^1$H NMR (300 MHz, CDCl$_3$) δ 1.93 (s, 3H), 2.64 (m, 2H), 2.84 (dd, 1H), 3.04-3.32 (m, 3H), 3.54 (d, 1H), 3.66 (d, H), 3.84 (s, 3H), 3.86 (s, 3H), 3.88 (s, 3H), 4.32 (d, 1H), 4.44 (m, 2H), 5.77 (t, 1H), 6.61 (s, 1H), 6.71 (s, 1H), 6.77 (d, H), 7.10 (d, 1H). ESI-MS m/z 397.1 (M+H)$^+$.

EXAMPLE 24

(S)-2,3,10-trimethoxy-9-formyl-6,8,13,13a-tetrahydro-5H-dibenzo [a,g] quinolizine (Class I-C)

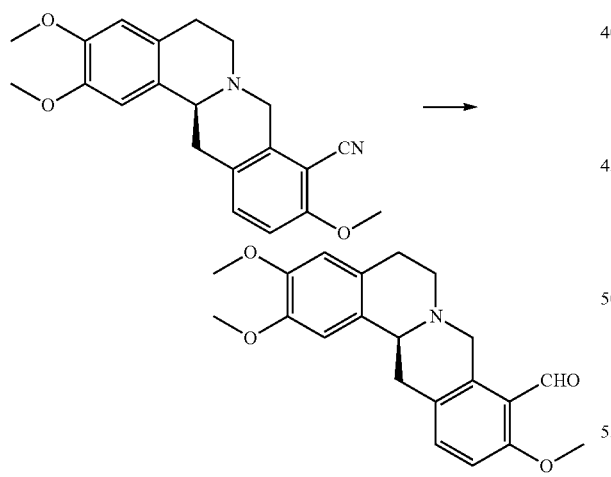

The title compound was prepared from the product of Example 19, with reference to the method for synthesizing the product of Example 6. That is, the product of Example 4 (500 mg, 1.42 mmol) was replaced with the product of Example 19 (500 mg, 1.42 mmol). The yield was 49%. $^1$H NMR (300 MHz, CDCl$_3$) δ 2.58-2.75 (m, 2H), 2.87 (t, 1H), 3.02-3.33 (m, 4H), 3.57 (d, 1H), 3.86 (s, 3H), 3.87 (5, 3H), 3.90 (s, 3H), 4.61 (d, 1H), 6.61 (s, 1H), 6.71 (s, 1H), 6.87 (d, 1H), 7.35 (d, 1H), 10.63 (s, 1H). ESI-MS m/z 354.3 (M+H)$^+$.

EXAMPLE 25

(S)-2,3,10-trimethoxy-9-hydroxymethyl-6,8,13,13a-tetrahydro-5H-dibenzo[a,g] quinolizine (Class I-C)

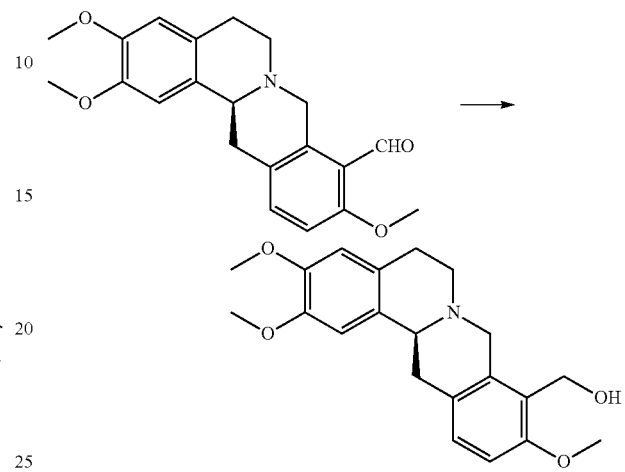

The title compound was prepared from the product of Example 24, with reference to the method for synthesizing the product of Example 7. That is, the product of Example 6 (390 mg, 1.10 mmol) was replaced with the product of Example 24 (390 mg, 1.10 mmol). The yield was 69%, $^1$H NMR (300 MHz, CD$_3$OD) δ 3.10 (t, 2H), 3.27 (m, 2H), 3.58 (td, 1H), 3.78-3.97 (m, 11H), 4.67 (m, 2H), 4.74-4.84 (m, 2H), 6.84 (s, 1H), 6.98 (s, 1H), 7.06 (d, H), 7.30 (d, 1H). ESL-MS m/z 356.1 (M+H)$^+$.

EXAMPLE 26

(S)-2,3,9-trimethoxy-10-methyl-6,8,13,13a-tetrahydro-5H-dibenzo [a,g] quinolizine (Class I-D)

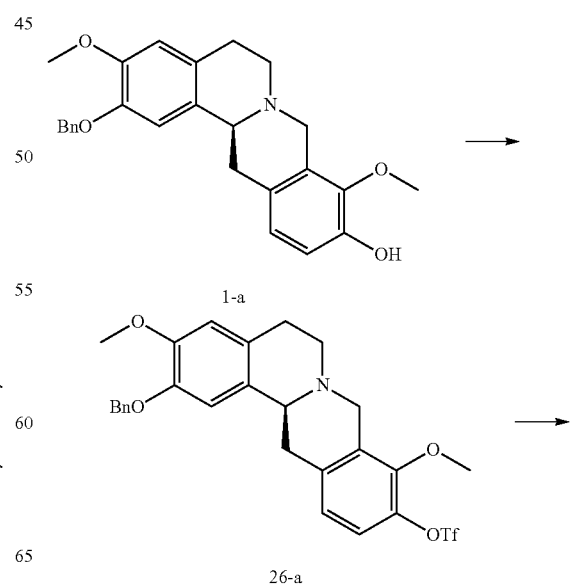

26-a

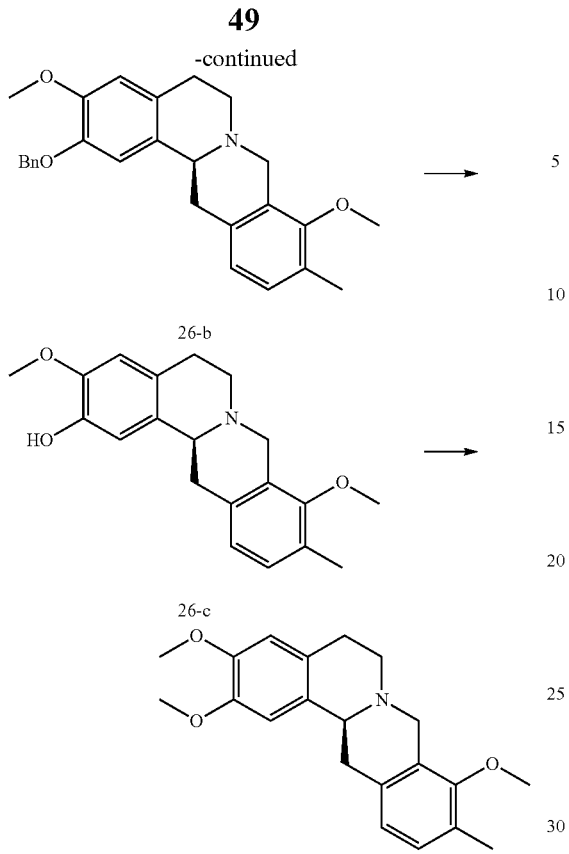

the method for synthesizing the compound 1-b. That is, 1-a was replaced with 26-c. The yield was 40%. $^1$H NMR (300 MHz, CDCl$_3$) δ 2.27 (s, 3H), 2.61-2.72 (m, 2H), 2.87 (dd, 1H), 3.11-3.25 (m, 2H), 3.29 (dd, 1H), 3.58 (d, 2H), 3.76 (s, 3H), 3.87 (s, 3H), 3.89 (s, 3H), 4.24 (d, 1H), 6.62 (s, 1H), 6.74 (s, 1H), 6.86 (d, 7.01 (d, ESI-MS m/z 340.3 (M+H)$^+$.

EXAMPLE 27

(S)-2,3,9-trimethoxy-10-cyano-6,8,13,13a-tetra-hydro-5H-dibenzo[a,g] quinolizine (Class I-D)

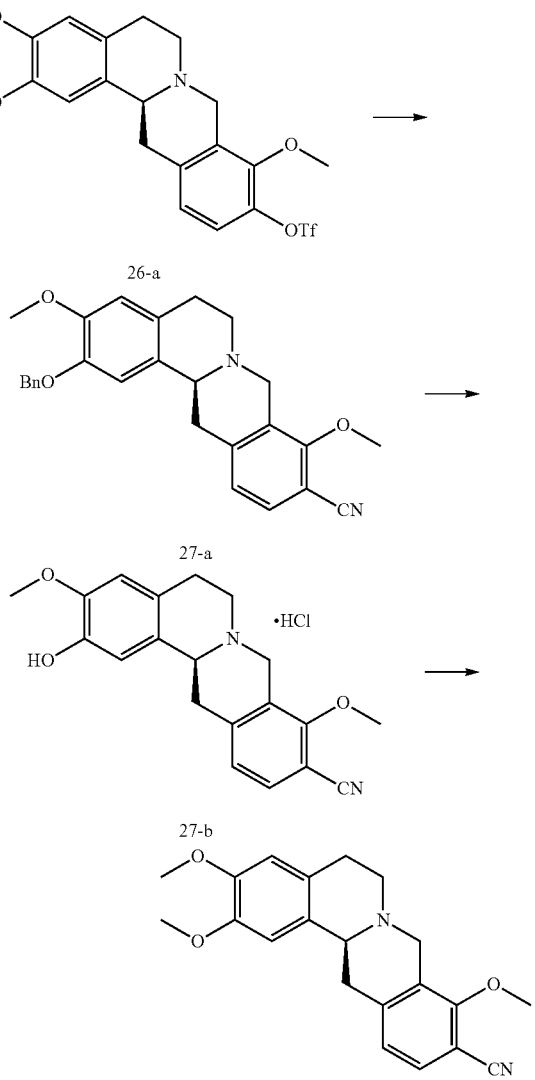

Step 1:

Dichloromethane (5 ml) and triethylamine (0.67 ml, 4.8 mmol) were added into 1-a (1 g, 2.4 mmol), and then Tf$_2$O (0.48 ml, 2.88 mmol) was slowly added dropwise under an ice bath. After completion of addition, the mixture was stirred for 3 h at room temperature. The resultant was extracted with dichloromethane-water, washed with saturated brine, dried over anhydrous sodium sulfate, concentrated, and subjected to column chromatography to obtain 26-a (0.74 g, yield: 56%).

Step 2:

26-a (500 mg, 0.91 mmol) was placed in a three-necked flask. Thereto, methylboronic acid (218 mg, 3.64 mmol), potassium carbonate (502 mg, 3.64 mmol), and tetrakis(triphenylphosphonium)palladium (210 mg , 0.182 mmol) and 1,4-dioxane (5 mL) were added. The mixture was refluxed at 100° C. overnight after nitrogen. replacement. The reaction solution was filtered, and the filtrate was concentrated and subjected to column chromatography to obtain 26-b (75 mg, yield: 20%).

Step 3:

26-b (75 mg, 0.180 mmol) was dissolved in ethyl acetate (2 mL). Thereto, palladium on carbon (10 mg) was added. The hydrogenation reaction was performed for 10 h. The resulting mixture was filtered and the mother liquor was concentrated to give 26-c (53 mg, yield: 90%). $^1$H NMR (300 MHz, CDCl$_3$) δ 2.27 (s, 3H), 2.59-2.71 (m, 2H), 2.85 (dd, 1H), 3.08-3.23 (m, 2H), 3.27 (dd, 1H), 3.55 (d, 2H), 3.75 (s, 3H), 3.88 (s, 3H), 4.23 (d, 1H), 6.60 (s, 1H), 6.82 (s, 1H), 6.84 (d, 1H), 7.00 (d, 1H). ESI-MS m/z 326.2 (M-HH)$^+$.

Step 4:

The title compound was prepared from the 26-c and dimethyl sulfate via methylation reaction, with reference to Step 1:

DMAc (15 ml), zinc cyanide (214 mg, 1.82 mmol), zinc powder (18 mg, 0.27 mmol), DPPF (101 mg, 0.18 mmol) and Pd$_2$(dba)$_3$ (83 mg, 0.09 mmol) were added into 26-a (500 mg, 0.91 mmol). The mixture was heated at 160° C. overnight. DMAc was distilled off, and the resulting mixture was extracted with dichloromethane-water, washed with saturated brine, dried, concentrated and subjected to column chromatography to give 27-a (348 mg, yield: 92%).

Step 2:

27-a (300 mg, 0.70 mmol) was dissolved in ethanol (4 mL). Thereto, 2 ml of concentrated hydrochloric acid was added, and the reaction was performed at 100° C. for 1 h. The solvent was directly distilled off to obtain compound 27-b (236 mg, yield: 90%).

Step 3:

27-b (250 mg, 0.67 mmol) was dissolved in acetone (4 mL). Thereto, dimethyl sulfate (0.095 mL, 1.01 mmol) and sodium hydroxide (107 mg, 2.68 mmol) were added. The reaction was performed at room temperature for 6 hours while stirring. The resultant was extracted with dichloromethane, washed with a saturated ammonium chloride solution. The organic phase was combined, washed with saturated brine, dried over anhydrous sodium sulfate, concentrated, and subjected to silica gel column chromatography to obtain the title compound (200 mg, yield: 85%). $^1$H NMR (300 MHz, CDCl$_3$) δ 2.60-2.73 (m, 2H), 2.91 (dd, 1H), 3.05-3.24 (m, 2H), 3.34 (dd, 1H), 3.49 (d, HI), 3.59 (dd, 1H), 3.87 (s, 3H), 3.88 (s, 3H), 4.08 (s, 3H), 4.19 (d, 1H), 6.62 (s, 1H), 6.69 (s, 1H), 6.96 (d, 1H), 7.38 (d, 1H), ESI-MS m/z 351.0 (M+H)$^+$.

EXAMPLE 28

(S)-2,3,9-trimethoxy-10-carbamoyl-6,8,13,13a-tetrahydro-5H-dibenzo[a,g] quinolizine (Class I-D)

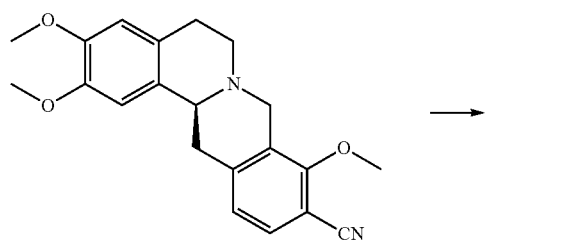

The title compound was prepared from the product of Example 27 via oxidative hydrolysis, in reference to the method for synthesizing the product of Example 5. That is, the product of Example 4 (320 mg, 0.91 mmol) was replaced with the product of Example 27 (320 mg, 0.91 mmol). The yield was 54%. $^1$H NMR (300 MHz, CDCl$_3$) δ 2.69 (m, 2H), 2.94 (m, 1H), 3.06-3.28 (m, 2H), 3.38 (dd, 1H), 3.60 (m, 2H), 3.84 (s, 3H), 3.87 (s, 3H), 3.89 (s, 3H), 4.26 (d, 1H), 5.87 (s, 1H), 6.63 (s, 1H), 6.72 (s, 1H), 7.08 (d, 1H), 7.57 (s, 1H), 7.90 (d, 1H). ESI-MS m/z 369.0 (M+H)$^+$.

EXAMPLE 29

(S)-2,3,9-trimethoxy-10-formyl-6,8,13,13a-tetrahydro-5H-dibenzo [a,g] quinolizine (Class I-D)

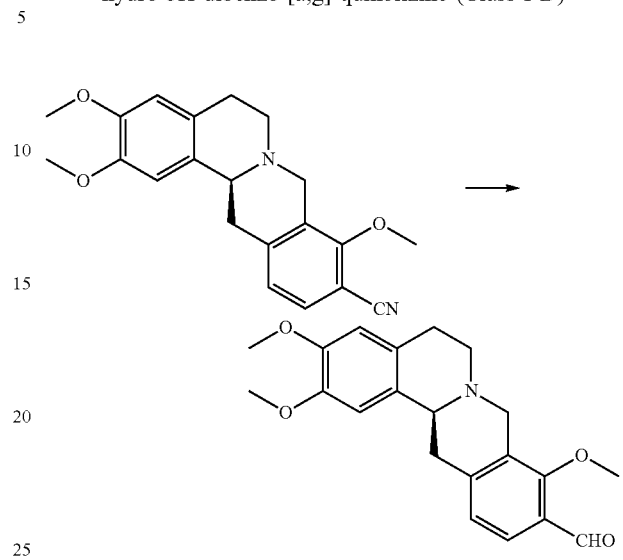

The title compound was prepared from the product of Example 27 via reduction reaction, in reference to the method for synthesizing the product of Example 6. That is, the product of Example 4 (500 mg, 1.42 mmol) was replaced with the product of Example 27 (500 mg, 1.42 mmol). The yield was 64%. $^1$H NMR (300 MHz, CD$_3$OD) δ 2.62-2.78 (m, 2H), 2.85 (dd, H), 3.02-3.27 (m, 2H), 3.54-3.72 (m, 3H), 3.80 (s, 3H), 3.83 (s, 3H), 3.93 (s, 3H), 4.27 (d, 1H), 6.71 (s, 1H), 6.89 (s, 1H), 7.16 (d, 1H), 7.67 (d, 1H), 10.27 (s. 1H). ESI-MS m/z 354.0 (M+H)$^+$.

EXAMPLE 30

(S)-2,3,9-trimethoxy-10-hydroxymethyl-6,8,13,13a-tetrahydro-5H-dibenzo[a,g] quinolizine (I-D)

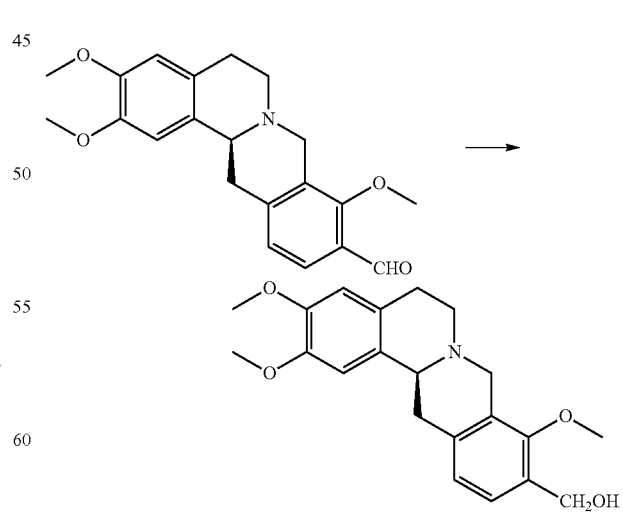

The title compound was prepared from the product of Example 29 via reduction reaction, in reference to the method for synthesizing the product of Example 7. That is, the product of Example 6 (390 mg, 1.10 mmol) was replaced with the product of Example 29 (390 mg, 1.10 mmol). The yield was 80%. $^1$H NMR (300 MHz, CD$_3$OD) δ 2.60-2.87 (m, 3H), 3.02-3.28 (m, 2H), 3.46-3.66 (m, 3H), 3.78 (s, 3H), 3.80 (s, 3H), 3.82 (s, 3H), 4.22 (d, 1H), 4.64 (s, 2H), 6.71 (s, 1H), 6.88 (s, 1H), 7.01 (d, 1H), 7.28 (d, 1H). ESI-MS m/z 356.0 (M+H)$^+$.

EXAMPLE 31

(S)-2,3,9-trimethoxy-10-aminomethyl-6,8,13,13a-tetrahydro-5H-dibenzo[a,g] quinolizine (Class I-D)

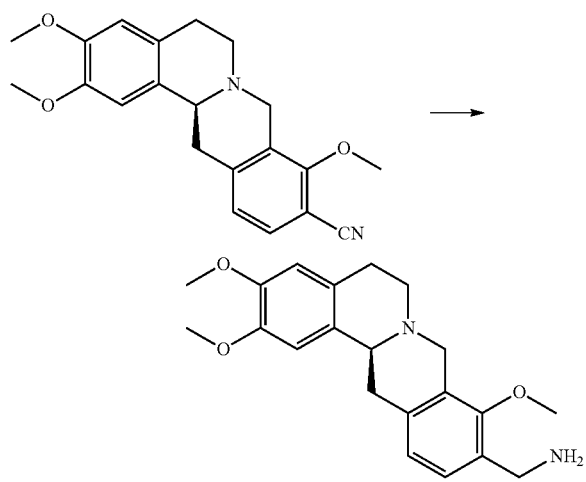

The title compound was prepared from the product of Example 27 via reduction reaction, in reference to the method for synthesizing the product of Example 10. That is, the product of Example 4 (150 mg, 0.42 mmol) was replaced with the product of Example 27 (150 mg, 0.42 mmol). The yield was 60%. $^1$H NMR (300 MHz, CDCl$_3$) δ 2.67~2.88 (m, 3H), 3.10~3.30 (m, 3H), 3.60 (d, 2H), 3.74 (d, 1H), 3.82 (s, 3H), 3.86 (s, 3H), 3.88 (s, 3H), 4.31-4.51 (m, 3H), 6.61 (s, 1H), 6.72 (s, 1H), 6.77 (d, 1H), 7.11 (d, 1H). m/z 355.0 (M+H)$^+$.

EXAMPLE 32

(S)-2,3,9-trimethoxy-10-acetaminomethyl-6,8,13,13a-tetrahydro-5H-dibenzo[a,g] quinolizine (Class I-D)

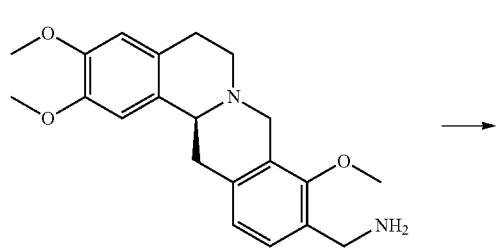

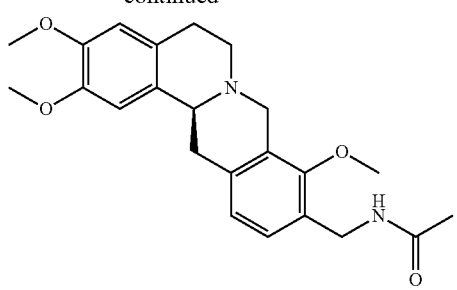

The title compound was prepared by reacting the product of Example 31 with acetic anhydride, in reference to the method for synthesizing the product of Example 11. That is, the product of Example 10 (75 mg, 0.21 mmol) was replaced with the product of Example 31 (75 mg, 0.21 mmol). The yield was 67%. $^1$H NMR (300 MHz, CDCl$_3$) δ 1.99 (s, 3H), 2.68 (m, 2H), 2.88 (dd, 1H), 3.14-3.37 (m, 3H), 3.59 (m, 2H), 3.79 (s, 3H), 3.87 (s, 3H), 3.89 (s, 3H), 4.23 (d, 1H), 4.45 (m, 2H), 5.86 (t, 1H), 6.62. (s, 1H), 6.72 (s, 1H), 6.93 (d, 1H), 7.12 (d, 1H). ESI-MS m/z 397.0 (M+H)$^+$.

EXAMPLE 33

(S)-2,10-diamino-3,9-dimethoxy-6,8,13,13a-tetrahydro-5H-dibenzo [a,g] quinolizine (Class I-B)

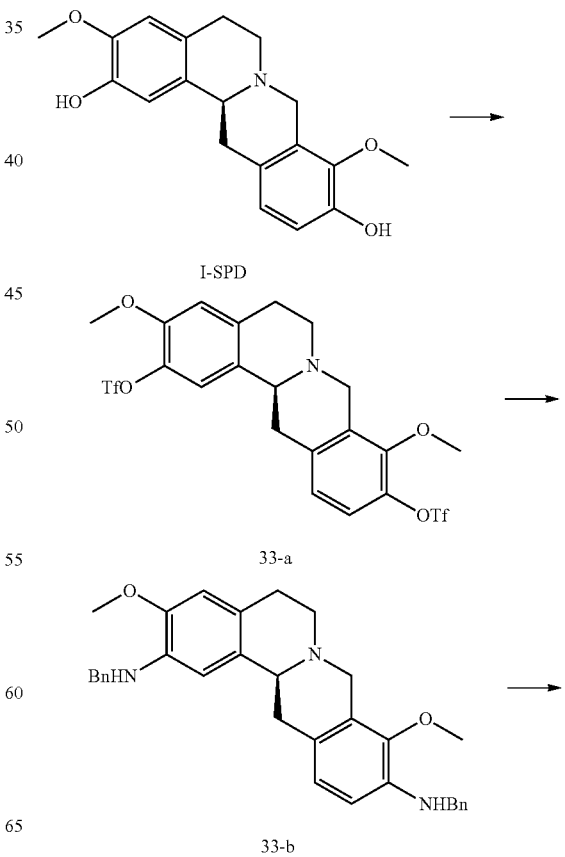

-continued

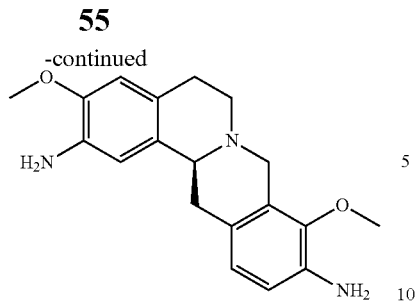

Step 1:
Dichloromethane (5 ml) and pyridine (1.25 ml, 15 mmol) were added into l-SPD (1 g, 3.0 mmol), and then Tf$_2$O (1.5 ml, 9.0 mmol) was slowly added dropwise under an ice bath. After completion of addition, the mixture was stirred for 1 h at room temperature. Pyridine was washed off with 1M hydrochloric acid. The resultant was extracted with dichloromethane-water, dried, concentrated, and subjected to column chromatography to obtain 33-a (1 g, yield: 60%). $^1$H-NMR (300 Hz, CDCl$_3$) δ 2.59-2.94 (m, 3H), 3.10-3.31 (m, 3H), 3.58 (m, 2H), 3.90 (s, 6H), 4.23 (d, 1H), 6.78 (s, 1H), 6.98 (d, 1H), 7.06 (s, 1H), 7.09 (d, 1H). ESI-MS m/z 592.0 (M+H)$^+$.

Step 2:
DMF (10 ml), cesium carbonate (1.32 g), palladium acetate (184 mg) and X-phos (132 mg) were added into 33-a (800 mg, 1.35 mmol), After completion of nitrogen replacement for 15 min, benzylamine (0.372 ml) was added thereto. The reaction was performed at 150° C. for 3 h while heating, DMF was distilled off. The resultant was extracted with dichloromethane-water, washed with saturated brine, dried, concentrated, and subjected to column chromatography to obtain 33-b (180 mg, yield: 26%). ESI-MS m/z 506.4 (M+H)$^+$.

Step 3:
Palladium on carbon (40 mg), methanol (3 ml) and ammonium formate (436 mg, 6.8 mmol) were added into 33-b (175 mg, 0.34 mmol). The mixture was heated to reflux overnight. The palladium on carbon was filtered off, and methanol was distilled off. The resulting mixture was extracted with dichloromethane-water, dried, concentrated, and subjected to column chromatography to obtain the title compound (53 mg, yield: 47%). $^1$H-NMR (300 Hz, CD$_3$OD) δ 2.72-2.95 (m, 3H), 3.06-3.28 (m, 3H), 3.42 (m, 2H). 3.77 (s, 3H), 3.85 (s, 3H), 4.35 (d, 1H), 6.64 (s, 1H), 6.75 (m, 2H), 6.81 (d, 1H). ESI-MS m/z 326.2 (M+H)$^+$.

EXAMPLE 34

(S)-2,10-di(acetamino)-3,9-dimethoxy-6,8,13,13a-tetrahydro-5H-dibenzo[a,g] quinolizine (Class I-B)

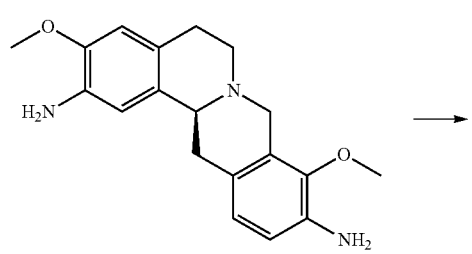

-continued

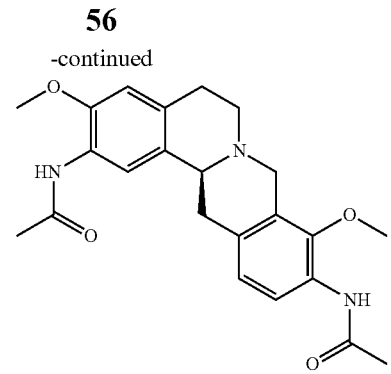

The title compound was prepared from he product of Example 33 and acetic anhydride, in reference to the method for synthesizing the product of Example 11. That is, the product of Example 10 (75 mg, 0.21 mmol) was replaced with the product of Example 33 (69 mg, 0.21 mmol). The yield was 34%. $^1$H-NMR (300 Hz, CDCl$_3$) δ 2.20 (s, 6H), 2.57-2.89 (m, 3H), 3.09-3.26 (m, 2H), 3.41 (d, 1H), 3.51-3.65 (m, 2H), 3.78 (s, 3H), 3.87 (s, 3H), 4.20 (d, 1H), 6.61 (s, 1H), 6.94 (d, 1H), 7.58 (s, 1H), 7.73 (s, 1H), 8.09 (d, 1H), 8.32 (s, 1H). ESI-MS m/z 409.9 (M+H)$^+$.

EXAMPLE 35

2,3-dicyano-9,10-dimethoxy-6,8,13,13a-tetrahydro-5H-dibenzo[a,g] quinolizine (Class I-F)

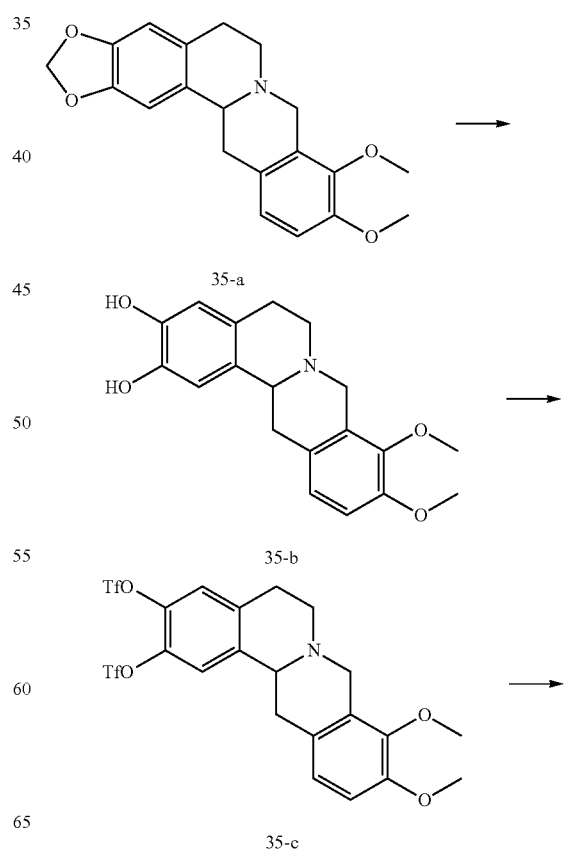

-continued

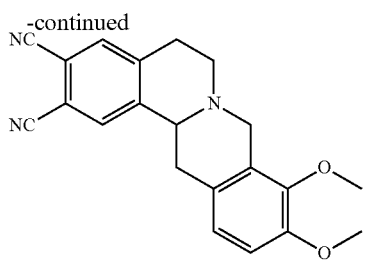

Step 1:

35-a (10 g, 29.4 mmol) was dissolved in dichloromethane (300 ml). Thereto, a solution of BCl₃ in dichloromethane (59 ml, 58.8 mmol) was added dropwise under an ice bath. The mixture was stirred at room temperature overnight. The next day, methanol (100 ml) was added dropwise to quench the excessive BCl₃. The solvent was evaporated and the resultant was directly subjected to the next reaction.

Step 2:

35-b (9 g, 27.5 mmol) was suspended in dichloromethane (100 ml). Thereto, pyridine (20 ml) was added, and then trifluoromethanesulfonic anhydride (10 ml) was added dropwise under an ice bath, and the mixture was stirred at room temperature for 5 h. Dichloromethane was added for dilution. The mixture was washed with a 1M HCl solution and saturated brine. The organic layer was dried and concentrated, and subjected to column chromatography to obtain 35-c (3 g, 17% of yield in two steps).

Step 3:

Zinc cyanide (1.6 g, 13.6 mmol), 1,1-bisdiphenylphosphine ferrocene (383 mg, 0.69 mmol), zinc powder (110 mg, 1.69 mmol). Pd₂(dba)₃ (273 mg, 0.47 mmol) and DMAc (10 ml) were added into 35-c (2.7 g, 4.5 mmol). The mixture was refluxed at 160° C. for 2 h after nitrogen replacement, and cooled to room temperature. Thereto, water and ethyl acetate were added for extraction. The organic layer was combined, washed with saturated brine, dried, concentrated and subjected to column chromatography to obtain the title compound (1 g, yield: 63%). ¹H NMR (300 MHz, CDCl₃) δ 2.59-2.71 (m, 1H), 2.77-2.94 (m, 2H), 3.17-3.33 (m, 3H), 3.58 (d, 1H), 3.67 (dd, 1H), 3.85 (s, 6H), 4.26 (d, 1H), 6.81 (d, 1H), 6.89 (d, 1H), 7.59 (s, 1H), 7.71 (s, 1H) ESI-MS m/z 346.3 (M+H)⁺.

EXAMPLE 36

9,10-dimethoxy-5,6,13,13a-tetrahydroisoquinolino[3,2-a]pyrrolo[3,4-g]isoquinoline-1,3(2H,8H)-dione (Class I-F)

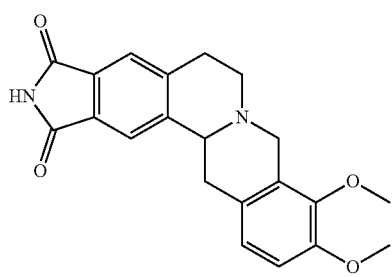 [SMILES: COc1ccc2c(c1OC)CN1CCc3cc4c(cc3C1C2)C(=O)NC4=O]

The sodium metal (170 mg, 7.3 mmol) was added to absolute ethanol (10 ml). After completely dissolved, the product of Example 35 (200 mg, 0.57 mmol) was added. The mixture was heated at 50° C. for 2 h. The reaction solution was poured into a 10% HNO₃ solution (10 ml), and stirred for 30 minutes. The solid was gradually precipitated therefrom. The mixture was filtered to obtain the product. The mother liquor was concentrated, extracted with ethyl acetate, and washed with saturated brine. The organic layer was dried, concentrated, subjected to column chromatographyto give the title compound (110 mg when combined with the filter cake, yield: 52%). ¹H NMR (300 MHz, CDCl₃) δ 2.16-2.39 (m, 2H), 2.65 (t, 1H), 2.75-2.95 (m, 2H), 3.17 (t, 2H), 3.35 (d, 1H), 3.44 (s, 3H), 3.49 (s, 3H),3.82 (d, 1H), 6.60 (s, 2H), 7.30 (s, 1H), 7.51 (s, 1H), 10.93 (s, 1H). ESI-MS m/z 365.2 (M+H)⁺.

EXAMPLE 37

(S)-2,10-dicyano-3,9-dimethoxy-6,8,13,13a-tetrahydro-5H-dibenzo [a,g] quinolizine (class I-B)

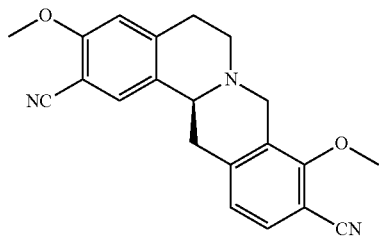

The title compound was prepared from 33-a, in reference to the method for synthesizing the product of Example 35. That is, 35-c was replaced with 33-a. The yield was 74%. ¹H NMR (300 MHz, CDCl₃) δ 2.58-2.94 (m, 3H), 3.13-3.38 (m, 3H), 3.48 (d, 1H), 3.58 (d, 1H), 3.91 (s, 3H), 4.09 (s, 3H), 4.19 (d, 1H), 6.71 (s, 1H). 6.96 (d, 1H), 7.41 (m, 2H). ESI-MS m/z 346.5 (M+H)⁺.

EXAMPLE 38

(S)-2,10-dicarbamoyl-3,9-dimethoxy-6,8,13,13a-tetrahydro-5H-dibenzo[a,g] quinolizine (Class I-B)

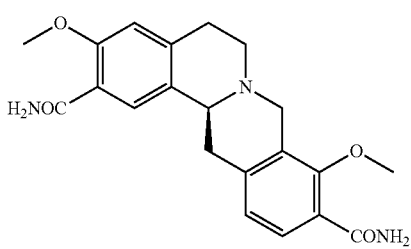

The title compound was prepared from the product of Example 37 via oxidation hydrolysis reaction, in reference to the method for synthesizing the product of Example 5. That is, the product of Example 4 (0.91 mmol) was replaced with the product of Example 37 (0.91 mmol). The yield was 40%. ¹H NMR (300 MHz, CD₃OD) δ 2.64-2.97 (m, 3H), 3.12-3.38 (m, 2H), 3.50-3.74 (m, 3H), 3.84 (s, 3H), 3.97 (s, 3H), 4.28 (d, 1H), 6.95 (s, 1H), 7.11 (d, 1H), 7.65 (d, 1H), 7.99 (s, 1H). ESI-MS m/z 382.1 (M+H)⁺.

EXAMPLE 39

2,3-Dicarbamoyl-9,10-dimethoxy-6,8,13,13a-tetra-hydro-5H-dibenzo [a,g] quinolizine (Class I-F)

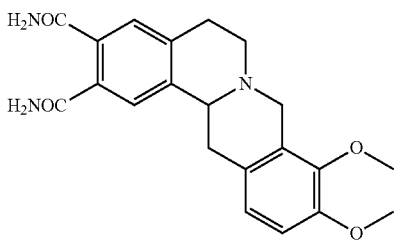 [SMILES: COc1ccc2c(c1OC)CN1CCc3cc(C(N)=O)c(C(N)=O)cc3C1C2]

The title compound was prepared from the product of Example 35 via oxidation hydrolysis reaction, in reference to the method for synthesizing the product of Example 5. That is, the product of Example 4 (0.91 mmol) was replaced with the product of Example 35 (0.91 mmol). The yield was 42%. $^1$H NMR (300 MHz, CD$_3$OD) δ 2.61-2.92 (m, 3H), 3.18 (m, 2H), 3.47 (dd, 1H), 3.55 (d, 1H), 3.68 (dd, 1H), 3.82 (s, 3H), 3.83 (s, 3H), 4.23 (d, 1H), 6.88 (d, 1H), 6.93 (d, 1H), 7.39 (s, 1H), 7.58 (s, 1H). ESI-MS m/z 382.1 (M+H)$^+$.

EXAMPLE 40

(S)-4,10,11-trimethoxy-3,6,7,9,14,14a-hexahydro-imidazo[4,5-h] isoquinolino[3,2-a]isoquinoline-2(1H)-one (Class I-A)

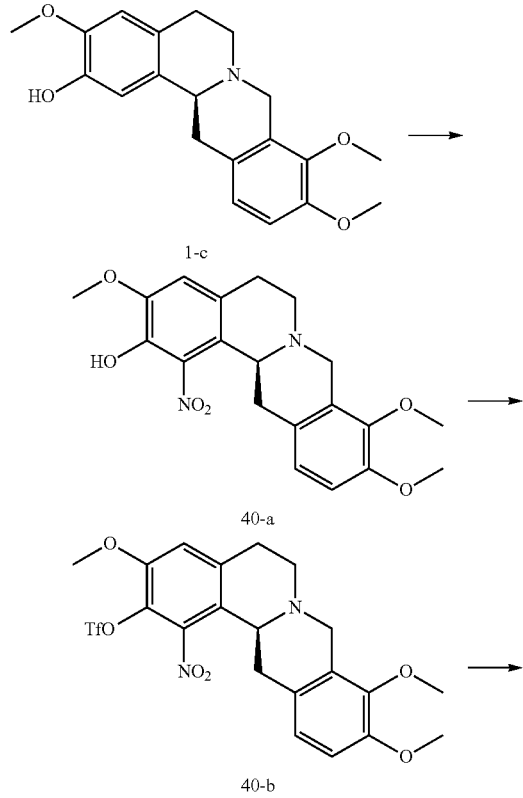

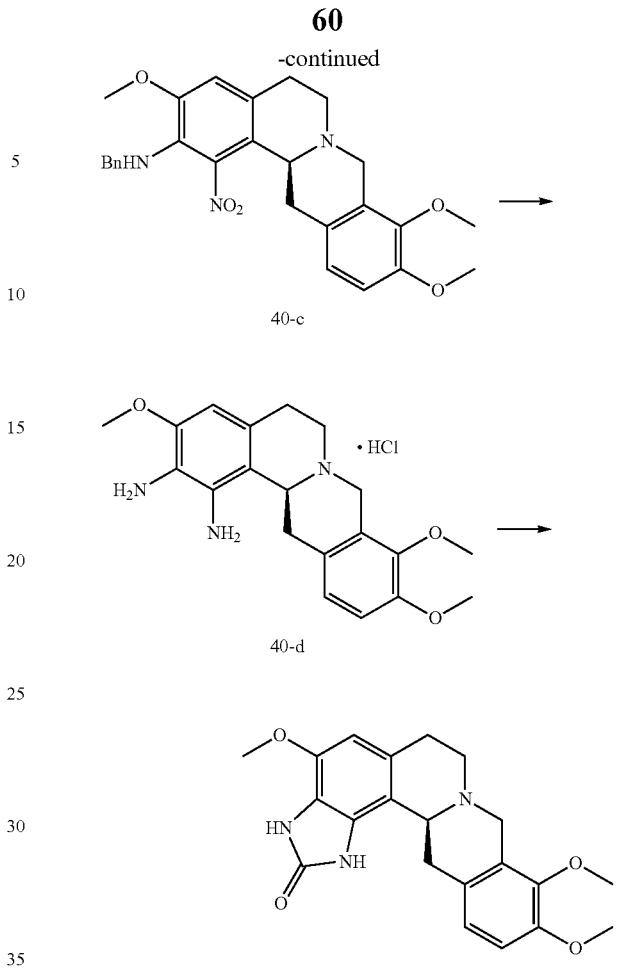

Step 1:
Dichloromethane (20 ml) and acetic acid (10 ml) were added into 1-c (4 g, 11.7 mmol), and then 30% nitric acid (4.6 ml) was added dropwise under an ice bath. The mixture was stirred at room temperature for 5 h. Dichloromethane-water was added for extraction. The organic phase was combined, washed three times with saturated brine, dried, and concentrated to obtain crude product 40-a (5 g), which was directly used in the next step.

Step 2:
Dichloromethane (40 ml) and triethylamine (2.86 ml, 20.6 mmol) were added into 40-a (4 g, 10.3 mmol), and then Tf$_2$O (1.7 ml, 10.3 mmol) was added dropwise under an ice bath. After completion of addition, the mixture was stirred at room temperature for 3 h. Dichloromethane-water was added for extraction, and the mixture was washed with saturated brine, dried, concentrated, and subjected to column chromatography to give 40-b (2.4 g, 49% of yield in two steps). $^1$H NMR (300 MHz, DMSO-d$_6$) δ 2.69-2.83 (m, 3H), 2.91-3.20 (m, 3H), 3.84 (d, 6H), 3.91 (d, 1H), 3.97 (s, 3H), 4.10 (t, 1H), 4.20 (d, 1H), 6.77 (s, 2H), 6.97 (s, 1H).

Step 3:
Dry toluene (20 ml), cesium carbonate (2.26 g, 6.9 mmol), palladium acetate (104 mg, 0.46 mmol), BINAP (289 mg, 0.46 mmol) were added into 40-b (2.4 g, 4.6 mmol). After completion of nitrogen replacement, benzylamine (1 ml, 9.2 mmol) was added thereto. The mixture was heated to reflux for 3 h. Toluene was distilled off. The resulting mixture was extracted with dichloromethane-water, washed with saturated brine, dried, concentrated, and subjected to column chromatography to obtain 40-c (1.4 g, yield: 63%).

Step 4:

Methanol (15 ml), palladium on carbon (140 mg) and ammonium formate (1.85 g, 29 mmol) were added into 40-c (1.4 g, 2.9 mmol). The mixture was heated to reflux for 2 h. The palladium on carbon was filtered, and methanol was distilled off. The resulting mixture was extracted with dichloromethane-water, washed with saturated brine, dried, concentrated, and formed into a salt by addition of HCl-MeOH to give 40-d as pale yellow solid (1 g, yield: 87%).

Step 5:

Dichloromethane (2.5 ml) and triethylamine (0.3 ml, 2.1 mmol) were added into 40-d (164 mg, 0.42 mmol). Triphosgene (50 mg, 0.16 mmol) was dissolved in toluene (2.5 ml), and the mixture was slowly added into the above reaction solution by using a constant pressure dropping funnel. The mixture was stirred at room temperature for 2 h. An appropriate amount of a saturated sodium bicarbonate solution was added thereto. Then the resulting mixture was extracted with dichloromethane-water, washed with saturated brine, dried, concentrated, and subjected to column chromatography to obtain the title compound (75 mg, yield: 46%). $^1$H NMR (300 MHz, DMSO-d$_6$) δ 2.31-2.74 (m, 3H), 2.90-3.12 (m, 2H), 3.28-3.42 (m, 1H), 3.63 (t, 2H), 3.73 (s, 3H), 3.77 (s, 3H), 3.79 (s, 3H), 4.05 (d, 1H), 6.43 (s, 1H), 6.84 (d, 1H), 6.89 (d, 1H), 10.51 (s, 1H), 10.63 (s, 1H). ESI-MS m/z 382.2 (M+H)$^+$, 380.2 (M−H)$^-$.

EXAMPLE 41

(S)-4,10,11-trimethoxy-3,6,7,9,14,14a-Hexahydro-imidazo[4,5-h] isoquinolino [3,2-a]isoquinoline-2 (1H)-thione (Class I-A)

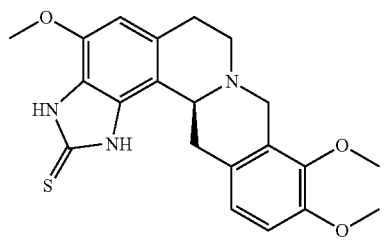

Water (2 ml), sodium hydroxide (51 mg, 1.26 mmol) and carbon disulfide (0.051 ml 0.84 mmol) were added into 40-d (150 mg, 0.42 mmol). The mixture was heated at 80° C. for 1 h. Dichloromethane-water was added for extraction, and the mixture was washed with saturated brine, dried, concentrated, and subjected to column chromatography to obtain the title compound (100 mg, yield: 59%). $^1$H NMR (300 MHz, CDCl$_3$) δ 2.61-2.85 (m, 3H), 3.10-3.30 (m, 3H), 3.76 (m, 2H), 3.84 (s, 3H), 3.87 (s, 3H), 3.89 (s, 3H), 4.20 (d, 1H), 6.46 (s, 1H), 6.77 (m, 2H). ESI-MS m/z 398.3 (M+H)$^+$.

EXAMPLE 42

(S)-4,10,11-trimethoxy-1,6,7,9,14,14a-hexahydro-imidazo[4,5-h] isoquinolino[3,2-a]isoquinoline (Class I-A)

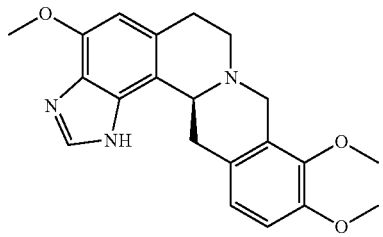

Formic acid (3 ml) was added into 40-d (200 mg, 0.56 mmol). The mixture was heated to reflux for 1 h. The solvent was distilled off. The mixture was adjusted to be alkalescency by adding saturated sodium bicarbonate. The resulting mixture was extracted with dichloromethane-water, dried, concentrated, and subjected to column chromatography to obtain the title compound (90 mg, yield: 43%). $^1$H NMR (300 MHz, CDCl$_3$) δ 2.68-2.88 (m, 3H), 3.19-3.39(m, 2H), 3.72(d, 1H), 3.84(s, 3H), 3.85(s, 3H), 3.95(s, 3H), 4.07(d, 2H), 4.29(d, 1H), 6.49(s, 1H), 6.76(d, 1H), 6.87(d, 1H), 7.93(s, 1H). ESI-MS m/z 366.1 (M+H)$^+$.

EXAMPLE 43

(S)-4,10,11-trimethoxy-1,6,7,9,14,14a-hexahydroiso-quinolino[3,2-a] [1,2,3]triazolo[4,5-h]isoquinoline (Class I-A)

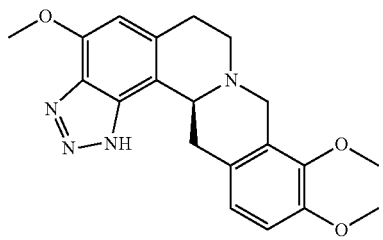

Water (2 ml) and acetic acid (0.42 ml, 7.28 mmol) were added into 40-d (200 mg, 0.56 mmol). The mixture was cooled to 0° C. under an ice bath. Sodium nitrite aqueous solution (containing 50 mg sodium nitrite) was added dropwise thereto. After reacting for 1 h under an ice bath, the mixture was heated to 85° C. for 1 h. The mixture was adjusted to be alkalescency by adding saturated sodium bicarbonate. The resulting mixture was extracted with dichloromethane-water, dried, concentrated, and subjected to column chromatography to obtain the title compound (80 mg, yield: 38%). $^1$H NMR (300 MHz, CDCl$_3$) δ 2.70-2.87 (m, 3H), 3.22-3.39 (m, 2H), 3.69 (d, 1H), 3.85 (d, 6H), 3.99 (s, 3H), 4.05 (d, 1H), 4.14 (d, H), 4.30 (d, 1H), 6.53 (s, 1H), 6.77 (d, 1H), 6.88 (d, 1H). ESI-MS m/z 367.2 (M+H)$^+$.

EXAMPLE 44

9,10-Dimethoxy-1,5,6,8,13,13a-hexahydroimidazo[4,5-g]isoquinolino[3,2-a]isoquinoline (Class I-F)

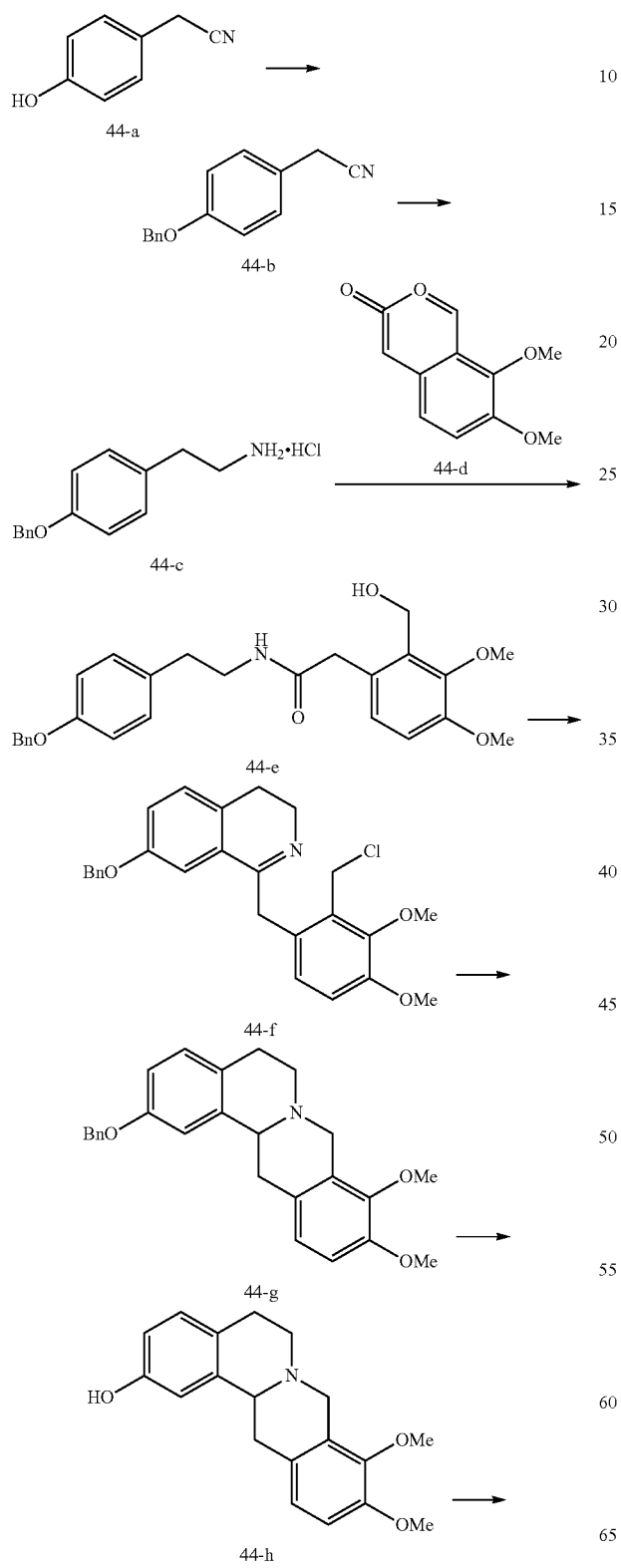

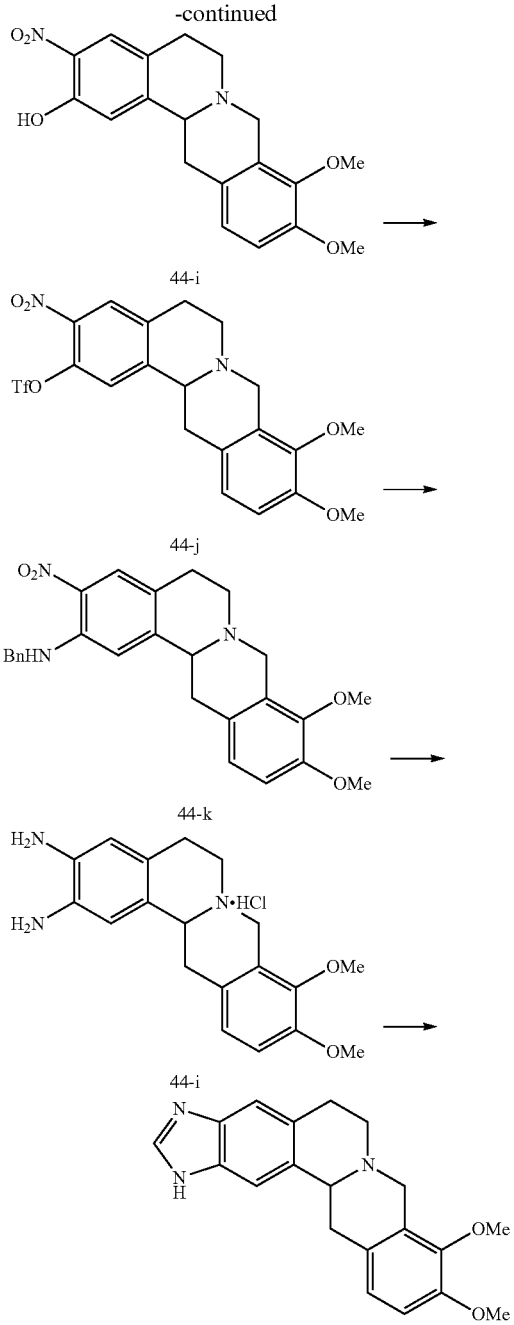

The raw material 44-h can be prepared from p-hydroxyphenylacetonitrile via multi-step reaction, with reference to the patent document CN102399166B or non-patent documents such as J. Org. Chem, 2009, 74, 9225-8228; Bioorg. Med. Chem. 2013, 21, 856-868. The title compound was prepared from the compound 44-h via method 5 (reaction formula 11). The specific operations are as follows:

Step 1:

Acetone (30 ml), potassium carbonate (6.2 g, 45 mmol) and benzyl bromide (3.2 ml) were added into p-hydroxyphenylacetonitrile 44-a (3 g, 22 mmol). The mixture was heated to reflux for 2 h. Acetone was distilled off. The resulting mixture was extracted with dichloromethane-water, washed with saturated brine, dried, concentrated, and slurried in methanol, filtered to obtain 44-b as a white solid (3.8 g, yield: 76%). $^1$H NMR (300 MHz, CDCl$_3$) δ 3.68 (s, 2H), 5.07 (s, 2H), 6.97 (d, 2H), 7.23 (d, 2H), 7.29-7.47 (m, 5H).

Step 2:

The sodium borohydride (1.3 g) was suspended in THF (5 ml), 2.66 ml of trifluoroacetic acid (diluted with 5 ml of THF) was slowly added dropwise to the sodium borohydride solution under an ice bath. After completion of addition, the mixture was increased to room temperature. 44-b (2 g) was dissolved in THF (5 ml), which was then slowly injected into the reaction system. Reaction was performed at room temperature for 4 h. The reaction solution was slowly added dropwise into ice water and stirred. The resulting mixture was extracted with dichloromethane-water, dried, concentrated, formed into a salt by adding HCl-MeOH, concentrated, and slurried in acetone, filtered to obtain 44-c as a white solid (1 g, yield: 42%).

Step 3:

Ethanol (20 ml) and triethylamine (2.4 ml) were added into 44-e (1.15 g, 4.4 mmol) and 44-d (0.92 g). The mixture was heated to reflux for 12 h. Ethanol was distilled off. The resulting mixture was extracted with dichloromethane-water, dried, concentrated, and slurried in petroleum ether/ethyl acetate, filtered to obtain 44-e (1,3 g, yield: 68%). ESI-MS m/z 436.3 (M-H)$^+$.

Step 4:

Toluene (30 ml) and phosphorus oxychloride (26 ml) were added into 44-e (10 g, 23.0 mmol). The mixture was heated to reflux for 4 h. The phosphorus oxychloride and toluene were distilled off. The residue was poured into ice water. Sodium carbonate solution was added to adjust pH=7. The resulting mixture was extracted with ethyl acetate, dried, and concentrated. Thereto, methanol was added, and then sodium borohydride (3 g) was added under an ice bath condition. After completion of addition, the mixture was stirred overnight at room temperature. Methanol was distilled off. The resulting mixture was extracted with dichloromethane-water, dried, concentrated, and subjected to column chromatography to obtain 44-g (0.7 g, two-step yield: 7%), $^1$H NMR (300 MHz, CDCl$_3$) δ 2.56-2.93 (m, 3H), 3.05-3.32 (m,3H), 3.56 (m, 2H), 3.86 (s, 6H), 4.26 (d, 1H), 5.06 (s, 2H), 6.74-6.92 (m, 4H), 7.06 (d, 1H), 7.29-7.50 (m, 5H). ESI-MS m/z 402.7 (M+H)$^+$.

Step 5:

Ethanol (5 ml) and palladium on carbon (70 mg) were added into 44-g (1.4 g). The hydrogenation reaction was performed at room temperature for 12 h. The resultant was filtered and the filtrate was concentrated to dryness to give 44-h (1.2 g, 100% yield), Step 6:

Dichloromethane (5 ml) was added into 44-h (0.9 g, 2.8 mmol), and then 65% concentrated nitric acid (0.33 ml) was added under an ice bath. After completion of addition, the mixture was stirred at room temperature for 2 h. Saturated sodium bicarbonate solution was added to adjust pH>7. The resulting mixture was extracted with dichloromethane-water, dried, concentrated, and subjected to column chromatography to obtain 44-i (0.3 g). $^1$H NMR (300 MHz, CDCl$_3$) δ 2.56-2.95 (m, 3H), 3.06-3.33 (m, 3H), 3.50-3.66 (m, 2H), 3.86 (s, 6H), 4.26 (d, 1H), 6.81 (d, 1H), 6.88 (d, 1H), 7.06 (s, 1H), 7.90 (s, 1H), 10.38 (brs, 1H). ESI-MS m/z 357.3 (M+1H)$^+$.

Step 7:

Dichloromethane (5 ml), pyridine (0.34 ml, 4.2 mmol) and trifluoromethanesulfonic anhydride (0.28 ml, 1.68 mmol) were added into 44-i (300 mg, 0.84 mmol). The mixture was stirred overnight at room temperature. 1M hydrochloric acid (4 ml) was added, and the mixture was extracted with saturated brine, dried, concentrated, and subjected to column chromatography to obtain 44-j (330 mg, yield: 80%). ESI-MS m/z 489.1 (M+H)$^+$.

Step 8:

Toluene (3 ml), palladium acetate (15 mg, 0.067 mmol.), BINAP (42 mg, 0.067 mmol), cesium carbonate (330 mg, 1.00 mmol) and benzylamine (0.15 ml, 1.34 mmol) were added into 44-j (330 mg, 0.67 mmol). The mixture was heated to reflux for 2 h. The resulting mixture was extracted with dichloromethane-water, dried, concentrated, and subjected to column chromatography to obtain 44-k (250 mg, yield: 83%), ESI-MS m/z 446.3 (M+H)$^+$.

Step 9:

Methanol (5 ml), palladium hydroxide (25 mg) and ammonium formate (360 mg) were added into 44-k (250 mg, 0.56 mmol). The mixture was heated to reflux for 2 h. Methanol was concentrated, and the mixture was extracted with dichloromethane-water, dried, and concentrated. Thereto, ethanol was added, and then HCl-MeOH was added dropwise to form a salt to obtain 44-1 as a pale yellow solid (180 mg, yield: 88%).

Step 10:

Formic acid (2.5 ml) was added into 44-1 (108 mg, 0.30 mmol). The mixture was heated to reflux for 1 h. Formic acid was distilled off, and a saturated sodium bicarbonate solution was added. The resulting mixture was extracted with dichloromethane-water, dried, concentrated, and subjected to column chromatography to obtain the title compound (50 mg, yield: 50%). $^1$H NMR (300 MHz, CDCl$_3$) δ 2.64-2.78 (m, 1H), 2.86-2.98 (m, 2H), 3.21-3.46 (m, 3H), 3.59 (d, 1H), 3.79 (d, 1H), 3.85 (s, 6H), 4.28 (d, 1H), 5.34 (brs, 1H), 6.80 (d, 1H), 6.90 (d, 1H), 7.38 (s, 1H), 7.59 (s, 1H), 7.99 (s, 1H). ESI-MS m/z 336.2 (M+H)$^+$.

EXAMPLE 45

9,10-Dimethoxy-6,8,13,13a-tetrahydro-5H-isoquinolino[3,2-a] oxazolo[4,5-g]isoquinoline (Class I-F)

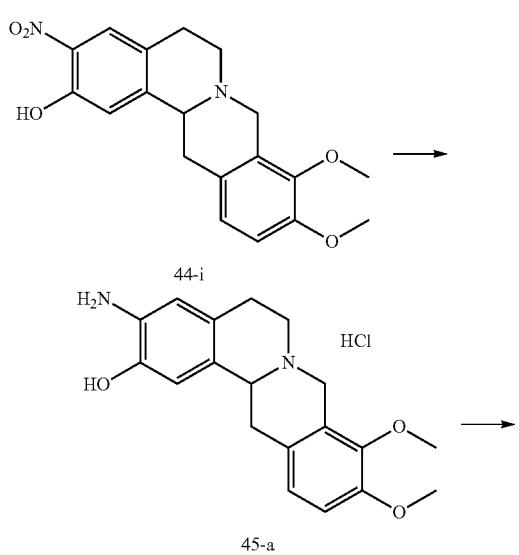

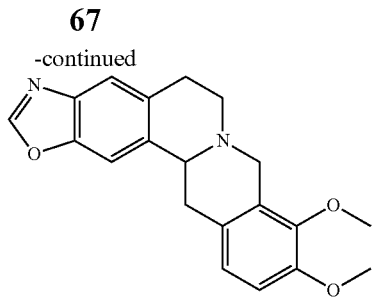

Step 1:

Methanol (20 ml) and palladium on carbon (40 mg) were added into 44-i (520 mg, 1.46 mmol). The hydrogenation reaction was performed at room temperature for 3 h, After filtration, the filtrate was added into HCl-MeOH to form a salt, and a pale yellow solid was precipitated. The mixture was filtered, and dried to obtain 45-a (480 mg, yield: 91%).

Step 2:

Trimethyl orthoformate (1.5 ml) was added into 45-a (85 mg, 0.23 mmol). The mixture was heated to reflux for 2 h. Trimethyl orthoformate was distilled off. The resulting mixture was subjected to silica gel column chromatography to obtain the title compound (60 mg, yield: 76%).

$^1$H NMR (300 MHz, CDCl$_3$) δ 2.63-2.74 (m, 1H), 2.86-2.99 (m, 2H), 3.21-3.41 (m, 3H), 3.58 (d, 1H), 3.76 (dd, 1H), 3.86 (d, 6H), 6.80 (d, 1H), 6.89 (d, 1H), 7.49 (s, 1H), 7.54 (s, 1H), 8.04 (s, 1H). ESI-MS m/z 337.2 (M+H)$^+$.

EXAMPLE 46

9,10-Dimethoxy-3,5,6,8,13,13a-Hexahydro-2H-isoquinolino[3,2-a] oxazolo[4,5-g]isoquinolin-2-one (Class I-F)

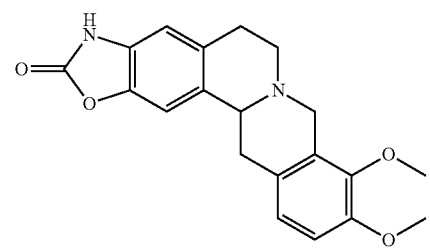 [SMILES: COc1ccc2c(c1OC)CN1CCc3cc4[nH]c(=O)oc4cc3C1C2]

Tetrahydrofuran (2 ml) and CDI (90 mg, 0.54 mmol) were added into 45-a (90 mg, 0.27 mmol). The reaction was performed at room temperature for 5 h. The resultant was extracted with dichloromethane-water, dried, concentrated and subjected to column chromatography to give the title compound as a white solid (62 mg, yield: 63%). $^1$H NMR (300 MHz, DMSO-d$_6$) δ 2.41-2.64 (m, 2H), 2.73 (d, 1H), 2.92-3.17 (m, 2H), 3.26-3.44 (m, 2H), 3.49 (d, 1H), 3.72 (s, 3H), 3.77 (s, 3H), 4.07 (d, 1H), 6.82 (s, 1H), 6.87 (dd, 1H), 7.29 (s, 1H), 11.50 (s, 1H). ESI-MS m/z 353.3 (M+H)$^+$.

EXAMPLE 47

10,11-Dimethoxy-4,6,7,9,14,14a-Hexahydroisoquinolino[3,2-a][1,4] oxazino[3,2-g]isoquinoline-3 (2H)-one (Class I-F)

Step 1:

Dichloromethane (5 ml), triethylamine (0.18 ml) and chloroacetyl chloride (0.038 ml) were added into 45-a (150 mg, 0.46 mmol). The mixture was stirred at room temperature overnight. The resulting mixture was extracted with dichloromethane-water, washed with saturated brine, dried, concentrated, and subjected to column chromatography to obtain 47-a (100 mg, yield: 54%). ESI-MS m/z 403.2 (M+H)$^+$.

Step 2:

Acetone (3 ml) and potassium carbonate (53 mg) were added into 47-a (100 mg, 0.24 mmol). The mixture was heated to reflux for 5 h. Acetone was distilled off, and the mixture was extracted with dichloromethane-water, washed with saturated brine, dried, concentrated, and subjected to column chromatography to give the title compound as a pure white solid (60 mg, yield: 66%). $^1$H NMR (300 MHz, DMSO-d$_6$) δ 2.37-2.68 (m, 3H), 2.89 (t, 1H), 3.09 (d, 1H), 3.24-3.45 (m, 3H), 3.71 (s, 3H), 3.76 (s, 3H), 4.05 (d, 1H), 4.52 (s, 2H), 6.61 (s, 1H), 6.80-6.98 (m, 3H), 10.66 (s, 1H). ESI-MS m/z 367.2 (M+H)$^+$, 365.2 (M−H)$^-$.

EXAMPLE 48

10,11-Dimethoxy-7,9,14,14a-tetrahydro-6H-isoquinolino[3,2-a] oxazolo[5,4-h]isoquinoline (Class I-E)

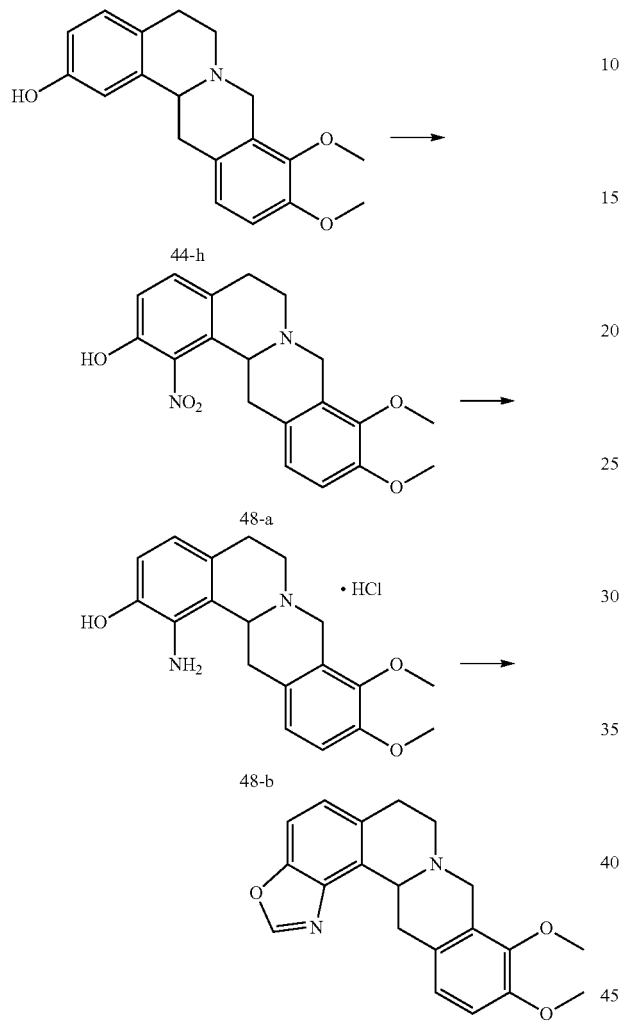

Step 1:

Dichloromethane (5 ml) was added into 44-h (0.9 g, 2.8 mmol), and then 65% concentrated nitric acid (0.33 ml) was added under an ice bath. After completion of addition, the mixture was stirred at room temperature for 2 h. Saturated sodium bicarbonate solution was added to adjust pH>7. The resulting mixture was extracted with dichloromethane-water, dried, concentrated, and subjected to column chromatography to give 48-a (0.5 g). $^1$H NMR (300 MHz, CDCl$_3$) δ 2.66-2.94 (m, 4H), 2.98-3.18 (m, 2H), 3.85 (s, 6H), 3.93 (d, 1H), 4.22 (d, 1H), 4.63 (dd, 6.76 (d, 2H), 7.01 (d, 1H), 7.29 (d, 1H). EST-MS m/z 357.3 (M+H)$^+$.

Step 2.

Methanol (20 ml) and palladium on carbon (40 mg) were added into 48-a (400 mu, 1.12 mmol). The hydrogenation reaction was performed at room temperature for 3 h. After filtration, the filtrate was added into HCl-MeOH to form a salt, and a pale yellow solid was precipitated. The resultant was filtered, and dried to obtain 48-b (410 mg, yield: 100%).

Step 3:

Trimethyl orthoformate (1.5 ml) was added into 48-b (85 mg, 0.23 mmol). The mixture was heated to reflux for 2 h. Trimethyl orthoformate was distilled off, and the resultant was subjected to silica gel column chromatography to give the title compound (42 mg, yield: 53%). $^1$H NMR (300 MHz, DMSO-d$_6$) δ 2.66-3.00 (m, 3H), 3.17 (t, 1H), 3.42 (d, 1H), 3.75 (s, 3H), 3.78 (s, 3H), 3.88 (dd, 1H), 4.16 (d, 1H), 4.34 (d, 2H), 6.93 (m, 2H). 7.26 (d, 1H), 7.64 (d, 1H), 8.75 (s, 1H). ESI-MS m/z 337.2 (M+H)$^+$.

EXAMPLE 49

10,11-Dimethoxy-6,7,14,14a-tetrahydro-1H-isoquinolino[3,2-a] oxazolo[5,4-h] isoquinoline-2 (9H)-one (Class I-E)

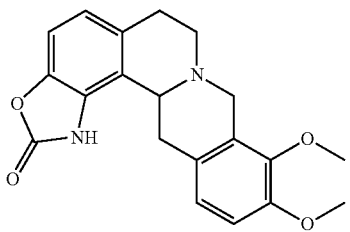 [SMILES: COc1ccc2c(c1OC)CN1CCc3ccc4oc(=O)[nH]c4c3C1C2]

The title compound was prepared from 48-b, in reference with the method for synthesizing the product of Example 46. That is, 45-a was replaced with 48-b. The yield was 75%. $^1$H NMR (300 MHz, CDCl$_3$) δ 2.60-2.87 (m, 3H), 3.09-3.25 (m, 3H), 3.68 (t, 2H), 3.85 (s, 6H), 4.17 (d, 1H), 6.73-6.81 (dd, 2H), 6.90 (d, 1H), 7.03 (d, 1H), 9.41 (s, 1H). ESI-MS m/z 353.2 (M+H)$^+$.

EXAMPLE 50

11,12-Dimethoxy-3,7,8,10,15,15a-hexahydroisoquinolino[3,2-a][1,4] oxazino [2,3-h]isoquinoline-2 (1H)-one (Class I-E)

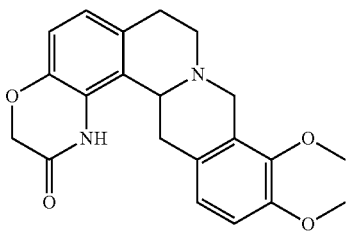 [SMILES: COc1ccc2c(c1OC)CN1CCc3ccc4c(c3C1C2)NC(=O)CO4]

The title compound was prepared from 48-b, in reference with the method for synthesizing the product of Example 47. That is, 45-a was replaced with 48-b. The yield: 59%. $^1$H NMR (300 MHz, CDCl$_3$) δ 2.61-2.90 (m, 3H), 2.93-3.19 (m, 3H), 3.84 (s, 3H), 3.85 (s, 3H), 3.91 (m, 2H), 4.20 (d, 1H), 4.31 (d, 1H), 4.48 (d, 1H), 6.69-6.89 (m, 4H), 8.14 (brs, 1H). ESI-MS m/z 367.2 (M+H)$^+$, 365.2 (M−H)$^-$.

EXAMPLE 51

(S)-2-(difluoromethoxy)-3,9,10-trimethoxy-6,8,13,13a-tetrahydro-5H-dibenzo[a,g] quinolizine (Class I-A)

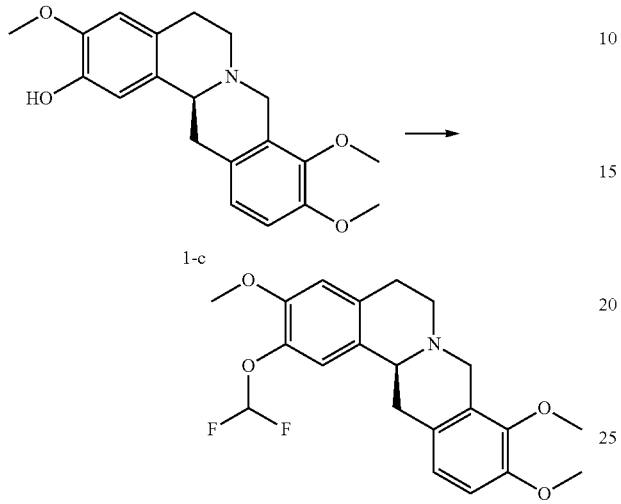

1-c (200 mg, 0.58 mmol) was dissolved in DMF (5 ml). Thereto, cesium carbonate (378 mg, 1.16 mmol) was added. The mixture was heated to 100° C. Monochlorodifluoromethane was passed into the reaction system for 5 to 6 hours until TLC shows the reaction of the starting materials was completed. The reaction was stopped, and DMF was distilled off. The resultant was extracted with dichloromethane-water, washed with saturated brine, dried over anhydrous sodium sulfate, concentrated, and subjected to column chromatography to obtain the title compound (69 mg, yield: 30%). $^1$H NMR (300 MHz, CDCl$_3$) δ 2,58-2.88 (m, 3H), 3.12-3.29 (m, 3H), 3.54 (d, 2H), 3.85 (s, 6H), 3.86 (s, 3H), 4.25 (d, 1H), 654 (t, 1H), 6.70 (s, 1H), 6.79 (d, 1.H), 6.88 (d, 1H), 7.05 (s, 1H). ESI-MS m/z 392.3 (M+H)$^+$.

EXAMPLE 52

(S)-2-allyloxy-3,9,10-trimethoxy-6,8,13,13a-tetahydro-5H-dibenzo [a,g] quinolizine (Class I-A)

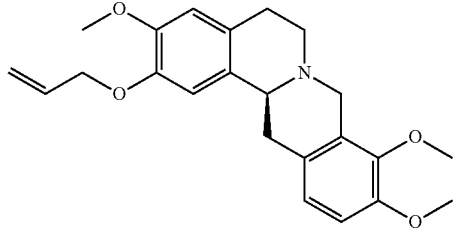 [SMILES: C=CCOc1cc2c(cc1OC)CCN1Cc3c(ccc(OC)c3OC)C[C@@H]21]

1-c (200 mg, 0.58 mmol) was dissolved in DMF (5 ml). Thereto, cesium carbonate (378 mg, 1.16 mmol) and 3-bromopropene (0.073 ml, 0.87 mmol) were added. The mixture was stirred at room temperature for 3 h. DMF was distilled off. The resultant was extracted with dichloromethane-water, washed with saturated brine, dried over anhydrous sodium sulfate, concentrated, and subjected to column chromatography to obtain the title compound (112 mg, yield: 50%). $^1$H NMR (300 MHz, DMSO-d$_6$) δ 2.96 (m, 2H), 3.38 (m, 2H), 3.77 (s, 3H), 3.79 (s, 3H), 3.82 (s, 3H), 3.84 (m, 2H), 4.33-4.72 (m, 5H), 5.27 (dd, 1H), 5.42 (dd, 1H), 6.05 (m, 1H), 6.84 (s, 1H), 7.03 (d, 1H), 7.05 (s, 1H), 7.09 (d, 1H), 11.06 (brs, 1H). ESI-MS m/z 382.2 (M+H)$^+$.

EXAMPLE 53

(S)-2-cyclopropoxy-3,9,10-trimethoxy-6,8,13,13a-tetrahydro-5H-dibenzo[a,g] quinolizine hydrochloride (Class I-A)

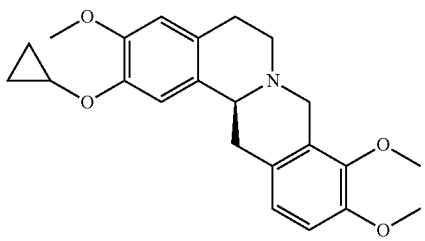 [SMILES: COc1cc2c(cc1OC1CC1)[C@@H]1Cc3ccc(OC)c(OC)c3CN1CC2]

1-c (200 mg, 0.58 mmol) was dissolved in DMF (5 ml). Thereto, cesium carbonate (378 mg, 1.16 mmol) and bromocyclopropane (0.070 ml, 0.87 mmol) were added. The mixture was stirred at 150° C. for 3 h. DMF was distilled off, and the resultant was extracted with dichloromethane-water, washed with saturated brine, dried over anhydrous sodium sulfate, concentrated, and subjected to column chromatography to obtain the title compound (141 mg, yield: 63%). $^1$H NMR (300 MHz, DMSO-d$_6$) δ 0.56-0.87 (m, 4H), 2.89 (d, 1H), 3.06 (t, 1H), 3.37 (m, 2H), 3.74 (s, 3H), 3.80 (s, 3H), 3.82 (s, 3H), 3.84 (m, 3H), 4.39 (dd, 1H), 4.66 (m, 2H), 6.83 (s, H), 7.04 (d, 1H), 7.09 (d, 1H), 7.26 (s, 1H), 11.27 (brs, 1H). ESI-MS m/z 382.2 (M+H)$^+$.

EXAMPLE 54

(S)-2-cyclopentyloxy-3,9,10-trimethoxy-6,8,13,13a-tetrahydro-5H-dibenzo[a,g] quinolizine hydrochloride (Class I-A)

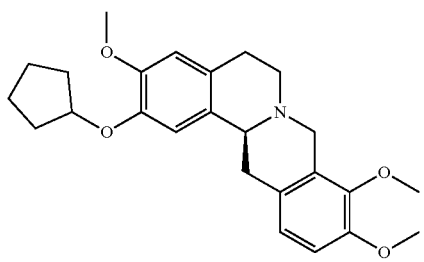 [SMILES: COc1cc2c(cc1OC1CCCC1)[C@@H]1Cc3ccc(OC)c(OC)c3CN1CC2]

The title compound was prepared from 1-c and bromocyclopentane, with reference to the method for synthesizing the product of Example 52. That is, 3-bromopropene was replaced with bromocyclopentane. The yield: 42%. $^1$H NMR (300 MHz, CDCl$_3$) δ 1.89 (m, 8H), 2.56-2.72 (m, 2H), 2.82 (dd, 1H), 3.05-3.28 (m, 3H), 3.54 (d, 2H), 3.83 (s, 3H), 3.85 (s, 6H), 4.24 (d, 1H), 4.76 (m, 1H), 6.61(s, 1H), 6.74 (s, 1H), 6.79 (d, 1H), 6.88 (d, 1H).

EXAMPLE 55

(S)-2,10-di(hydroxyethoxy)-3,9-dimethoxy-6,8,13,13a-tetrahydro-5H-dibenzo [a,g] quinolizine (Class I-B)

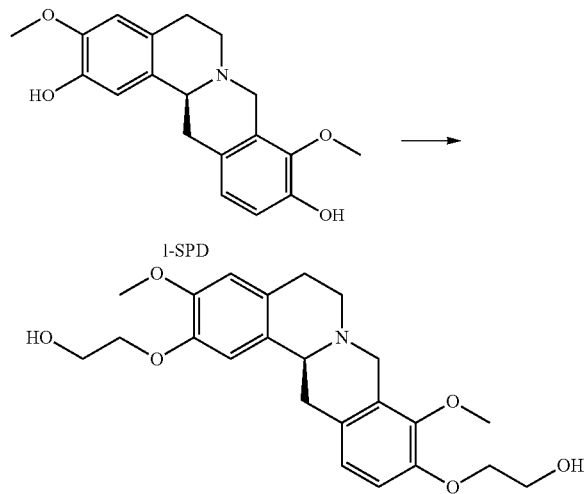

DMF (3 ml), potassium carbonate (1.26 g, 9.1 mmol), bromoethanol (0.13 ml, 1.82 mmol), potassium iodide (75 mg, 0.45 mmol) were added into l-SPD (300 mg, 0.91 mmol). The reaction was performed at 120° C. for 3 h. The resultant was extracted with dichloromethane, and washed three times with water. DMF was washed off, and the organic phase was combined, washed with saturated brine, dried over anhydrous sodium sulfate, concentrated, and subjected. to column chromatography to obtain the title compound (10 mg, yield: 2%). $^1$H NMR (300 Hz, DMSO-d$_6$) δ 2.85 (d, 1H), 3.01 (t, 1H), 3.35 (m, 2H), 3.64-3.88 (m, 12H), 4.00 (m, 4H), 4.36 (dd, 4.60 (m, 2H), 4.92 (brs, 2H), 6.81 (s, 1H), 6.97 (d, 1H), 7.02 (s, 1H), 7.06 (d, 1H). ESI-MS m/z 416.0 (M+H)$^+$.

EXAMPLE 56

(S)-2,3,10-trimethoxy-9-hydroxyethoxy-6.8,13,13a-tetrahydro-5H-dibenzo[a,g] quinolizine (Class I-C)

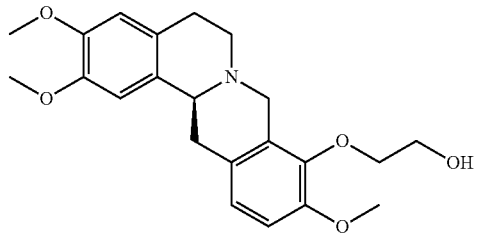 [SMILES: COc1cc2c(cc1OC)[C@@H]1Cc3ccc(OC)c(OCCO)c3CN1CC2]

The title compound was prepared from 19-b and bromoethanol, with reference to the method for synthesizing the product of Example 55. That is, l-SPD was replaced with 19-b. The yield: 44%. $^1$H NMR (300 MHz, CDCl$_3$) δ 2.56-2.74 (m, 2H), 2.83 (dd, 1H), 3.06-3.33 (m, 3H), 3.56 (d, 2H), 3.80-3.95 (m, 11H), 3.99-4.20 (m, 2H), 4.27 (d, 1H), 6.61 (s, 1H), 6.72 (s, 1H), 6.79 (d, 1H), 6.91 (d, 1H), ESI-MS m/z 386.0 (M+H)$^+$.

EXAMPLE 57

(S)-2,3,10-trimethoxy-9-cyclopropoxy-6,8,13,13a-tetrahydro-5H-dibenzo[a,g] quinolizine hydrochloride (Class I-C)

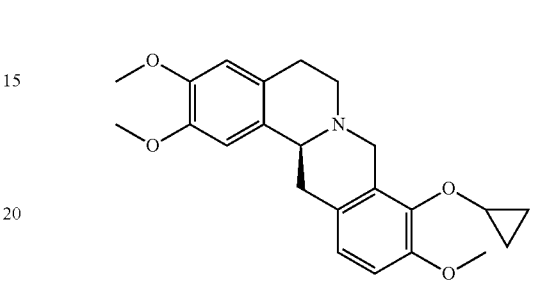

The title compound was prepared from 19-b and bromocyclopropane, with reference to the method for synthesizing the product of Example 53. That is, 1-c was replaced with 19-b. The yield: 65%. $^1$H NMR (300 MHz, DMSO-d$_6$) δ 0.53 (m, 2H), 0.77 (m, 2H), 2.86 (d, 1H), 3.04 (dd, 1H), 3.37 (m, 2H), 3.76 (s, 3H), 3.78 (s, 3H), 3.80-3.90 (m, 5H), 4.25 (dd, 1H), 4.34 (m, 1H), 4.41 (d, 1H), 4.66 (t, 1H), 6.82 (s, 1H), 7.02 (s, 1H), 7.03 (d, 1H), 7.10 (d, 1H), 11.59 (brs, 1H). ESI-MS m/z 382.1 (M+H)$^+$.

EXAMPLE 58

(S)-2,3,10-trimethoxy-9-cyclopentyloxy-6,8,13,13a-tetrahydro-5H-dibenzo[a,g] quinolizine (Class I-C)

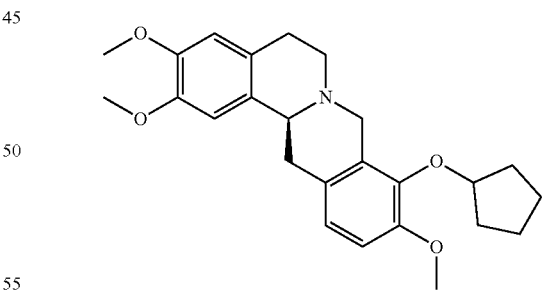

The title compound was prepared from 19-b and bromocyclopropane, with reference to the method for synthesizing the product of Example 54. That is, 1-c was replaced with 19-b. The yield: 33%. $^1$H NMR (300 MHz, CDCl$_3$) δ 1.85 (m, 8H), 2.55-2.73 (m, 2H), 2.84 (dd, 1H), 2.06-3.30 (m, 3H), 3.51 (m, 2H), 3.82 (s, 3H), 3.87 (s, 3H), 3.88 (s, 3H), 4.20 (d, 1H), 4,95 (m, 1H), 6.61 (s, 1H), 6.73 (s, 1H), 6.77 (d, 1H), 6.84 (d, 1H). ESI-MS m/z 410.3 (M+H)$^+$.

EXAMPLE 59

(S)-2,3,9-trimethoxy-10-cyclopropoxy-6,8,13,13a-tetrahydro-5H-dibenzo[a,g] quinolizine (Class I-D)

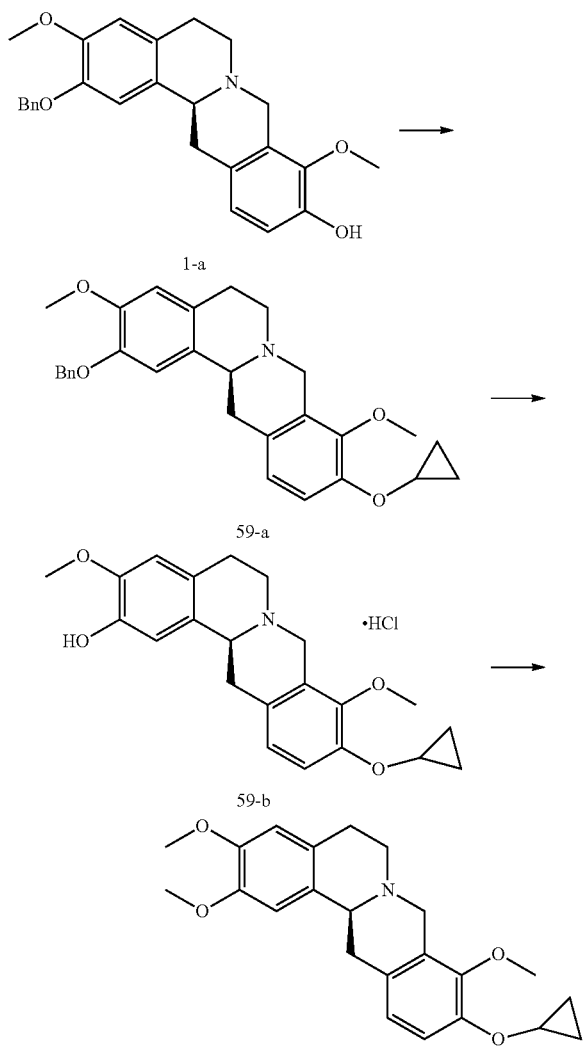

Step 1:

1-a (500 mg, 1.20 mmol) was dissolved in DMF (8 ml). Thereto, cesium carbonate (782 mg, 2.40 mmol) and bromocyclopropane (0.12 ml, 1.80 mmol) were added. The mixture was stirred at 150° C. for 3 h. DMF was distilled off, and the resultant was extracted with dichloromethane-water, washed with saturated saline solution, dried over anhydrous sodium sulfate, concentrated, and subjected to column chromatography to give 59-a (356 mg, yield: 65%).

Step 2:

59-a (300 mg, 0.65 mmol) was dissolved in ethanol (4 mL). Thereto, 2 ml of concentrated hydrochloric acid was added. The reaction was performed at 100° C. for 1 h. The solvent was directly distilled off to obtain compound 59-b (233 mg, yield: 88%).

Step 3:

59-b (200 mg, 0.49 mmol) was dissolved in acetone (4 mL). Thereto, dimethyl sulfate (0.070 mL, 0.74 mmol) and sodium hydroxide (80 mg, 1.98 mmol) were added. The reaction was performed at room temperature for 6 h while stirring. The resultant was extracted with dichloromethane, and washed with a saturated ammonium chloride solution. The organic phase was combined, washed with saturated brine, dried over anhydrous sodium sulfate, concentrated, and subjected to silica gel column chromatography to obtain the title compound (155 mg, yield: 82%). $^1$H NMR (300 MHz, DMSO-$d_6$) δ 0.55-0.81 (m, 4H), 2.35-2.69 (m, 3H), 2.83-3.16 (m, 3H), 3.34 (m, 2H), 3.68 (s, 3H), 3.73 (d, 6H), 3.85 (m, 1H), 4.04 (d, 1H), 6.67 (s, 1H). 6.86 (s, 1H), 6.89 (d, 1H), 7.13 (d, 1H). ESI-MS m/z 382.3 (M+H)$^+$.

EXAMPLE 60

(S)-2-methanesulfonylamino-3,9,10-trimethoxy-6,8,13,13a-tetrahydro-5H-dibenzo[a,g] quinolizine (Class I-A)

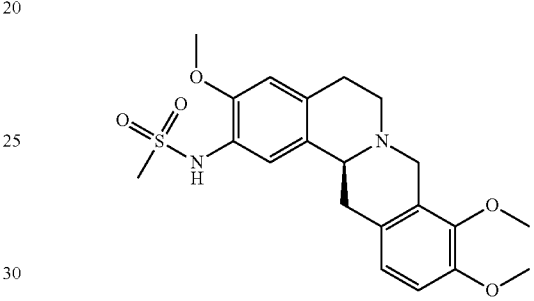

The product of Example 13 (40 mg) was added to 2 ml of dichloromethane, and one drop of pyridine (about 1.5 eq) was added thereto. One drop of methanesulfonyl chloride (about 1.5 eq) was added dropwise under an ice bath. The mixture was kept in an ice bath for 10 minutes while stirring, and moved to room temperature for reaction for 3 hours. The system was extracted with dichloromethane and water, washed with saturated brine, dried and concentrated to obtain 40 mg of a crude product. The residue was subjected to column chromatography (eluent: DCM/MeOH=100:1) to obtain the title compound (20 mg). ESI-MS m/z 419.24 (M+H)$^+$.

Pharmacological Experiments

1) $D_1$ antagonistic activity test

LANCE™ cAMP 384 Kit (PerkinElmer, USA) was used to test the antagonism of the compound against the $D_1$ receptor using the HEK293 cells expressing human recombinant $D_1$ receptor. The $D_1$ antagonism of the compound was evaluated by testing the antagonistic action of the compounds against dopamine on the induction of cAMP production in HEK293 cells. The cAMP concentration test was performed according to the method described in the kit instructions. The test concentration of the compound was 0.1 nM to 10000 nM. SCH23390 was used as a positive control. The IC$_{50}$ was calculated by Excelfit software. The test results of some compounds were shown in Table 1.

2) $D_2$ antagonistic activity test

LANCE™ cAMP 384 Kit (PerkinElmer, USA) was used to test the antagonism of the compound against the $D_2$ receptor using the HEK293 cells expressing human recombinant $D_2$ receptor. The $D_2$ antagonism of the compound was evaluated by testing the antagonistic action of the compounds against dopamine on the inhibition of cAMP production in HEK293 cells. The cAMP concentration test was performed according to the method described in the kit instructions. The test concentration of the compound was 0.1 nM to 10000 nM. Risperidone was used as a positive control. The $IC_{50}$ was calculated by Excelfit software. The test results of some compounds were shown in Table 1 (ND means the test was not performed).

TABLE 1

| Test Compound | $D_1$ Antagonistic Activity ($IC_{50}$, nmol/L) | $D_2$ Antagonistic Activity ($IC_{50}$, nmol/L) |
|---|---|---|
| Compound of Example 1 | 34.9 | 620 |
| Compound of Example 2 | ND | 280 |
| Compound of Example 4 | 310 | 950 |
| Compound of Example 5 | 170 | 35 |
| Compound of Example 6 | 49 | 210 |
| Compound of Example 7 | 61 | 770 |
| Compound of Example 11 | 500 | 750 |
| Compound of Example 12 | 240 | 500 |
| Compound of Example 13 | 140 | 280 |
| Compound of Example 15 | 120 | 550 |
| Compound of Example 17 | 240 | 150 |
| Compound of Example 18 | 390 | 610 |
| Compound of Example 19 | 1300 | ND |
| Compound of Example 21 | 1500 | ND |
| Compound of Example 24 | 1300 | ND |
| Compound of Example 25 | 1700 | 2300 |
| Compound of Example 26 | ND | 940 |
| Compound of Example 27 | 311 | 1000 |
| Compound of Example 28 | 2160 | ND |
| Compound of Example 29 | ND | 2500 |
| Compound of Example 30 | 1080 | 510 |
| Compound of Example 32 | ND | 663 |
| Compound of Example 33 | 270 | 440 |
| Compound of Example 36 | 26.2 | 427 |
| Compound of Example 37 | 211 | 19 |
| Compound of Example 38 | 3400 | 620 |
| Compound of Example 40 | 4.0 | 27 |
| Compound of Example 41 | ND | 20 |
| Compound of Example 42 | 31.1 | 291 |
| Compound of Example 43 | ND | 54 |
| Compound of Example 44 | 672 | 139 |
| Compound of Example 45 | 116 | ND |
| Compound of Example 46 | 378 | 184 |
| Compound of Example 47 | 19.9 | 146 |
| Compound of Example 49 | 219 | ND |
| Compound of Example 50 | 855 | ND |
| Compound of Example 51 | ND | 390 |
| Compound of Example 52 | 220 | 450 |
| Compound of Example 53 | 960 | 1300 |
| Compound of Example 55 | 443 | ND |
| Compound of Example 56 | 1050 | 2800 |
| Compound of Example 60 | 525 | 6.2 |
| l-SPD | 7.7 | 37 |
| Positive Control | 0.92 | 2.8 |

3) $5-HT_{1A}$ agonistic activity test

LANCE™ cAMP 384 Kit (PerkinElmer, USA) was used to test the agonistic effect of the compound on $5-HT_{1A}$ receptor using the HEK293 cells expressing human recombinant $5-HT_{1A}$ receptor. The $5-HT_{1A}$ agonistic effect of the compound was evaluated by testing the the inhibitory effect of the compound on cAMP production in HEK293 cells. The cAMP concentration test was performed according to the method described in the kit instructions. The test concentration of the compound was 0.1 nM to 10000 nM. 8-OH-DPAT was used as a positive control. The $EC_{50}$ was calculated by Excelfit software. The results were shown in Table 2.

TABLE 2

| Test Compound | $5-HT_{1A}$ Agonistic Activity ($EC_{50}$, nmol/L) |
|---|---|
| Compound of Example 5 | 450 |
| Compound of Example 11 | 1700 |
| Compound of Example 12 | 2300 |
| Compound of Example 14 | 514 |
| Compound of Example 21 | 238 |
| Compound of Example 23 | 1900 |
| Compound of Example 27 | 1200 |
| Compound of Example 35 | 5900 |
| Compound of Example 37 | 3030 |
| Compound of Example 38 | 4580 |
| Compound of Example 56 | 150 |
| Compound of Example 57 | 110 |
| Positive Control | 12.0 |

It can be seen from the above that the tested compounds have good antagonistic activity on the dopamine $D_1$ and $D_2$ receptors, and have an agonistic effect on the $5-HT_{1A}$ receptor. They can be used to prepare a medicament for treating the central nervous system disease, especially $D_1$, $D_2$, $5-HT_{1A}$ receptor-related diseases.

Efficacy Tests

1) Sedative and Hypnotic Effects

Figure 2:
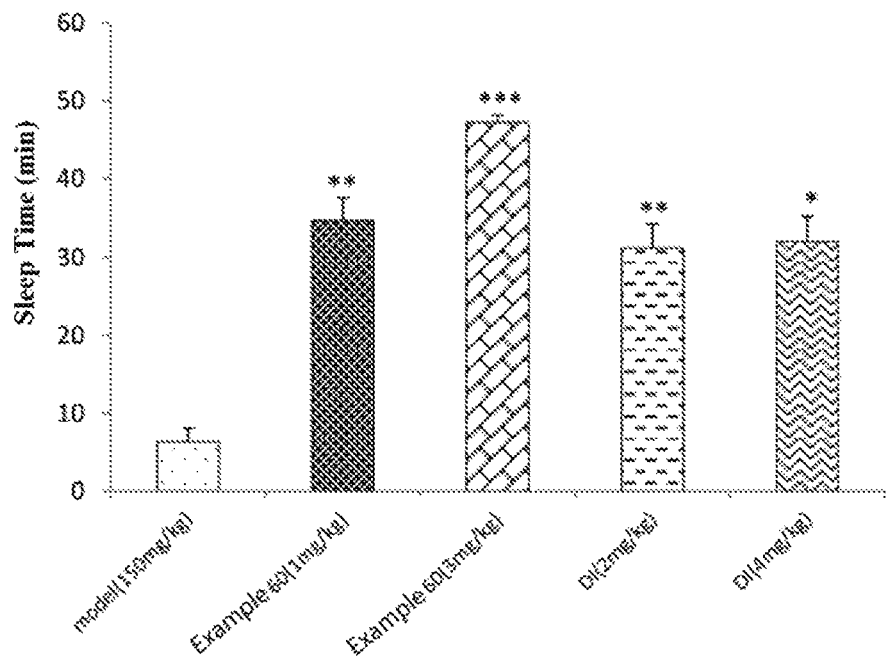
FIG. 2 is a bar graph of the effect of a single-dose administration of Example 60 on the sleep time of PCPA-induced insomnia model in rats treated with sodium pentobarbital.

The sedative and hypnotic effects of Example 60 were evaluated using a model of insomnia induced by injection with 4-Chlorophenylalanine (PCPA) in rats. The results were shown in FIGS. 1 to 2.

Dosage and method of administration: PCPA was administered at a dose of 150 mg/kg. PCP was administered by a single intraperitoneal injection at 72 hours before the experiment in all Wistar rats. The diazepam group (DI) was administered at a dose of 2 mg/kg and 4 mg/kg, a single intraperitoneal injection; the test drug group was administered at a dose of 1 mg/kg and 3 mg/kg, a single intragastric administration; sodium pentobarbital was administered at a dose of 25 mg/kg, a single intraperitoneal injection. The administration volume was 10 ml/kg. On the day of the test, the model group was given sodium pentobarbital 30 minutes after the same volume of physiological saline was given; the DI group was given sodium pentobarbital 30 minutes after DI was administered; the test drug group was given sodium pentobarbital 60 minutes after the drug was administered.lndex observation: After the administration of sodium pentobarbital, the rats' response was closely observed. The time from the administration to 1 minute after the righting reflex disappeared is the sleep latency. The time from 1 minute after the righting reflex disappeared to the point that the righting reflex returned is sleep time. It can be seen from FIGS. 1-2 that Example 60 can significantly prolong the sleep time of model rats at a dose of 1 mg/kg, and can significantly reduce the sleep latency and prolong the sleep time of insomnia rats induced by PCPA at a dose of 3 mg/kg. Example 60 had a good hypnotic effect.

2) PCP-induced high spontaneous activity test in mice

PCP (phencylidine) was dissolved in physiological saline to prepare a 7 mg/kg solution. The test compound was formulated with a 0.5% CMC-Na solution to a solution with suitable concentration, ready-to-use. Male ICR mice were 18-22 g. Mice were randomly divided into a solvent control group, a model control group, a positive control group, and each test drug group during the test. There were 8 mice in each group. Mice in each group were given each test drug by gavage. 45 minutes after the test drug was administered, mice were injected with a PCP (7 mg/kg) solution intraperitoneally. The spontaneous, open field video analysis system was used to record the mouse movement trajectory within 45 min after administration of test drug or saline, and then the mouse movement trajectory within 75 min after PCP administration. Spontaneous, open field video analysis system was used to analyze the mouse's movement trajectory, and the total distance of the movement of the mice in each group was counted. The result was expressed as mean±SD. Results were analyzed by one-way analysis of variance.

After administration of PCP, the spontaneous activity of mice increased significantly compared with the physiological saline group. The test compounds at the following doses (Table 3) can significantly reduce the high spontaneous activity of mice induced by PCP, which is significantly different from the model group. The compound of the present invention is orally effective, its effective dose is lower than that of l-stepholidine, and its efficacy is maintained for a long time. However, l-stepholidine has a high effective dose, fast metabolism, and short duration of effect.

TABLE 3

| Test Compound | Effective Dose (mg/kg) |
|---|---|
| Compound of Example 1 | 20 |
| Compound of Example 2 | 20 |
| Compound of Example 5 | 10 |
| Compound of Example 7 | 10 |
| Compound of Example 11 | 10 |
| Compound of Example 13 | 10 |
| Compound of Example 14 | 10 |
| Compound of Example 17 | 20 |
| Compound of Example 18 | 20 |
| Compound of Example 19 | 20 |
| Compound of Example 21 | 20 |
| Compound of Example 25 | 20 |
| Compound of Example 33 | 20 |
| Compound of Example 34 | 20 |
| Compound of Example 36 | 10 |
| Compound of Example 40 | 20 |
| Compound of Example 41 | 3 |
| Compound of Example 42 | 10 |
| Compound of Example 46 | 10 |
| Compound of Example 47 | 10 |
| Compound of Example 49 | 10 |
| Compound of Example 50 | 10 |
| Compound of Example 52 | 20 |
| Compound of Example 53 | 20 |
| Compound of Example 56 | 20 |
| Compound of Example 57 | 20 |
| l-stepholidine | >100 |

The invention claimed is:

1. A tetrahydroprotoberberine compound of formula (I-A-1), enantiomers, diastereomers, racemates or mixtures thereof, or pharmaceutically acceptable salts, crystalline hydrates or solvates thereof,

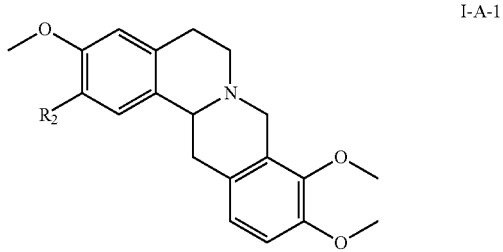

I-A-1 wherein,

R2 is selected from halogen, C1-C6 alkyl, C3-C6 cycloalkyl, C2-C6 alkenyl, C2-C6 alkynyl, halo-C1-C6 alkyl, amino, C1-C6 alkyl substituted amino, C1-C6 alkanoyl substituted amino, C1-C6 alkyl sulfonyl substituted amino, cyano, carboxy, aldehyde group, amino-C1-C6 alkyl, hydroxy-C1-C6 alkyl, cyano-C1-C6 alkyl, C1-C6 alkanoyl, halo-C1-C6 alkanoyl, sulfoamido, C1-C6 alkyl substituted sulfoamido, carbamoyl, C1-C6 alkyl substituted carbamoyl, carboxy-C1-C6 alkyl, C1-C6 alkyl sulfonyl, halo-C1-C6 alkyl sulfonyl, C1-C6 alkyl substituted amino-C1-C6 alkyl, C1-C6 alkanoyl substituted amino-C1-C6 alkyl, C1-C6 alkoxycarbonyl, carbamoyl-C1-C6 alkyl, or C1-C6 alkyl substituted carbamoyl-C1-C6 alkyl; or R2 is selected from halogen, mercapto, halo-C1-C4 alkoxy, hydroxy-C1-C4 alkoxy, C1-C4 alkylthio, C1-C4 alkyl, C3-C5 cycloalkyl, C3-C5 cycloalkoxy, C2-C4 alkenyl, C2-C4 alkenyloxy, C2-C4 alkynyl, C2-C4 alkynyloxy, halo-C1-C4 alkyl, amino, C1-C4 alkyl substituted amino, C1-C4 alkanoyl substituted amino, C1-C4 alkyl sulfonyl substituted amino, cyano, carboxy, aldehyde group, amino-C1-C4 alkyl group, hydroxy-C1-C4 alkyl, cyano-C1-C4 alkyl group, C1-C4 alkanoyl, halo-C1-C4 alkanoyl, sulfoamido, C1-C4 alkyl substituted sulfoamido, carbamoyl, C1-C4 alkyl substituted carbamoyl, carboxy-C1-C4 alkyl, C1-C4 alkansulfonyl, halo-C1-C4 alkansulfonyl, C1-C4 alkyl substituted amino-C1-C4 alkyl, C1-C4 alkanoyl substituted amino-C1-C4 alkyl, C1-C4 alkoxycarbonyl, carbamoyl-C1-C4 alkyl, or C1-C4 alkyl substituted carbamoyl-C1-C4 alkyl; or R2 is selected from fluorine, chlorine, bromine, mercapto, trifluoromethoxy, —SCH$_3$, —SCH$_2$CH$_3$, methyl, ethyl, propyl, isopropyl, t-butyl, trifluoromethyl, bromomethyl, chloromethyl, vinyl, amino, N-methylamino, N-ethylamino, N,N-dimethylamino, N,N-diethylamino, cyano, carboxyl, aldehyde group, —CH$_2$NH$_2$, —CH$_2$CH$_2$NH$_2$, —CH$_2$OH, —CH$_2$CH$_2$OH, —CH$_2$CN, —CH$_2$CH$_2$CN, formyl, acetyl, propionyl, trifluoroacetyl, sulfo amido, carbamoyl, N-methylcarbamoyl, N, N-dimethylcarbamoyl, N-ethylcarbamoyl, N,N-diethylcarbamoyl, —CH$_2$CO$_2$H, —CH$_2$CH$_2$CO$_2$H, —SO$_2$CH$_3$, —SO$_2$CF$_3$, —CH$_2$NHMe, —CH$_2$NMe$_2$, —CH$_2$CONH$_2$, —CH$_2$CONHMe or —CH$_2$CONMe$_2$.

2. The tetrahydroprotoberberine compound, enantiomers, diastereomers, racemates or mixtures thereof, or pharmaceutically acceptable salts, crystalline hydrates or solvates thereof, wherein the compound is selected from:
   (1) (S)-2-methyl-3,9,10-trimethoxy-6,8,13,13a-tetrahydro-5H-dibenzo[a,g] quinolizine;
   (2) (S)-2-n-propyl-3,9,10-trimethoxy-6,8,13,13a-tetrahydro-5H-dibenzo[a,g] quinolizine;
   (3) (S)-2-isobutyl-3,9,10-trimethoxy-6,8,13,13a-tetrahydro-5H-dibenzo[a,g] quinolizine;
   (4) (S)-2-cyano-3,9,10-trimethoxy-6,8,13,13a-tetrahydro-5H-dibenzo[a,g] quinolizine;
   (5) (S)-2-carbamoyl-3,9,10-trimethoxy-6,8,13,13a-tetrahydro-5H-dibenzo[a,g] quinolizine;
   (6) (S)-2-formyl-3,9,10-trimethoxy-6,8,13,13a-tetrahydro-5H-dibenzo[a,g] quinolizine;
   (7) (S)-2-hydroxymethy-3,9,10-trimethoxy-6,8,13,13a-tetrahydro-5H-dibenzo[a,g] quinolizine;
   (8) (S)-2-carboxy-3,9,10-trimethoxy-6,8,13,13a-tetrahydro-5H-dibenzo[a,g] quinolizine;

(9) (S)-2-ethoxycarbonyl-3,9,10-trimethoxy-6,8,13,13a-tetrahydro-5H-dibenzo[a,g] quinolizine;
(10) (S)-2-aminomethyl-3,9,10-trimethoxy-6,8,13,13a-tetrahydro-5H-dibenzo[a,g] quinolizine;
(11) (S)-2-acetaminomethyl-3,9,10-trimethoxy-6,8,13,13a-tetrahydro-5H-dibenzo[a,g] quinolizine;
(12) (S)-2-acetyl-3,9,10-trimethoxy-6,8,13,13a-tetrahydro-5H-dibenzo[a,g] quinolizine;
(13) (S)-2-amino-3,9,10-trimethoxy-6,8,13,13a-tetrahydro-5H-dibenzo[a,g] quinolizine;
(14) (S)-2-acetylamino-3,9,10-trimethoxy-6,8,13,13a-tetrahydro-5H-dibenzo[a,g] quinolizine;
(15) (S)-2-bromo-3,9,10-trimethoxy-6,8,13,13a-tetrahydro-5H-dibenzo[a,g] quinolizine;
(16) (S)-2-chloro-3,9,10-trimethoxy-6,8,13,13a-tetrahydro-5H-dibenzo[a,g] quinolizine;
(17) (S)-2-vinyl-3,9,10-trimethoxy-6,8,13,13a-tetrahydro-5H-dibenzo[a,g]quinolizine;
(18) (S)-2-hydroxyethyl-3,9,10-trimethoxy-6,8,13,13a-tetrahydro-5H-dibenzo[a,g] quinolizine;
(19) (S)-2,3,10-trimethoxy-9-cyano-6,8,13,13a-tetrahydro-5H-dibenzo[a,g] quinolizine;
(20) (S)-2,3,10-trimethoxy-9-carbamoyl-6,8,13,13a-tetrahydro-5H-dibenzo[a,g] quinolizine;
(21) (S)-2,3,10-trimethoxy-9-acetyl-6,8,13,13a-tetrahydro-5H-dibenzo[a,g] quinolizine;
(22) (S)-2,3,10-trimethoxy-9-aminomethyl-6,8,13,13a-tetrahydro-5H-dibenzo[a,g] quinolizine;
(23) (S)-2,3,10-trimethoxy-9-acetylaminomethyl-6,8,13,13a-tetrahydro-5H-dibenzo[a,g] quinolizine;
(24) (S)-2,3,10-trimethoxy-9-formyl-6,8,13,13a-tetrahydro-5H-dibenzo[a,g] quinolizine;
(25) (S)-2,3,10-trimethoxy-9-hydroxymethyl-6,8,13,13a-tetrahydro-5H-dibenzo[a,g] quinolizine;
(26) (S)-2,3,9-trimethoxy-10-methyl-6,8,13,13a-tetrahydro-5H-dibenzo[a,g] quinolizine;
(27) (S)-2,3,9-trimethoxy-10-cyano-6,8,13,13a-tetrahydro-5H-dibenzo[a,g] quinolizine;
(28) (S)-2,3,9-trimethoxy-10-carbamoyl-6,8,13,13a-tetrahydro-5H-dibenzo[a,g] quinolizine;
(29) (S)-2,3,9-trimethoxy-10-formyl-6,8,13,13a-tetrahydro-5H-dibenzo[a,g] quinolizine;
(30) (S)-2,3,9-trimethoxy-10-hydroxymethyl-6,8,13,13a-tetrahydro-5H-dibenzo[a,g] quinolizine;
(31) (S)-2,3 ,9-trimethoxy-10-aminomethyl-6, 8,13,13a-tetrahydro-5H-dibenzo[a,g] quinolizine;
(32) (S)-2,3,9-trimethoxy-10-acetaminomethyl-6,8,13,13a-tetrahydro-5H-dibenzo[a,g] quinolizine;
(33) (S)-2,10-diamino-3,9-dimethoxy-6,8,13,13a-tetrahydro-5H-dibenzo[a,g] quinolizine;
(34) (S)-2,10-diacetylamido-3,9-dimethoxy-6,8,13,13a-tetrahydro-5H-dibenzo[a,g] quinolizine;
(35) 2,3-dicyano-9,10-dimethoxy-6,8,13,13a-tetrahydro-5H-dibenzo[a,g] quinolizine;
(36) 9,10-dimethoxy-5,6,13,13a-tetrahydroisoquinolino[3,2-a]pyrrolo[3,4-g]isoquinoline-1,3(2H,8H)-dione;
(37) (S)-2,10-dicyano-3,9-dimethoxy-6,8,13,13a-tetrahydro-5H-dibenzo[a,g] quinolizine;
(38) (S)-2,10-dicarbamoyl-3,9-dimethoxy-6,8,13,13a-tetrahydro-5H-dibenzo[a,g] quinolizine;
(39) 2,3-dicarbamoyl-9,10-dimethoxy-6,8,13,13a-tetrahydro-5H-dibenzo[a,g] quinolizine;
(40) (S)-4,10,11-trimethoxy-3,6,7,9,14,14a-hexahydro-imidazo[4,5-h]isoquinolino [3,2-a]isoquinolin-2(1H)-one;
(41) (S)-4,10,11-trimethoxy-3,6,7,9,14,14a-Hexahydro-imidazo[4,5-h] isoquinolino [3,2-a]isoquinoline-2(1H)-thione;
(42) (S)-4,10,11-trimethoxy-1,6,7,9,14,14a-hexahydro-imidazo[4,5-h] isoquinolino [3,2 a]isoquinoline;
(43) (S)-4,10,11-trimethoxy-1,6,7,9,14,14a-hexahydroisoquinolino[3,2-a][1,2,3] triazolo [4,5-h]isoquinoline;
(44) 9,10-dimethoxy-1,5,6,8,13,13a-hexahydroimidazo [4,5-g]isoquinolino[3,2-a] isoquinoline;
(45) 9,10-dimethoxy-6,8,13,13a-tetrahydro-5H-isoquino [3,2-a]oxazolo[4,5-g] isoquinolin;
(46) 9,10-dimethoxy-3,5,6,8,13,13a-hexahydro-2H-isoquino[3,2-a]oxazolo[4,5-g] isoquinolin-2-one;
(47) 10,11-dimethoxy-4,6,7,9,14,14a-hexahydroisoquinolino[3,2-a][1,4]oxazino[3,2-g] isoquinolin-3(2H)-one;
(48) 10,11-dimethoxy-7,9,14,14a-tetrahydro-6H-isoquino [3,2-a]oxazolo[5,4-h] isoquinoline;
(49) 10,11-dimethoxy-6,7,14,14a-tetrahydro-1H-isoquino [3,2-a]oxazolo[5,4-h] isoquinolin-2(9H)-one;
(50) 11,12-dimethoxy-3,7,8,10,15,15a-hexahydroisoquinolino[3,2-a][1,4]oxazino [2,3-h] isoquinolin-2(1H)-one;
(51) (S)-2-(difluoromethoxy)-3,9,10-trimethoxy-6,8,13,13a-tetrahydro-5H-dibenzo[a,g] quinolizine;
(52) (S)-2-allyloxy-3,9,10-trimethoxy-6,8,13,13a-tetrahydro-5H-dibenzo[a,g] quinolizine;
(53) (S)-2-cyclopropoxy-3,9,10-trimethoxy-6,8,13,13a-tetrahydro-5H-dibenzo[a,g] quinolizine;
(54) (S)-2-cyclopentyloxy-3,9,10-trimethoxy-6,8,13,13a-tetrahydro-5H-dibenzo[a,g] quinolizine;
(55) (S)-2,10-di(hydroxyethoxy)-3,9-dimethoxy-6,8,13,13a-tetrahydro-5H-dibenzo[a,g] quinolizine;
(56) (S)-2,3,10-trimethoxy-9-hydroxyethoxy-6,8,13,13a-tetrahydro-5H-dibenzo[a,g] quinolizine;
(57) (S)-2,3,10-trimethoxy-9-cyclopropyloxy-6,8,13,13a-tetrahydro-5H-dibenzo[a,g] quinolizine;
(58) (S)-2,3,10-trimethoxy-9-cyclopentyloxy-6,8,13,13a-tetrahydro-5H-dibenzo[a,g] quinolizine;
(59) (S)-2,3,9-trimethoxy-10-cyclopropyloxy-6,8,13,13a-tetrahydro-5H-dibenzo [a,g] quinolizine; and
(60) (S)-2-methanesulphonylamino-3,9,10-trimethoxy-6,8,13,13a-tetrahydro-5H-dibenzo [a,g] quinolizine.

3. A pharmaceutical composition, comprising a therapeutically effective amount of the tetrahydroprotoberberine compound, enantiomers, diastereomers, racemates or mixtures thereof, or pharmaceutically acceptable salts, crystalline hydrates or solvates thereof of claim 1, and optionally a pharmaceutically acceptable carrier.

4. A pharmaceutical composition, comprising a therapeutically effective amount of the tetrahydroprotoberberine compound, enantiomers, diastereomers, racemates or mixtures thereof, or pharmaceutically acceptable salts, crystalline hydrates or solvates thereof of claim 2, and optionally a pharmaceutically acceptable carrier.

* * * * *